(12) United States Patent
Debs et al.

(10) Patent No.: US 6,806,084 B1
(45) Date of Patent: *Oct. 19, 2004

(54) METHODS FOR COMPOSITIONS FOR IN VIVO GENE DELIVERY

(75) Inventors: Robert James Debs, Mill Valley, CA (US); Ning Zhu, El Cerrito, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 284 days.

This patent is subject to a terminal disclaimer.

(21) Appl. No.: 09/090,030

(22) Filed: Jun. 10, 1998

Related U.S. Application Data

(63) Continuation of application No. 08/246,376, filed on May 19, 1994, now Pat. No. 5,827,703, which is a continuation of application No. 07/992,687, filed on Dec. 17, 1992, now abandoned, which is a continuation-in-part of application No. 07/927,200, filed on Aug. 6, 1992, now abandoned, which is a continuation-in-part of application No. 07/894,498, filed on Jun. 4, 1992, now abandoned.

(51) Int. Cl.[7] .................... C12N 15/63; C12N 15/88; A61K 9/127
(52) U.S. Cl. ............... 435/455; 435/320.1; 435/458; 424/450
(58) Field of Search ............... 424/93.21; 514/44; 435/69.1, 320.1, 325, 455, 458; 536/23.1

(56) References Cited

U.S. PATENT DOCUMENTS

| | | | |
|---|---|---|---|
| 3,826,255 A | | 7/1974 | Havstad et al. ............. 128/194 |
| 4,046,146 A | | 9/1977 | Rosskamp et al. ......... 128/266 |
| 4,253,468 A | | 3/1981 | Lehmbeck ................. 128/726 |
| 4,268,460 A | | 5/1981 | Boiarski et al. ............ 261/1 |
| 4,394,448 A | | 7/1983 | Szoka ........................ 435/455 |
| 4,510,929 A | | 4/1985 | Bordoni et al. ........ 128/200.14 |
| 4,649,911 A | | 3/1987 | Knight et al. .......... 128/200.21 |
| 4,689,320 A | * | 8/1987 | Kaji ............................. 514/44 |
| 4,738,927 A | | 4/1988 | Taniguchi et al. .......... 435/243 |
| 4,804,678 A | | 2/1989 | Augstein et al. ............ 514/456 |
| 4,877,619 A | * | 10/1989 | Richer ........................ 424/450 |
| 4,897,355 A | * | 1/1990 | Eppstein et al. ............ 435/325 |
| 4,946,787 A | | 8/1990 | Eppstein ..................... 435/325 |
| 5,032,407 A | | 7/1991 | Wagner ....................... 424/520 |
| 5,075,229 A | | 12/1991 | Hanson ....................... 435/455 |
| 5,240,842 A | | 8/1993 | Mets ........................... 435/455 |
| 5,240,846 A | | 8/1993 | Collins ....................... 435/325 |
| 5,264,618 A | * | 11/1993 | Felgner et al. .............. 560/224 |
| 5,279,833 A | * | 1/1994 | Rose ........................... 424/450 |
| 5,283,185 A | * | 2/1994 | Epand et al. ................ 435/325 |
| 5,328,470 A | * | 7/1994 | Nabel et al. ................ 604/101 |
| 5,338,837 A | * | 8/1994 | Kahne ............................ 536/5 |
| 5,622,854 A | * | 4/1997 | Draper ........................ 435/366 |
| 5,641,484 A | * | 6/1997 | Hung et al. .............. 424/93.21 |
| 5,676,954 A | | 10/1997 | Brigham ..................... 424/450 |
| 5,756,353 A | | 5/1998 | Debs .......................... 435/375 |
| 5,827,703 A | * | 10/1998 | Debs et al. ................. 435/455 |

FOREIGN PATENT DOCUMENTS

| | | |
|---|---|---|
| DE | 3545126 A | 6/1987 |
| EP | 0 281 246 A2 | 9/1988 |
| EP | 0 469 632 A1 | 2/1992 |
| GB | 354126 | 8/1931 |
| WO | 89/02469 | 3/1989 |
| WO | 89/12109 | 12/1989 |
| WO | 90/06997 | 6/1990 |
| WO | WO/90/10448 | 9/1990 |
| WO | 90/11092 | 10/1990 |
| WO | 90/12878 | 11/1990 |
| WO | WO 91/02796 | 3/1991 |
| WO | WO 91/06309 | 5/1991 |
| WO | WO 91/15501 | 10/1991 |
| WO | WO 91/17773 | 11/1991 |
| WO | WO 92/05252 | 4/1992 |
| WO | WO 92/19749 | 11/1992 |
| WO | WO/93/04701 | 3/1993 |
| WO | WO/93/12240 | 6/1993 |
| WO | WO 93/24640 | 12/1993 |

OTHER PUBLICATIONS

Wang et al., PNAS, vol. 84, pp. 7851–7855, 1987.*
New Riverside University Dictionary, The Riverside Publishing Company, 1994, p. 67.*
Gao et al. (Biochemical and Biophysical Research Communications, vol. 179, No. 1, 1991, pp. 280–285).*
Behr (PNAS, vol. 86, pp. 6982–6986, 1989).*
Brigham et al. (The American Journal of the Medical Sciences, vol. 298, 4:278–281), 1989.*
Zhou et al. (Biochimica et Biophysica Acta, 1065, 1, 8–14, 1991).*
Brunette et al. (Nucleic Acids Res., vol. 20, 5, 1151), 1992.*
Guo et al., J. Liposome Res, 1, 1989, pp. 319–337.*
Benvenisty et al. (PNAS, vol 83, pp. 9551–9555, 1986).*

(List continued on next page.)

Primary Examiner—Dave T. Nguyen
(74) Attorney, Agent, or Firm—Townsend & Townsend & Crew LLP

(57) ABSTRACT

Novel methods and compositions are provided for introducing a gene capable of modulating the genotype and phenotype into two or more tissues following systemic administration. The gene can be introduced into a mammalian host by way of an expression vector either as naked DNA or complexed to lipid carriers, particularly cationic lipid carriers. Multiple individual tissues can be transfected using naked DNA. Using a DNA:lipid carrier complex, multiple tissues and cell types can be transfected. The techniques and compositions find use in the palliation or treatment of any of a variety of genetic-based disorders.

32 Claims, 71 Drawing Sheets

(9 of 71 Drawing Sheet(s) Filed in Color)

OTHER PUBLICATIONS

Dzau, Victor J. et al., (1993) Gene therapy for cardiovascular disease, TIBTECH 11:205–210.

Friedmann, Theodore (1989) "Progress Toward Human Gene Therapy", *Science* 244:1275–1281.

Zhu, Ning, et al., (1993) "Systemic Gene Expression After Intravenous DNA Delivery into Adult Mice", *Science*, 261:209–211.

Rosenfeld, et al. (1992) "In vivo Transfer of the Human Cystic Fibrosis Transmembrane Conductance Regulator Gene to the Airway Epithelium", *Cell*, 68:143–155.

Brigham, et al. (1989) "Expression of a Prokaryotic Gene in Cultured Lung Endothelial Cells after Lipofection with a Plasmid Vector", *Am. J. Respir. Cell. Mol. Biol.*, 1:95–100.

Alton, E., et al. (1993) "Non–invasive liposome–mediated gene delivery can correct the ion transport defect in cystic fibrosis mutant mice", *Nature Genetics*, 5:135–142.

Huang, et al. (1990) "The Simian Virus 40 Small–t Intron, Present in Many Common Expression Vectors, Leads to Abberrant Splicing", *Molecular and Cellular Biology*, 10(4): 1805–1810.

Matteucci, et al., "Synthesis of Deoxyoligonucleotides on a Polymer Support," *J. Am. Chem. Soc.*, vol. 103:3185–3191 (1981).

Volloch, et al., "Stability of Globin mRNA in Terminally Differentiating Murine Erythroleukemia Cells," *Cell* vol. 23:509–514 (1981).

Bothwell, et al., "Heavy–Chain Variable Region Contribution to the NP Family of Antibodies: Somatic Mutation Evident in a γa Variable Region," *Cell* vol. 24:625–637 (1981).

Edge, et al., "Total Synthesis of a Human Leukocyte Interferon Gene," *Nature*, vol. 292:756–762 (1981).

Schaefer–Ridder, et al., "Liposomes as Gene Carriers: Efficient Transformation of Mouse L Cells by Thymidine Kinase Gene," *Science*, vol. 215:166–168 (1981)Gorman, et al., "Recombinant Genomes which Express Chloramphenicol Acetyltransferase in Mammalian Cells," *Molecular and Cellular Biology*, vol. 2 No. 9:1044–1051 (1982).

Gorman, et al., "The Rous Sarcoma Virus Long Terminal Repeat is a Strong Promoter when Introduced into a Variety of Eukaryotic Cells by DNA–Mediated Transfection," *PNAS (USA)*, vol. 79:6777–6781 (1982).

Long, et al., "Complete Sequence of the cDNA for Human α–Antitrypsin and the Gene for the S. Variant," *Biochemistry*, vol. 23:4828–4837 (1984).

Nambair, et al., "Total Synthesis and Cloning of a Gene Coding for the Ribonuclease S. Protein," *Science*, vol. 223:1299–1301 (1984).

Jay, et al., "Chemical Synthesis of a Biologically Active Gene for Human Immune Interferon–γ," *Journal of Biological Chemistry*, vol. 259, No. 10:6311–6317 (1984).

Kunkel, Thomas, "Rapid and Efficient Site–specific Mutagenesis without Phenotypic Selection," *PNAS (USA)*, vol. 82:488–492 (1985).

Boshart, et al., "A Very Strong Enhancer is Located Upstream of an Immediate Early Gene of Human Cytomegalovirus," *Cell*, vol. 41:521–530 (1985).

Papahadjopoulos et al., "Cochleate Lipid Cylinders: Formation by Fusion of Unilamellar Lipid Vesicles," *Biochimica et Biophysica Acta*, vol. 394:483–491 (1975).

Deamer et al., "Large Volume Liposomes by an Ether Vaporization Method," *Biochimica et Biophysica Acta*, vol. 443:629–634 (1976).

Ostro, et al., "Incorporation of High Molecular Weight RNA into Large Artificial Lipid Vesicles," *Biochemical and Biophysical Research Communications*, vol. 76, No. 3:836–842 (1977).

Enoch, et al., "Formation and Properties of 1000–A–Diameter, Single–Bilayer Phospholipid Vesicles," *PNAS (USA)*, vol. 76, No. 1:145–149 (1979).

Wilson, et al., "The Introduction of Poliovirus RNA into Cells via Lipid Vesicles (Liposomes)," *Cell*, vol. 17:77–84 (1979).

Fraley, et al., "Entrapment of a Bacterial Plasmid in Phospholipid Vesicles: Potential for Gene Transfer," *PNAS (USA)*, vol. 76, No. 7:3348–3352 (1979).

Huang, et al., "Monoclonal Antibody Covalently Coupled with Fatty Acid," *Journal of Biological Chemistry*, vol. 255, No. 17:8015–8018 (1980).

Fraley, et al., "Introduction of Liposome–Encapsulated SV40 DNA into Cells," *Journal of Biological Chemistry*, vol. 255 No. 21:10431–10435 (1980).

Leserman, et al., "Targeting to Cells of Flourescent Liposomes Covalently Coupled with Monoclonal Antibody of Protein A," *Nature*, vol. 288:602–604 (1980).

Beaucage, et al., "Deoxynucloside Phosphoramidites—A New Class of Key Intermediated for Deoxypolynucleotide Synthesis," *Tetrahedron Letters*, vol. 22 No. 20:1859–1862 (1981).

Duckworth, et al., "Rapid Synthesis of Oligodeoxyribonucleotides VI. Efficient, Mechanised Synthesis of Heptadecadeoxyribonucleotides by an Improved Solid Phase Phosphotriester Route," *Nucleic Acids Research*, vol. 9 No. 7:1691–1706 (1981).

Martin, et al., "Immunospecific Targeting of Liposomes to Cells: A Novel and Efficient Method for Covalent Attachment of Fab' Fragments via Disulfide Bonds," *Biochemistry*, vol. 20:4229–4238 (1981).

Stinski, et al., "Activation of the Major Immediate Early Gene of Human Cytomegalovirus by cis–Acting Elements in the Promoter–Regulatory Sequence and by Virus–specific Trans–acting Components," *Journal of Virology*, vol. 55 No. 2:431–441 (1985).

Cullen, B.R., "Trans–Activation of Human Immunodeficiency Virus Occurs via a Bimodal Mechanism," *Cell*, vol. 46:973–982 (1986).

Benvenisty, et al., "Direct Introduction of Genes into Rats and Expression of the Genes," *PNAS (USA)*, vol. 83:9551–9555 (1986).

Debs, et al., "Successful Treatment with Aerosolized Pentamidine of Pneumocystis Carinii Pneumonia in Rats," *Antimicrobial Agents and Chemotherapy*, vol. 31, No. 1:37–41 (1987).

Montgomery, et al., Aerosolised Pentamidine as Sole Therapy for Pneumocystis Carinii Pneumonia in Patients with Acquired Immunodeficiency Syndrome, *Lancet*, vol. 11:480–483 (1987).

Felgner, et al., "Lipofection: A Highly Efficient, Lipid–Mediated DNA–Transfection Procedure," *PNAS (USA)*, vol. 84:7413–7417 (1987).

Wang, et al., "pH Sensitive Immunoliposomes Mediate Target–Cell–Specific Delivery and Controlled Expression of a Foreign Gene in a Mouse," *PNAS (USA)*, vol. 84:7851–7855 (1987).

Mannino, et al., "Liposome Mediated Gene Transfer," *Biotechniques*, vol. 6 No. 7:682–690 (1988).

Sakai, et al., "Hormone–Mediated Repression: A Negative Clucocorticoid Response Element from the Bovine Prolactin Gene," *Genes and Development,* vol. 2:1144–1154 (1988).

Stamatatos, et al., "Interactions for Cationic Lipid Vesicles with Negatively Charged Phospholipid Vesicles and Biological Membranes," *Biochemistry,* vol. 27:3917–3925 (1988).

Debs, et al., "Lung–Specific Delivery of Cytokines Induces Sustained Pulmonary and Systemic Immunomodulation in Rats," *J. Immunology,* vol. 140 No. 10:3482–3488 (1988).

Wu, et al., "Receptor–Mediated Gene Delivery and Expression In Vivo," *J. Biological Chemistry,* vol. 263, No. 29:14621–14624 (1988).

Hubbard, et al., "Fate of Aerosolized Recombinant DNA–Produced α1–Antitrypsin: Use of the Epithelial Surface of the Lower Respiratory Tract to Administer Proteins of Therapeutic Importance," *PNAS (USA)*, vol. 86:680–684 (1989).

Kaneda, et al., "Increased Expression of DNA Cointroduced with Nuclear Protein in Adult Rat Liver," *Science,* vol. 243:375–378 (1989).

Malone, et al., "Cationic Liposome–Mediated RNA Transfection," *PNAS (USA)*, vol. 86:6077–6081 (1989).

Rommens, et al., "Identification of the Cystic Fibrosis Gene: Chromosome Walking and Jumping," *Science,* vol. 245:1059–1065 (1989).

Goodfellow, P.N., "Steady Steps Lead to the Gene," *Nature,* vol. 341:102–103 (1988).

Mizuno, et al., "In Vitro and In Vivo Expression of Human Interferon–β in Glioma Cells Transfected with its Gene Encapsulated in Liposomes," *J. Interferon Research,* vol. 9, Supp. 2:S151 (Abstract A1–8) (1989).

Huang, et al.,. "Intervening Sequences Increase Efficiency of RNA 3' Processing and Accumulation of Cytoplasmic RNA," *Nucleic Acids Research,* vol. 18 No. 4:937–947 (1990).

Ono, et al., "Plasmid DNAs Directly Injected into Mouse Brain with Lipofectin Can Be Incorporated and Expressed by Brain Cells," *Neuroscience Letters,* vol. 117:259–263 (1990).

Holt, et al., "Lipofection of cDNAs in the Embryonic Vertebrate Central Nervous System," *Neuron,* vol. 4:203–214 (1990).

Uhlmann, et al., "Antisense Oligonucleotides: A New Therapeutic Principle," *Chemical Reviews,* vol. 90 No. 4:543–584 (1990).

Debs, et al., "Regulation of Gene Expression In Vivo by Liposome–Mediated Delivery of a Purified Transcription Factor," *J. Biological Chemistry,* vol. 265 No. 18:10189–10192 (1990).

R.G. Crystal, "α1–Antitrypsin Deficiency, Emphysema, and Liver Disease", *The Journal of Clinical investigation, Inc.,* 85:1343–1352 (May 1990).

Ann–Bin Shyu et al., "The c–fos transcript is targeted for rapid decay by two distinct mRNA degradation pathways", *Genes & Development,* 3:60–72 (1989).

Rosenberg et al., "Gene Transfer into Human—Immunotherapy of Patients with Advanced Melanoma, Using Tumor–Infiltrating Lymphocytes Modified by Retroviral Gene Transduction", *The New England Journal of Medicine,* vol. 323, 9:570–578 (1990).

Burhans et al., "Identification of an Origin of Bidirectional DNA Replication in Mammalian Chromosomes", *Cell, 62:*955–965 (1990).

Nabel, et al., "Site–Specific Gene Expression In Vivo by Direct Gene Transfer into the Arterial Wall", *Science,* 249:1285–1288 (1990).

Verma, "Gene Therapy: Treatment of Disease by Introducing Healthy Genes into the Body is Becoming Feasible. But the Therapy will not reach its full potential until the genes can be coaxed to work throughout life", *Scientific American,* pp. 68–84 (1990).

Barr, et al., "Expression of Recombinant Genes in Myocardium In Vivo Following Direct Injection of DNA", *Clinical Research,* 39:2:152A (1991).

Kitsis, et al., "Behaviour of Genes Directly Transferred to Rat Heart In Vivo", *Clinical Research,* vol. 39, 2:152A (1991).

Hazinski, et al., "Localization and Induced Expression of Fusion Genes in the Rat Lung", *Am. J. Resp. Cell. Molec. Biol., 4:*206–209 (1991).

Hug, et al., "Lipsomes for the Transformation of Eukaryotic Cells", *Biochemica et Biophysica Acta, 1097:*1–17 (1991).

Palmiter, et al., Heterologous Introns can Enhance Expression of Transgenes in Mice, *PNAS (USA)*, *88:*478–482 (1991).

Felgner, et al., "Gene Therapeutics", *Nature, 349:*351–352 (1991).

Weatherall, "Gene Therapy Perspective", *Nature, 349:*275–276 (1991).

Fleischman, "Southwesten Internal Medicine Conference: Human Gene Therapy", *The American Journal of the Medical Sciences,* vol. 301, 5:353–363 (1991).

Kitsis, et al., "Hormonal Modulation of a Gene Injected into Rat Heart In Vivo", *PNAS (USA)*, 88:4138–4142 (1991).

Choi, et al., "A Generic Intron Increases Gene Expression in Transgenic Mice", *Molecular and Cellular Biology,* vol. 11, 6:3070–3074 (1991).

Lim, et al., "Direct In Vivo Gene Transfer into the Coronary and Peripheral Vasculatures of the Intact Dog", *Circulation,* vol. 83, 6:2007–2011 (1991).

Wu, et al., "Receptor–Mediated Gene Delivery In Vivo", *Journal of Biological Chemistry,* vol. 266, 22:14338–14342 (1991).

Acsadi, et al., "Human Dystrophin Expression in mdx Mice after Intramuscular Injection of DNA Constructs", *Nature, 352:*815–818 (1991).

Rosenberg, "Immunotherapy and Gene Therapy of Cancer", *Cancer Research (Supp.)* vol. 51, 18:5074S–5079S (1991).

Stone, R. Ed., "FDA Ponders Gene–Therapy Regulations", *Sciencescope,* p. 1575 (1991).

Anderson, "Human Gene Therapy", *Science, 256:*808–813 (1992).

Collins, "Cystic Fibrosis: Molecular Biology and Therapeutic Implications", *Science, 256:*774–783 (1992).

Cox, et al., Emphysema of Early Onset Associated with a Complete Deficiency of Alpha–1–Antitrypsin (null homozygotes)$^{1-3w}$, *Am. Rev. Respir. Dis.,* 137:371–375 (1988).

Gilbert, "Sequencing End–Labeled DNA with Base–Specific Chemical Cleavages", *Methods in Enzymology, 65:*499–560 (1980).

Wright, "A New Nebuliser", *Lancet,* 2:24–25 (1958).

Mercer, et al., "Operating Characteristics of Some Compressed–Air Nebulizers", *Am. Ind. Hyg. Assoc. J., 29:*66–78 (1968).

Raabe, "Particle Size Analysis Utilizing Grouped Data and the Log–Normal Distribution", *J. Aerosol Sci.,* 2:289–303 (1971).

Szoka, et al., "Procedure for preparation of liposomes with large internal aqueous space and high capture by reverse–phase evaporation", *PNAS (USA),* vol. 75, 9:4194–4198 (1978).

Mercer, "Production of Therapeutic Aerosols, Principles and Techniques", *Chest,* vol. 80, Supp. 6:813–817 (1981).

Straubinger, et al., "Liposomes as Carriers for Intracellular Delivery of Nucleic Acids", *Methods in Enzymology,* 101:512–527 (1983).

Gregoriadis, "Liposomes for drugs and vaccines", *Trends in Biotechnology,* vol. 3, 9:235–241 (1985).

Dobbs, "An improved method for isolating Type II cells in High Yield and Purity", *Amer. Rev. Respiratory Disease,* 134:141–145 (1986).

Debs, et al., "Selective enhancement of Pentamidine uptake in the lung by aerosolization and delivery in liposomes," *Amer. Rev. Respiratory Disease,* 135:731–737 (1986).

Lai, et al., "The essential role of microsomal deacetylase activity in the metabolic activation, DNA–(deoxyguanosin–8–yl)–2–aminofluorene adduct formation and initiation of liver tumors by N–hydroxy–2–acetylaminoflurorene in the livers of infant male $B6C3F_1$ mice", *Carcinogenesis,* 9:1295–1302 (1988).

Beardsley, et al., "Winning Candidate: A painstaking search identifies the gene for cystic fibrosi", *Sci. Am.,* 261:28–30 (1989).

Brigham, et al., "Rapid communication: in vivo transfection of murine lungs with a functioning prokaryotic gene using a liposome vehicle", *Am. J. Med. Sci.,* 298:278–281 (1989).

Montgomery, et al., "Aerosolized Pentamidine as second line therapy in patients with AIDS and *pneumocystis carinii* pneumonia", *Chest,* 95:747–751 (1989).

Debs, et al., "Biodistribution, tissue reaction and lung retention of Pentamidine aerosolized as three different salts," *Am. Rev. Respir. Dis.,* 142:1164–1167 (1990).

Leoung, et al., "Aerosolized Pentamidine for prophylaxia against *Pneumocystis carinii* pneumonia" *N. Eng. J. Med.,* 323:769–775 (1990).

Treat, et al., "Antitumor activity of liposome–encapsulated doxorubicin in advanced breast cancer: Phase II study", *J. Natl. Cancer Instit.,* 82:1706 (1990).

Rasmussen, "*Listeria monocytogenes* can be classifed into two major types according to the sequence of the listeriolysin gene", *Infect. and Immun.,* vol. 59, 11:3945–3951 (1991).

Canonico, et al., "Expression of a CMV promoter driven human α–1 antitrypsin gene in cultured lung endothelial cells and in the lungs of rabbits", *Clinical Research,* 39:219A (1991).

Holden, "Animal rights vet wins a round", *Science,* 253:964–965 (1991).

Marino, et al., "Localization of the Cystic Fibrosis Transmembrane Conductance Regulator in Pancreas", *J. Clin. Invest.,* 88:712–716 (1991).

M. Huang et al., Nucl. Acids Res. 18(4) ('90) 937–46.

Wickstrom, E. et al. *J. Biochem Biophys. Methods,* 13: 97–102 (1986).

N. Benvensity, et al., *PNAS,* 83:9551–9555 (Dec. 1986).

J. Wolf, et al., *Science,* 247 (Mar. 23, 1990) pp. 1465–1468.

J. Van Brunt, *Bio/Technology,* vol. 6, No. 10:1149–1154 (Oct. 1988).

A. Dusty Miller, *Nature,* 357:455–460 (Jun. 11, 1992).

N. Dillan, *TIBTECH,* 11:167–173 (May 1993).

H. San et al., *Human Gene Therapy,* 4:781–788 (1993).

R. Mulligan et al., *Science* 260:926–932 (May 14, 1993).

K. Mirani et al., *TIBTECH* 11:162–166 (May 1993).

D. Porteous et al, *TIBTECH* 11:173–181 (May 1993).

R. Mannino et al., *Bio Techniques,* vol. 6, 7:682–690 (1988).

M. Brant et al., *DNA & Cell Biol.,* vol. 10, 1:75–79 (1991).

N. Gough et al., EMBO J., vol. 4, #3 ('85) pp. 645–653.

A. Burgess, in Evered, Nugent & Whelan (Eds.) *Growth Factors in biology & Medicine,* CIBA Foundation Symposium 116, London, Primary '85, pp. 148–168.

M. Ostrowski, et al. *Mol. Cell. Biol.,* vol. 3, #11 (Nov. '83) pp. 2045–2057.

M.F. Stinski et al., *J. Virology,* vol. 55, No. 2 (1985) pp. 431–441.

P.O.P. Ts'o et al., *Annals of the N.Y. Acad. Sci.,* vol. 507 (1988) pp. 220–241.

M. Boshart et al., *Cell,* vol. 41 (1985) pp. 521–530.

R.J. Debs et al., *J. Immunology,* vol. 140 (1988) pp. 3482–3488.

C.M Gorman et al., *Mol. Cell. Biol.,* vol. 2., No. 9 (1982) pp. 1044–1051.

R.L. Brinster et al. *PNAS,* vol 85 (1988) pp. 836–840.

D.P. Rich et al., *Nature,* vol. 347 (1990) pp. 358–363.

E. Nabel et al., *Science,* vol. 249 (1990) pp. 1285–1288.

* cited by examiner

HCMV (Towne) -> Full Restriction Map

DNA sequence    616 b.p.    ggcgaccgccca ... agtgacgtaagt    linear

Positions of Restriction Endonucleases sites (unique sites underlined)

```
                         Mae II
                         Aha II
                         Aat II                Mae III
                         HinC II   Mae II                      Mae III
                         |         |           |               |
GGCGACCGCCCAGCGACCCCCGCCGTTGACGTCAATATAGTGACGTATGTTCCCATAGTAACGCCAATAGGGACTTTCCAT
CCGCTGGCGGGTCGCTGGGGGCGGCAACTGCAGTTATATCACTGCATACAAGGGTATCATTGCGGTTATCCCTGAAAGGTA
                         |         |          | |                            |
                         26        29         39 42                           80
                                   29
                                   30

Nde I
            Bgl I                           Rsa I                    |
            |                               |                        |
TGACGTCAATGGGTGGAGTATTTACGGTAAACTGCCCACTTGGCAGTACATCAAGTGTATCATATGCCAAGTCCGCCCCC
ACTGCAGTTACCCACCTCATAAATGCCATTTGACGGGTGAACCGTCATGTAGTTCACATAGTATACGGTTCAGGCGGGGG
|                   |                       |                                 |
82                  114                     126                               141
Mae II
Aha II
Aat II
|
82
83
```

```
         ScrF I
         Nci I
         Msp I
         Hpa II
         Bcn I
         Hae III
         Gdi II
         Eag I              Hinf I                    Mae II
         Eae I      BstU I    |            Mae III
Fnu4H I     |         |       |              |
   |||      •         •       •        •     •        •
GCGGCCGGGAACGGTGCATTGGAACGCGGATTCCCCGTGCCAAGAGTGACGTAAGT    616
CGCCGGCCCTTGCCACGTAACCTTGCGCCTAAGGGGCACGGTTCTCACTGCATTCA
   |||      •         •       •        •     •        •
561                                                       609
562                         585       589      606
562
562
563
565
565
565
565
565

Restriction Endonucleases site usage

Aat II      4     BspH I     —     EcoR V     —     Mnl I      —     Rsr II     3     Sac II     1
Acc I       —     BspM I     —     Esp I      —     Msc I      1     Sac I      —     Sal I      2
Afl II      —     BspM II    —     Fnu4H I    1     Mse I      1     Sac II     1     Sau3A I    1
Afl III     —     Bsr I      —     Fok I      1     Msp I      1     Sau3A I    —     Sau96 I    2
Aha II      5     BssH II    —     Fsp I      —     Nae I      —
Alu I       1     BstB I     —     Gdi II     —     Nar I      1

FIG. 6A
(CONTINUED)
```

| Enzyme | | | | Enzyme | | | | Enzyme | | | | Enzyme | | |
|---|---|---|---|---|---|---|---|---|---|---|---|---|---|---|
| Alw I | 1 | | | BstE II | 1 | | | Gsu I | – | | | Nci I | 1 | Sca I | – |
| AlwN I | – | | | BstN I | 1 | | | Hae I | 1 | | | Nco I | – | ScrF I | 3 |
| Apa I | – | | | BstU I | – | | | Hae II | 2 | | | Nde I | – | Sec I | 2 |
| ApaL I | – | | | BstX I | – | | | Hae III | – | | | Nhe I | 2 | SfaN I | 1 |
| Ase I | – | | | BsfY I | – | | | Hga I | 2 | | | Nla III | 2 | Sfi I | – |
| Asp718 | – | | | Bsu36 I | – | | | HgiA I | 2 | | | Nla IV | 1 | Sma I | 1 |
| Ava I | 1 | | | Cfr10 I | – | | | HgiE II | – | | | Not I | – | SnaB I | – |
| Ava II | – | | | Cla I | 1 | | | Hha I | – | | | Nru I | – | Spe I | – |
| Avr II | – | | | Dde I | – | | | HinC II | 2 | | | Nsi I | 2 | Sph I | – |
| BamH I | 1 | | | Dpn I | 2 | | | HinD III | – | | | Nsp7524 I | – | Spl I | – |
| Ban I | 1 | | | Dra I | – | | | Hinf I | 1 | | | NspB II | 2 | Ssp I | 1 |
| Ban II | – | | | Dra III | – | | | HinP I | – | | | NspH I | 1 | Stu I | – |
| Bbe I | – | | | Drd I | – | | | Hpa I | – | | | Pac I | – | Sty I | – |
| Bbv I | – | | | Dsa I | – | | | Hpa II | 2 | | | PaeR7 I | 2 | Taq I | 1 |
| Bbv II | 1 | | | Eae I | 1 | | | Hph I | 1 | | | PflM I | 1 | Tth111 I | – |
| Bcl I | – | | | Eag I | – | | | Kpn I | – | | | Ple I | – | Tth111 II | – |
| Bcn I | 1 | | | Ear I | – | | | Mae I | – | | | Pml I | – | Xba I | – |
| Bgl I | 2 | | | Eco47 III | – | | | Mae II | – | | | PpuM I | 7 | Xca I | – |
| Bgl II | 2 | | | Eco57 I | – | | | Mae III | – | | | Pst I | 3 | Xho I | – |
| BsaA I | – | | | EcoN I | – | | | Mbo I | – | | | Pvu I | 2 | Xcm I | – |
| Bsm I | 1 | | | EcoO109 I | – | | | Mbo II | – | | | Pvu II | 1 | Xma I | – |
| BsmA I | 2 | | | EcoR I | – | | | Mlu I | – | | | Rsa I | – | Xmn I | 5 |
| Bsp1286 I | 1 | | | EcoR II | – | | | Mme I | 1 | | | | | | |

| Enzyme | Site | Use | Site position | (Fragment length) | Fragment order |
|---|---|---|---|---|---|
| Alu I | ag/ct | 1 | 1( 471) | 472( 145) | 2 |
| Alw I | ggatc | 1 | 1( 548) | 549( 68) | 2 |
| Ava II | g/gwcc | 4/5 | 1( 543) | 544( 73) | 2 |
| Ban I | g/gyrcc | 1 | 1( 372) | 373( 244) | 2 |

FIG. 6A
(CONTINUED)

| Enzyme | Sequence | Offset | | | | | |
|---|---|---|---|---|---|---|---|
| Ban II | grgcy/c | | 1 | 1( | 470) | 1 | 471( 146) 2 |
| Bbv II | gaagac | 2/6 | 1 | 1( | 533) | 1 | 534( 83) 2 |
| BsaA I | yac/gtr | | 1 | 1( | 245) | 2 | 246( 371) 1 |
| Bsp1286 I | gdgch/c | | 1 | 1( | 470) | 1 | 471( 146) 2 |
| Bsr I | actgg | 1/-1 | 1 | 1( | 202) | 2 | 203( 414) 1 |
| BstN I | cc/wgg | | 1 | 1( | 497) | 1 | 498( 119) 2 |
| Eae I | y/ggccr | | 1 | 1( | 561) | 1 | 562( 55) 2 |
| Eag I | c/ggccg | | 1 | 1( | 561) | 1 | 562( 55) 2 |
| EcoR II | /ccwgg | | 1 | 1( | 497) | 1 | 498( 119) 2 |
| Fnu4H I | gc/ngc | | 1 | 1( | 560) | 1 | 561( 56) 2 |
| Fok I | ggatg | 9/13 | 1 | 1( | 508) | 2 | 509( 108) 2 |
| Gdi II | yggccg | -5/-1 | 1 | 1( | 561) | 1 | 562( 55) 2 |
| Gsu I | ctggag | 16/14 | 1 | 1( | 498) | 1 | 499( 118) 2 |
| HgiA I | gwgcw/c | | 1 | 1( | 470) | 1 | 471( 146) 2 |
| Hph I | ggtga | 8/7 | 1 | 1( | 271) | 2 | 272( 345) 1 |
| Mae I | c/tag | | 2 | 1( | 190) | 2 | 191( 426) 1 |
| Mbo II | gaaga | 8/7 | 1 | 1( | 533) | 1 | 534( 83) 2 |
| Nco I | c/catgg | | 2 | 1( | 267) | 2 | 268( 349) 1 |
| Nde I | ca/tatg | | 1 | 1( | 140) | 1 | 141( 476) 1 |
| NspB II | cmg/ckg | | 1 | 1( | 558) | 2 | 559( 58) 2 |
| Ple I | gagtc | 4/5 | 1 | 1( | 317) | 2 | 318( 299) 2 |
| Sac I | gagct/c | | 1 | 1( | 470) | 1 | 471( 146) 2 |
| Sac II | ccgc/gg | | 1 | 1( | 558) | 1 | 559( 58) 2 |
| SfaN I | gcatc | 5/9 | 1 | 1( | 274) | 2 | 275( 342) 2 |
| SnaB I | tac/gta | | 1 | 1( | 245) | 2 | 246( 371) 1 |
| Sty I | c/cwwgg | | 1 | 1( | 267) | 2 | 268( 349) 1 |
| Bcn H | ccs/gg | | 2 | 1( | 540) | 1 | 541( 24) 3 |
| Bgl H | gccnnnn/nggc | | 2 | 1( | 113) | 1 | 114( 441) 2 |
| BsmA I | gtctc | 1/5 | 2 | 1( | 336) | 1 | 337( 165) 3 |
| BstU I | cg/cg | | 2 | 1( | 559) | 2 | 560( 25) 3 |
| Dpn I | ga/tc | | 2 | 1( | 492) | 2 | 493( 56) 3 |
| Dsa I | c/crygg | | 2 | 1( | 267) | 1 | 268( 291) 1 |
| Hae III | gg/cc | | 2 | 1( | 183) | 2 | 184( 379) 1 |
| Hga I | gacgc | 5/10 | 2 | 1( | 424) | 1 | 425( 79) 3 |

| | |
|---|---|
| 565( 52) 2 | |
| 555( 62) 3 | |
| 502( 115) 3 | |
| 585( 32) 2 | |
| 549( 68) 2 | |
| 559( 58) 3 | |
| 563( 54) 3 | |
| 504( 113) 2 | |

FIG. 6A (CONTINUED)

| Enzyme | Site | | | | | | | |
|---|---|---|---|---|---|---|---|---|
| HinC II | gty/rac | 2 | 1( 25) 3 | 26( 396) 1 | 422( 195) 2 |
| Hinf I | g/antc | 2 | 1( 317) 1 | 318( 271) 2 | 589( 28) 3 |
| Hpa II | c/cgg | 2 | 1( 540) 1 | 541( 24) 3 | 565( 52) 2 |
| Mbo I | /gatc | 2 | 1( 492) 1 | 493( 56) 3 | 549( 68) 2 |
| Msp I | c/cgg | 2 | 1( 540) 1 | 541( 24) 3 | 565( 52) 2 |
| Nci I | cc/sgg | 2 | 1( 540) 1 | 541( 24) 3 | 565( 52) 2 |
| Nla III | catg/ | 2 | 1( 208) 2 | 209( 60) 3 | 269( 348) 1 |
| Nla IV | ggn/ncc | 2 | 1( 372) 1 | 373( 170) 2 | 543( 74) 3 |
| Sau3A I | /gatc | 2 | 1( 492) 1 | 493( 56) 3 | 549( 68) 2 |
| Sau96 I | g/gncc | 2 | 1( 183) 2 | 184( 360) 1 | 544( 73) 3 |
| Sec I | c/cnngg | 2 | 1( 267) 2 | 268( 291) 1 | 559( 58) 3 |
| Mae III | /gtnac | 3 | 1( 38) 4 | 39( 18) 3 | 57( 549) 1 |
| | | | 606( 11) | | |
| Mnl I | cctc | 7/7 | 1( 455) 1 | 456( 70) 2 | 526( 30) 4 |
| | | | 556( 61) 3 | | |
| ScrF I | cc/ngg | 3 | 1( 497) 1 | 498( 43) 3 | 541( 24) 4 |
| | | | 565( 52) 2 | | |
| Aat II | gacgt/c | 4 | 1( 28) 5 | 29( 53) 4 | 82( 83) 3 |
| | | | 165( 186) 2 | 351( 266) 1 | |
| Aha II | gr/cgyc | 5 | 1( 28) 6 | 29( 53) 5 | 82( 83) 4 |
| | | | 165( 186) 1 | 351( 153) 2 | 504( 113) 3 |
| | | | | 126( 80) 4 | 206( 33) 6 |
| | | | | 290( 157) 2 | 447( 170) 1 |
| Rsa I | gt/ac | 5 | 1( 125) 3 | | |
| | | | 239( 51) 5 | | |
| Mae II | a/cgt | 7 | 1( 29) 6 | 30( 12) 7 | 42( 41) 5 |
| | | | 83( 83) 3 | 166( 81) 4 | 247( 105) 2 |
| | | | 352( 257) 1 | 609( 8) 8 | |

98 sites found

No sites found for the following Restriction Endonucleases

| | | | | | |
|---|---|---|---|---|---|
| Acc I | gt/mkac | Dra III | cacnnn/gtg | Nsp7524 I | r/catgy |

FIG. 6A (CONTINUED)

| | | | | | |
|---|---|---|---|---|---|
| Afl II | c/ttaag | Drd I | gacnnnn/nngtc | NspH I | rcatg/y |
| Afl III | a/crygt | Ear I | ctcttc 1/4 | Pac I | ttaat/taa |
| AlwN I | cagnnn/ctg | Eco47 III | agc/gct | PaeR7 I | c/tcgag |
| Apa I | gggcc/c | Eco57 I | ctgaag 16/14 | PflM I | ccannnn/ntgg |
| ApaL I | g/tgcac | EcoN I | cctnn/nnagg | Pml I | cac/gtg |
| Ase I | at/taat | EcoO109 I | rg/gnccy | PpuM I | rg/gwccy |
| Asp718 | g/gtacc | EcoR I | g/aattc | Pst I | ctgca/g |
| Ava I | c/ycgrg | EcoR V | gat/atc | Pvu I | cgat/cg |
| Avr II | c/ctagg | Esp I | gc/tnagc | Pvu II | cag/ctg |
| BamH I | g/gatcc | Fsp I | tgc/gca | Rsr II | cg/gwccg |
| Bbe I | ggcgc/c | Hae I | wgg/ccw | Sal I | g/tcgac |
| Bbv I | gcagc 8/12 | Hae II | rgcgc/y | Sca I | agt/act |
| Bcl I | t/gatca | HgiE II | accnnnnnggt | Sfi I | ggccnnnn/nggcc |
| Bgl II | a/gatct 1/-1 | Hha I | gcg/c | Sma I | ccc/ggg |
| Bsm I | gaatgc | HinD III | a/agctt | Spe I | a/ctagt |
| BspH I | t/catga 4/8 | HinP I | g/cgc | Sph I | gcatg/c |
| BspM I | acctgc | Hpa I | gtt/aac | Spl I | c/gtacg |
| BspM II | t/ccgga | Kpn I | ggtac/c | Ssp I | aat/att |
| BssH II | g/cgcgc | Mlu I | a/cgcgt | Stu I | agg/cct |
| BstB I | tt/cgaa | Mme I | tccrac 20/18 | Taq I | t/cga |
| BstE II | g/gtnacc | Msc I | tgg/cca | Tth111 I | gacn/nngtc |
| BstX I | ccannnnn/ntgg | Mse I | t/taa | Tth111 II | caarca 11/9 |
| BstY I | r/gatcy | Nae I | gcc/ggc | Xba I | t/ctaga |
| Bsu36 I | cc/tnagg | Nar I | gg/cgcc | Xca I | gta/tac |
| Cfr10 I | r/ccggy | Nhe I | g/ctagc | Xho I | c/tcgag |
| Cla I | at/cgat | Not I | gc/ggccgc | Xcm I | ccannnn/nnnntgg |
| Dde I | c/tnag | Nru I | tcg/cga | Xma I | c/ccggg |
| Dra I | ttt/aaa | Nsi I | atgca/t | Xmn I | gaann/nnttc |

FIG. 6A
(CONTINUED)

*** Aligned sequences:
C1 ( 1f): |>u 1>++++++ ad169hcmv (930 bases)++++>u 930>|
C2 ( 1f): |>u 1>++++++ townehcmv (616 bases)++++>u 616>|

*** Alignment of first sequence with all others displayed
*** Key:
UPPER CASE = aligned non-identical bases
lower case = unaligned bases
----------- = aligned identical bases
............ = gap

```
ad169hcmv : AATCAATATATTGGCCATTAGCCATATATTATTCATTGGTTATATAGCATAAATCAATATTGGC
townehcmv : ................................................................

ad169hcmv : TATTGGCCATTGCATACGTTGTATCCATATCATAATATGTACATTTATATTGGCTCATGT
townehcmv : ............................................................

ad169hcmv : CCAACATTACCGCCATGTTGACATTGATTATTGACTAGTTATTAATAGTAATCAATTACG
townehcmv : ............................................................

ad169hcmv : GGGTCATTAGTTCATAGCCCATATATGGAGTTCCGCGTTACATAACTTACGGTAAATGGC
townehcmv : ............................................................

ad169hcmv : CCGCCTGGCTGACCGCCCAACGACCCCCGCCCATTGACGTCAATAATGACGTATGTTCCC
townehcmv : ...............................G.............G............

ad169hcmv : ATAGTAACGCCAATAGGGACTTTCCATTGACGTCAATGGGTGGAGTATTTACGGTAAACT
townehcmv : ------------------------------------------------------------
```

FIG. 6B

| ad169hcmv | : | GCCCACTTGGCAGTACATCAAGTGTATCATATGCCAAGTACGCCCCCTATTGACGTCAAT |
| townehcmv | : | ------------------------------------C----------------------- |

| ad169hcmv | : | GACGGTAAATGGCCCGCCTGGCATTATGCCCAGTACATGACCTTATGGGACTTTCCTACT |
| townehcmv | : | ---A--------------------------------------C---G------------- |

| ad169hcmv | : | TGGCAGTACATCTACGTATTAGTCATCGCTATTACCATGGTGATGCGGTTTTGGCAGTAC |
| townehcmv | : | ------------------------------*----------------------------- |

| ad169hcmv | : | ATCAATGGGCGTGGATAGCGGTTTGACTCACGGGGATTTCCAAGTCTCCACCCCATTGAC |
| townehcmv | : | -C---------------------------------------------------------- |

| ad169hcmv | : | GTCAATGGGAGTTTGTTTTGGCACCAAAATCAACGGGACTTTCCAAAATGTCGTAACAAC |
| townehcmv | : | ----------------------------------------------------T------- |

| ad169hcmv | : | TCCGCCCCATTGACGCAAATGGGCGGTAGGCGTGTACGGTGGGAGGTCTATATAAGCAGA |
| townehcmv | : | C-----G----------------------------------------------------- |

| ad169hcmv | : | GCTCGTTTAGTGAACCGTCAGATCGCCTGGAGACGCCATCCACGCTGTTTTGACCTCCAT |
| townehcmv | : | ------------------------------------------------------------ |

| ad169hcmv | : | AGAAGACACCGGGACCGATCCAGCCTCCGCGGCCGGGAACGGTGCATTGGAACGCGGATT |
| townehcmv | : | ------------------------------------------------------------ |

| ad169hcmv | : | CCCCGTGCCAAGAGTGACGTAAGTACCGCCTATAGAGTCTATAGGCCCACCCCCTTGGCT |
| townehcmv | : | ------------------------------------------------------------ |

| ad169hcmv | : | TCTTATGCATGCTATACTGTTTTTGGCTTG |
| townehcmv | : | ------------------------------ |

FIG. 6B
(CONTINUED)

| | | |
|---|---|---|
| LOCUS | HS5IEE | 930 bp ds-DNA VRL 15-SEP-1989 |
| DEFINITION | Human cytomegalovirus major immediate-early gene, enhancer. | |
| ACCESSION | K03104 | |
| KEYWORDS | major immediate-early gene. | |
| SOURCE | HCMV strain AD169. | |
| ORGANISM | Human cytomegalovirus<br>Viridae; ds-DNA enveloped viruses; Herpesviridae;<br>Betaherpesvirinae. | |
| REFERENCE | 1 (bases 1 to 930) | |
| AUTHORS | Boshart,M., Weber,F., Jahn,G., Dorsch-Haesler,K.,<br>Fleckenstein,B. and Schaffner,W. | |
| TITLE | A very strong enhancer is located upstream of an immediate<br>early gene of human cytomegalovirus | |
| JOURNAL | Cell 41, 521-530 (1985) | |
| STANDARD | full automatic | |
| REFERENCE | 2 (sites) | |
| AUTHORS | Zhang,X.-Y., Inamdar,N.M., Supakar,P.C., Wu,K., Ehrlich,M.<br>and Ehrlich,K.C. | |
| TITLE | three MDBP sites in the immediate-early enhancer-promoter<br>region of human cytomegalovirus | |
| JOURNAL | Virology 182, 865-869 (1991) | |
| STANDARD | full automatic | |
| COMMENT | Draft entry and printed copy of sequence in [1] were kindly<br>provided by M.Boshart, 24-OCT-1985.<br>The sequence shown is a 930 bp segment of the PstI m-fragment<br>from HCMV strain AD169. The enhancer region of the HCMV gene | |

FIG. 6B
(CONTINUED)

was defined by selecting for fragments of HCMV DNA that would
restore efficient growth of enhancerless SV40.

```
FEATURES              Location/Qualifiers
     misc_signal      214..620
                      /note="HCMV IE enhancer region"
     mRNA             738..>930
                      /note="HCMV IE mRNA"
BASE COUNT      233 A      228 C      211 G      258 T
ORIGIN     12 bp upstream of BalI site; .750 mu.
  1 AATCAATATT GGCCATTAGC CATATTATTC ATTGGTTATA TAGCATAAAT CAATATTGGC
 61 TATTGCCAT  TGCATACGTT GTATCCATAT CATAAATATGT ACATTTATAT TGGCTCATGT
121 CCAACATTAC CGCCATGTTG ACATTGATTA TTGACTAGTT ATTAATAGTA ATCAATTACG
181 GGGTCATTAG TTCATAGCCC ATATATGGAG TTCCGCGTTA CATAACTTAC GGTAAATGGC
241 CCGCCTGGCT GACCGCCCAA CGACCCCCGC CCATTGACGT CAATAATGAC GTATGTTCCC
301 ATAGTAACGC CAATAGGGAC TTTCCATTGA CGTCAATGGG TGGAGTATTT ACGGTAAACT
361 GCCCACTTGG CAGTACATCA AGTGTATCAT ATGCCAAGTA CGCCCCCTAT TGACGTCAAT
421 GACGGTAAAT GGCCCGCCTG GCATTATGCC CAGTACATGA CCTTATGGGA CTTTCCTACT
481 TGGCAGTACA TCTACGTATT AGTCATCGCT ATTACCATGG TGATGCGGTT TTGGCAGTAC
541 ATCAATGGGC GTGGATAGCG GTTTGACTCA CGGGGATTTC CAAGTCTCCA CCCCATTGAC
601 GTCAATGGGA GTTTGTTTTG GCACCAAAAT CAACGGGACT TTCCAAAATG TCGTAACAAC
661 TCCGCCCCAT TGACGCAAAT GGGCGGTAGG CGTGTACGGT GGGAGGTCTA TATAAGCAGA
721 GCTCGTTTAG TGAACCGTCA GATCGCCTGG AGACGCCATC CACGCTGTTT TGACCTCCAT
781 AGAAGACACC GGGACCGATC CAGCCTCCGC GGCCGGGAAC GGTGCATTGG AACGCGGATT
841 CCCCGTGCCA AGAGTGACGT AAGTACCGCC TATAGAGTCT ATAGGCCCAC CCCCTTGGCT
901 TCTTATGCAT TTTTGGCTTG
```

FIG. 6B
(CONTINUED)

```
LOCUS       HS5MIE1      616 bp ds-DNA              VRL       15-SEP-1989
DEFINITION  Human cytomegalovirus (Towne) major immediate-early (IE)
            gene, exon 1.
ACCESSION   K01484 K01090
KEYWORDS    major immediate-early gene.
SEGMENT     1 of 4
SOURCE      Human cytomegalovirus (strain Towne) passed in primary human
            foreskin fibroblasts, DNA [1], clone pXEP22 [2].
  ORGANISM  Human cytomegalovirus
            Viridae; ds-DNA enveloped viruses; Herpesviridae;
            Betaherpesvirinae.
REFERENCE   1  (bases 460 to 616)
  AUTHORS   Stenberg,R.M., Thomsen,D.R. and Stinski,M.F.
  TITLE     Structural analysis of the major immediate early gene of
            human cytomegalovirus
  JOURNAL   J. Virol. 49, 190-199 (1984)
  STANDARD  full automatic
REFERENCE   2  (bases 1 to 490)
  AUTHORS   Thomsen,D.R., Stenberg,R.M., Goins,W.F. and Stinski,M.F.
  TITLE     Promoter-regulatory region of the major immediate early gene
            of human cytomegalovirus
  JOURNAL   Proc. Natl. Acad. Sci. U.S.A. 81, 659-663 (1984)
  STANDARD  full automatic
```

FIG. 6B
(CONTINUED)

COMMENT    IE region 1 gene is also known as the major IE gene.
Cytomegalovirus immediate-early gene expression is dominated
in vivo by the expression of a single gene. At least three
promoters influence transcription of the virus after
infection. When a complete set of promoter-regulatory
regions were present (IE regions 1, 2 and 3 or IE region 1
and an adenovirus major late promoter), transcription was
qualitatively higher from IE region 1.

Based on these data, [1] proposes that the upstream sequence
of the IE region 1 gene competes more efficiently for RNA
polymerase II or other host cell proteins necessary for in
vitro transcription.

Consensus CAAT and TATA boxes were found at positions 429-433
and 462-467, a polyadenylation signal was found at positions
2198-2203.

Fourteen direct repeats were found in the promoter-regulatory
region (four 16-bp repeats, four 18-bp repeats, four 19-bp
repeats and two 21-bp repeats).

Draft entry and clean copy sequences [1], [2] kindly provided
by P.R. Witte and M.F. Stinski (10-FEB-1986).

FIG. 6B
(CONTINUED)

```
FEATURES             Location/Qualifiers
     prim_transcript 490..>616
                     /note="major IE mRNA"
     intron          611..>616
                     /note="major IE mRNA intron A"
BASE COUNT    144 A    165 C    162 G    145 T
ORIGIN      28 bp upstream of HincII site; 0.752 map units.
        1 GGCGACCGCC CAGCGACCCC CGCCCGTTGA CGTCAATAGT GACGTATGTT CCCATAGTAA
       61 CGCCAATAGG GACTTTCCAT GGGTGGAGTA TTTACGGTAA ACTGCCCACT
      121 TGGCAGTACA TCAAGTGTAT CATATGCCAA GTCCGCCCCC TATTGACGTC AATGACGGTA
      181 AATGGCCCGC CTAGCATTAT GCCCAGTACA TGACCTTACG GGAGTTTCCT ACTTGGCAGT
      241 ACATCTACGT ATTAGTCATC GCTATTACCA TGGTGATGCG GTTTTGGCAG TACACCAATG
      301 GGCGTGGATA GCGGTTTGAC TCACGGGGAT TTCCAAGTCT CCACCCCATT GACGTCAATG
      361 GGAGTTTGTT TTGGCACCAA AATCAACGGG ACTTTCCAAA ATGTCGTAAT AACCCCGCCC
      421 CGTTGACGCA AATGGGCGGT AGGCGTGTAC GGTGGGAGGT CTATATAAGCA GAGCTCGTTT
      481 AGTGAACCGT CAGATCGCCT GGAGACGCCA TCCACGCTGT TTTGACCTCC ATAGAAGACA
      541 CCGGGACCGA TCCAGCCTCC GCGGCCGGGA ACGGTGCATT GGAACGCGGA TTCCCCGTGC
      601 CAAGAGTGAC GTAAGT
```

FIG. 6B
(CONTINUED)

HCMV (AD169) -> Full Restriction Map

DNA sequence    930 b.p.    aatcaatattgg ... gtttttggcttg    linear

Positions of Restriction Endonucleases sites (unique sites underlined)

```
         Hae III                                                          Hae III
         Msc I                                                            Msc I
         Hae I                                                            Hae I
         Eae I                                     Ssp I                  Eae I                     Mae II
Ssp I    | |                                       |                      | |                      |
 |       | |                                       |                      | |                      |
 |       | |                  .                    |         .            | |          .           |
 5      10                                        52                     64                       76
        10                                                               64
        10                                                               64
        11                                                               65
AATCAATATATTGGCCATTAGCCATATATTATTCATTGGTTATATATAGCATAAATCAATATATTGGCTATTGGCCATTGCATACGTT
TTAGTTATATAACCGGTAATCGGTATATAATAAGTAACCAATATATCGTATTTAGTTATATAACCGATAACCGGTAACGTATGCAA

Mae I
                                Mme I           HinC II    Spe I
                     Rsa I      Nla III         Nla III    | |
                      |          | |              |        | |
         .            |   .      | |      .       |   .    | |    .        160
                     99         116            134       154
                                120            137       155
GTATCCATATCATAATATGTACATTTATATTGGCTCATGTCCAACATTACCGCCATGTTGACATTGATTATTGACTAGTT
CATAGGTATAGTATTATACATGTAAATATAACCGAGTACAGGTTGTAATGGCGGTACAACTGTAACTAATAACTGATCAA
```

FIG. 6C

```
                                                                                       Bgl I
                                                              Mae III                  Sau96 I
                                                              BstU I                   Hae III
         Mse I                                                  |                         |
         Age I                                                  |                         |  •   240
         ATTAATAGTAATCAATTACGGGGTCATTAGTTCATAGCCCATATATGGAGTTCCGCGTTACATAAACTTACGGTAAATGGC
         TAATTATCATTAGTTAATGCCCCCAGTAATCAAGTATCGGGTATATACCTCAAGGCGCAATGTATTGAATGCCATTTACCG
         ||                                                     | •                     | •  238
         161                                                    214                     238
         162                                                                             239

ScrF I                        Mae II
         EcoR II                       Aha II                                            Mae III
         BstN I                        Aat II                                              |
           |                             |      •                     •                    |    320
         CCGCCTGGCTGACCGCGCCCAACGACCCCCGCCCATTGACGTCAATAATGACGTATGTTCCCATAGTAACGCCAATAGGGAC
         GGCGGACCGACTGGCGCGGGTTGCTGGGGGCGGGTAACTGCAGTTATTACTGCATACAAGGGTATCATTGCGGTTATCCCTG
         ||                              ||                            |•                   |
         244                             276                           289                  304
         244                             276
         244                             277

Mae II                                                                         Nde I
         Aha II                                                    Bgl I       Rsa I      |    Rsa I
         Aat II                                                      |           |        |      |   400
         TTTCCATTGACGTCAATGGGTGGAGTATTTACGGTAAACTGCCCACTTGGCAGTACATCAAGTGTATCATATGCCAAGTA
         AAAGGTAACTGCAGTTACCCACCTCATAAATGCCATTTGACGGGTGAACCGTCATGTAGTTCACATAGTATACGGTTCAT
         ||                                                          |•           |•       |•  398
         329                                                         361          373      388
         329
         330

```
                                                              Alu I
                                                              Sac I
                                                              HgiA I
                              Mae II                          Bsp1286 I
            BsmA I            Aha II         Nla IV           Ban II
Ple I                         Aat II         Ban I
Hinf I
|           |                 |||            ||                  ||||
GTTTGACTCACGGGGGATTTCCAAGTCTCCACCCCATTGACGTCAATGGGAGTTTGTTTTGGCACCAAAATCAACGGGACT  640
CAAACTGAGTGCCCCCTAAAGGTTCAGAGGTGGGGTAACTGCAGTTACCCTCAAACAAAACCGTGGTTTTAGTTGCCCTGA
            |                 ||             |
            584               598            620
                              598            620
                              599

Mae III          Hga I              Rsa I    Mnl I
                                                                            719
          |                |                  |        |                    719
TTCCAAAAATGTCGTAACAACTCCGCCCCATTGACGCAAATGGGCGGTAGGCGTGTACGGTGGAGGTCTATATAAGCAGA  720
AAGGTTTTTACAGCATTGTTGAGGCGGGGGTAACTGCGTTTACCCGCCATCCGCACATGCCACCTCCAGATATATTCGTCT
          |                |                  |        |                    719
          653              672                694      703                  720

FIG. 6C
                          (CONTINUED)
```

```
                                                                                          Sau96 I
                                                                                          ScrF  I      Sau3A I
                                                                                          Nci I        Mbo   I
                                                                                          Msp I        Dpn   I
                                                                             Mbo II       Hpa II       Alw   II
                                                                             Bbv II       Bcn I   Ava  IV
                                        Mnl I                                             Nla  IV
                                                                                                                           789  797
                                                                                                                           789  797
GCTCGTTTAGTGAACCGTCAGATCGCCTGGAGACGCCATCCACGCTGTTTGACCTCCATAGAAGACACCGGACCGATC  800
CGAGCAAATCACTTGGCAGTCTAGCGGACCTCTGCGGTAGGTGCGACAAACTGGAGGTATCTTCTGTGGCCCTGGCTAG
                                                                                                                           789  797
                                                                                                                           789  797
                                                                                                         774      782      789
                                                                                                                  782              791   797
                                                                                                                                        792

792
```

Gsu I
ScrF I        Hga I
EcoR II       Aha II    Fok I
BstN I        BsmA I
Sau3A I
Mbo I
Dpn I
741
741       746
741       746    750
          746    752
          747    752    757

```
                                        Nla III
                                        Sph I
               BstX I                   NspH I
               Sau96 I  Sty I           Nsp7524 I
               Hae III  Sec I           Nsi I
ATAGGCCCACCCCCTTGGCTTCTTATGCATGCTATACTGTTTTTGGCTTG    930
TATCCGGGTGGGGGAACCGAAGAATACGTACGATATGACAAAACCGAAC
      |      |                 |  |||
      884    893               905 |||
      |      |                     907
      884    893                   907
         |                          908
         887
```

FIG. 6C
(CONTINUED)

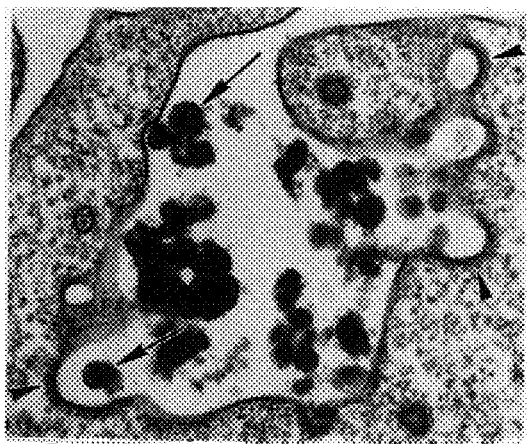
FIG. 7A
FIG. 7B
FIG. 7C
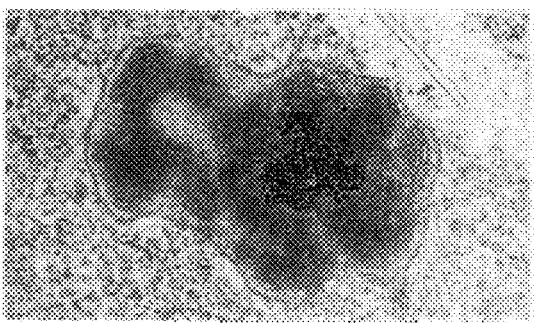
FIG. 7D
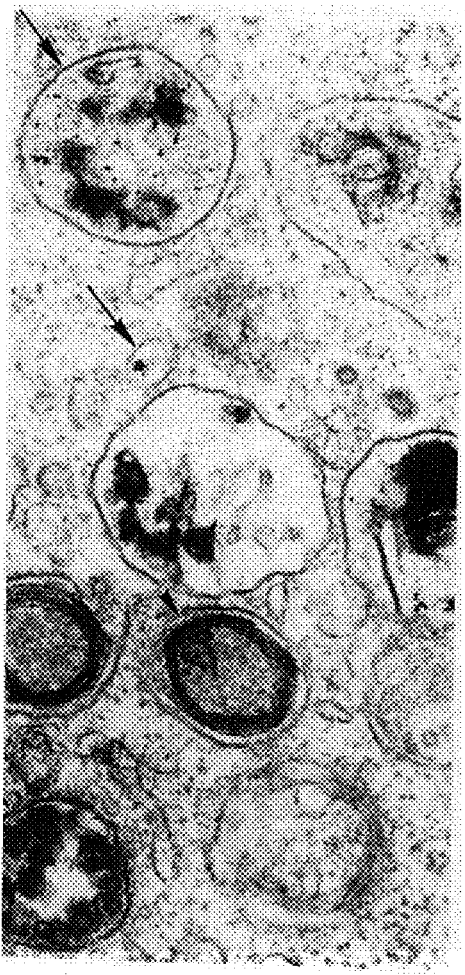
FIG. 7E
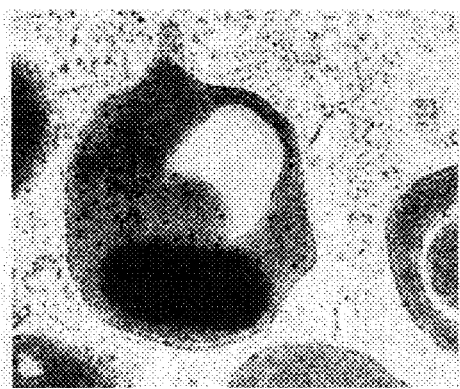
FIG. 7F

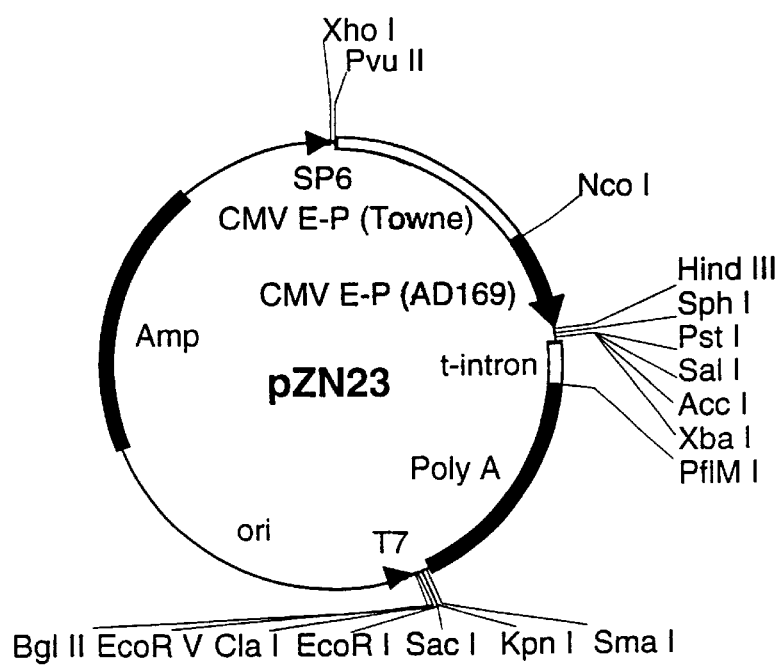
FIG. II

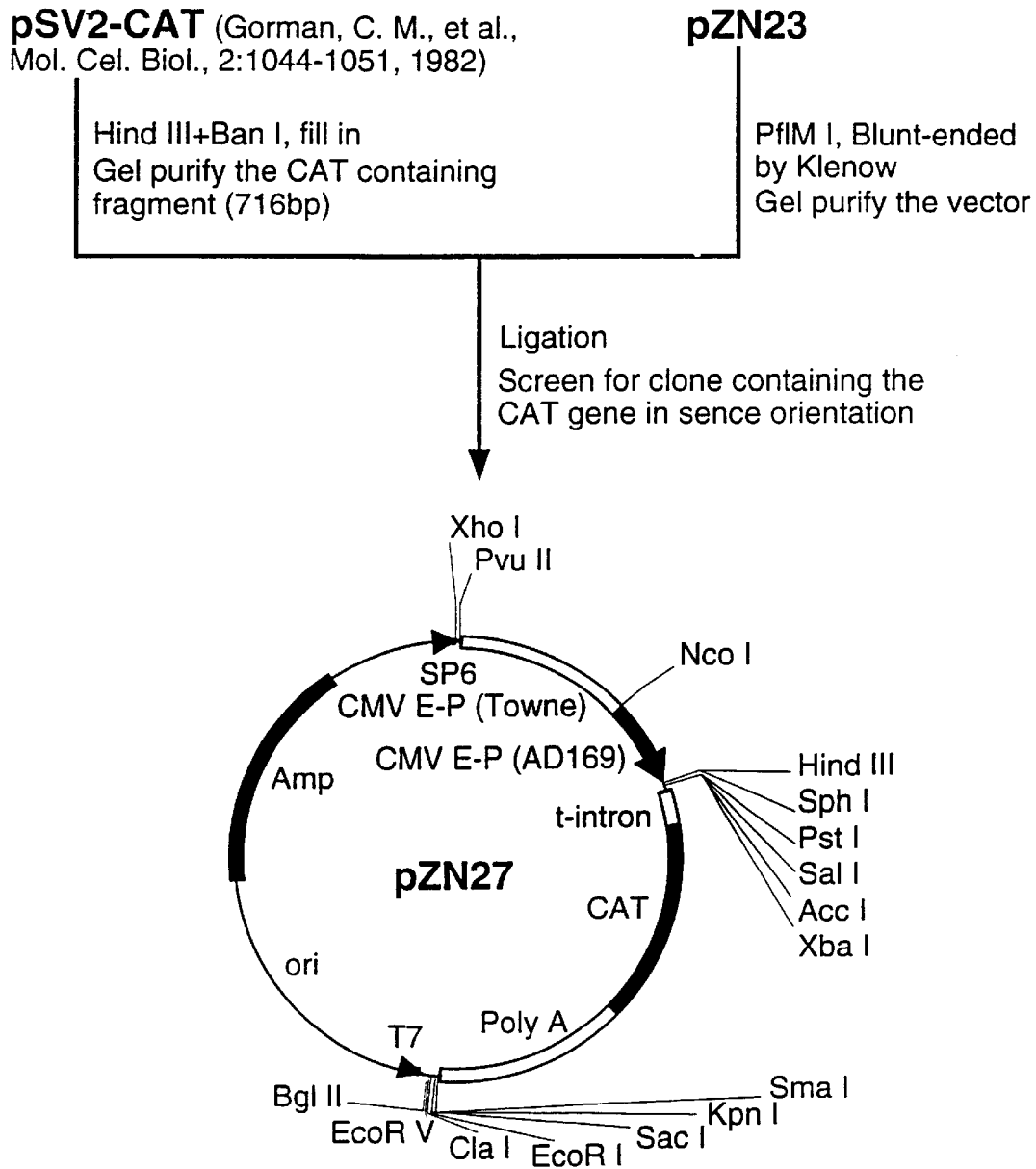
FIG. II
(CONTINUED)

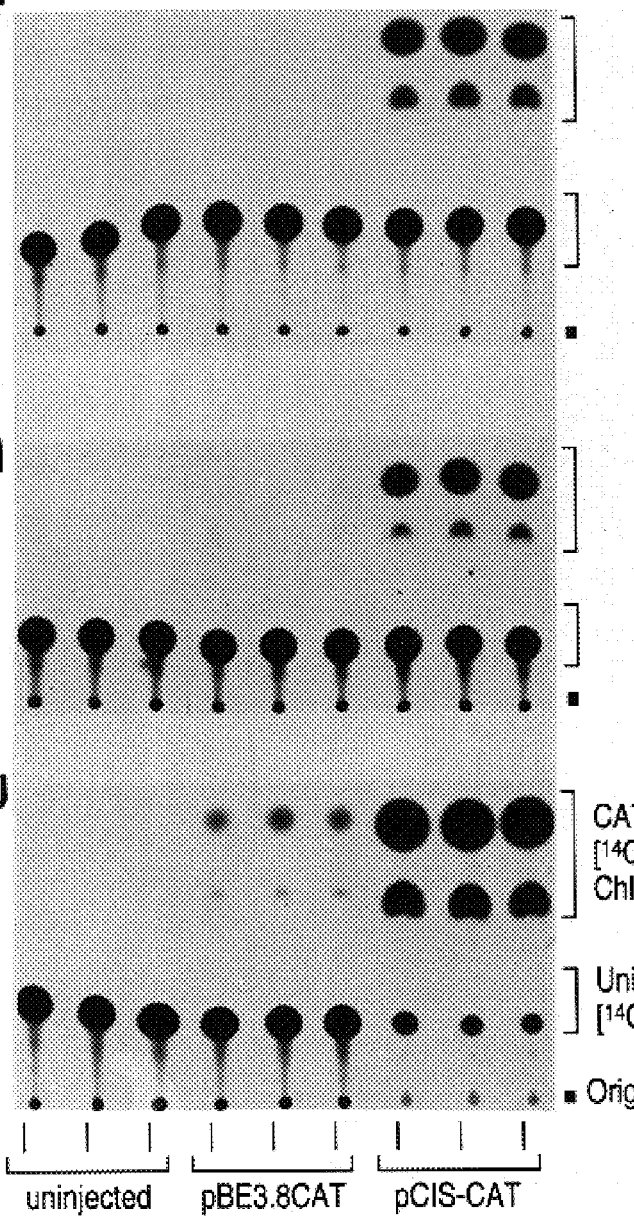

LN

Kidney

Liver

CAT Gene Product
[$^{14}$C acetyl-Chloramphenicols]

Unincorporated Label
[$^{14}$C Chloramphenicol]

■ Origin uninjected    pBE3.8CAT    pCIS-CAT

METHODS FOR COMPOSITIONS FOR IN VIVO GENE DELIVERY

CROSS-REFERENCE TO RELATED APPLICATIONS

This application is a continuation of U.S. Ser. No. 08/246,376 filed May 19, 1994, now U.S. Pat. No. 5,827,703, which is a continuation of U.S. Ser. No. 07/992,687 filed Dec. 17, 1992, now abandoned, which is a continuation in part of U.S. Ser. No. 07/927,200 filed Aug. 6, 1992, now abandoned, which is a continuation in part of U.S. Ser. No. 07/894,498 filed Jun. 4, 1992, now abandoned, which disclosures are hereby incorporated by reference.

INTRODUCTION

1. Technical Field

The present invention relates to methods and compositions for systemic introduction of exogenous genetic material into mammalian, particularly human, cells in vivo.

2. Background

An ever-expanding array of genes for which abnormal expression is associated with life-threatening human diseases is being cloned and identified. The ability to express such cloned genes in humans will ultimately permit the prevention and/or cure of many important human diseases, diseases which now are either poorly treated or are untreatable by currently available therapies. As an example, in vivo expression of cholesterol-regulating genes, genes which selectively block the replication of HIV, or tumor-suppressing genes in human patients should dramatically improve treatment of heart disease, HIV, and cancer, respectively. However, currently available gene delivery strategies have been unable to produce either a high level of or generalized transgene expression in vivo in a wide variety of tissues after systemic administration to a mammalian host. This inability has precluded the development of effective gene therapy for most human diseases.

Approaches to gene therapy include both different goals and different means of achieving those goals. The goals include gene replacement, gene correction and gene augmentation. In gene replacement, a mutant gene sequence is specifically removed from the genome and replaced with a normal, functional gene. In gene correction, a mutant gene sequence is corrected without any additional changes in the target genome. In gene augmentation, the expression of mutant genes in defective cells is modified by introducing foreign normal genetic sequences.

The means to reach the above goals include "ex vivo" transfection of a target cell, followed by introduction of the transformed cells into a suitable organ in the host mammal. Ex vivo techniques include transfection of cells in vitro with either naked DNA or DNA encapsulated in liposomes, followed by introduction into a host organ ("ex vivo" gene therapy). The criteria for a suitable organ include that the target organ for implantation is the site of the relevant disease, the disease is easily accessible, that it can be manipulated in vitro, that it is susceptible to genetic modification methods and ideally, it should contain either non-replicating cells or cycling stem cells to perpetuate a genetic correction. Further, it should be possible to reimplant the genetically modified cells into the organism in a functional and stable form. A further requirement for ex vivo gene therapy, if for example a retroviral vector is used, is that the cells be pre-mitotic; post-mitotic cells are refractory to infection with retroviral vectors. Exemplary of a target organ which meets the criteria of in vitro gene transfer is the mammalian bone marrow. There are also several drawbacks to ex vivo therapy; for example, if only differentiated, replicating cells are infected, the newly introduced gene function will be lost as those cells mature and die. Ex vivo approaches also can be used to transfect only a limited number of cells and cannot be used to transfect cells which are not first removed from the body. The above methods involve integration of new genetic material into the cell genome and thus constitute permanent changes to the host genome. However, some gene augmentation can be achieved using methods which do not involve changes to the genome, but which introduce DNA into a host cell where it is maintained primarily in an extrachromosomal or episomal form.

Liposomes (more broadly defined as lipid carriers) have been used effectively, particularly to introduce drugs, radiotherapeutic agents, enzymes, viruses, transcription factors and other cellular effectors into a variety of cultured cell lines and animals. In addition, successful clinical trials examining the effectiveness of liposome-mediated drug delivery have been completed. Several strategies have been devised to increase the effectiveness of liposome-mediated drug delivery by targeting liposomes to specific tissues and specific cell types. However, while the basic methodology for using liposome-mediated vectors is well developed, the technique has not been perfected for liposome-based transfection vectors for in vivo gene therapy. In the studies published to date, injection of the vectors either intravenously, intratracheally or into specific tissues has resulted in low but demonstrable expression, but the expression has generally been limited to one tissue, typically either the tissue that was injected (for example muscle); liver or lung where iv injection has been used; or lung where intratracheal injection has been used, and less than 1% of all cells within these tissues were transfected.

In vivo expression of transgenes has been restricted to injection of transgenes directly into a specific tissue, such as direct intratracheal, intramuscular or intraarterial injection of naked DNA or of DNA-cationic liposome complexes, or to ex vivo transfection of host cells, with subsequent reinfusion. Currently available gene delivery strategies consistently have failed to produce a high level and/or generalized transgene expression in vivo. It would therefore be of interest to develop compositions and delivery methods for in vivo gene therapy that provide for a high level of expression of the transgene and/or expression in a variety of cell and tissue types for the in vivo treatment, prevention, or palliation of numerous human diseases.

Relevant Literature

A large number of publications relate to in vivo and ex vivo transfection of mammals. In some cases, only transcription of a transgene has been achieved, in others, the data appear to show only a low level of expression and/or expression in a limited number of tissues or cell types. The following are examples of the publications in this area.

Multiple approaches for introducing functional new genetic material into cells, both in vitro and in vivo have been attempted (Friedmann (1989) *Science*, 244:1275–1280). These approaches include integration of the gene to be expressed into modified retroviruses (Friedmann (1989) supra; Rosenberg (1991) *Cancer Research* 51(18), suppl.: 5074S–5079S); integration into non-retrovirus vectors (Rosenfeld, et al. (1992) *Cell*, 68:143–155; Rosenfeld, et al. (1991) *Science*, 252:431–434); or delivery of a transgene linked to a heterologous promoter-enhancer element via liposomes (Friedmann (1989), supra; Brigham, et al. (1989) *Am. J. Med. Sci.*, 298:278–281; Nabel, et al. (1990) *Science*, 249:1285–1288; Hazinski, et al. (1991) *Am. J. Resp. Cell Molec. Biol.*, 4:206–209; and Wang and Huang (1987) *Proc. Natl. Acad. Sci.* (*USA*), 84:7851–7855); coupled to ligand-specific, cation-based transport systems (Wu and Wu (1988) *J. Biol. Chem.*, 263:14621–14624) or the use of naked DNA, expression vectors (Nabel et al. (1990), supra); Wolff et al. (1990) *Science*, 247:1465–1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (*Am. J. Med. Sci.* (1989) 298:278–281 and *Clinical Research* (1991) 39 (abstract)) have reported in vivo transfection only of lungs of mice following either intravenous or intratracheal administration of a DNA liposome complex. An example of a review article of human gene therapy procedures is: Anderson, *Science* (1992) 256:808–813.

PCT/US90/01515 (Felgner et al.) is directed to methods for delivering a gene coding for a pharmaceutical or immunogenic polypeptide to the interior of a cell of a vertebrate in vivo. Expression of the transgenes is limited to the tissue of injection. PCT/US90/05993 (Brigham) is directed to a method for obtaining expression of a transgene in mammalian lung cells following either iv or intratracheal injection of an expression construct. PCT 89/02469 and PCT 90/06997 are directed to ex vivo gene therapy, which is limited to expressing a transgene in cells that can be taken out of the body such as lymphocytes. PCT 89/12109 is likewise directed to ex vivo gene therapy. PCT 90/12878 is directed to an enhancer which provides a high level of expression both in transformed cell lines and in transgenic mice using ex vivo transfection.

SUMMARY OF THE INVENTION

Methods and compositions are provided for introduction of a transgene into a plurality of mammalian tissues in vivo. The method includes the step of incorporating a transfection cassette comprising a nucleotide sequence of interest into a largely non-integrating plasmid and introducing the plasmid into a mammalian host, other than by directly introducing it into a specific tissue. The plasmid may be naked nucleic acid, or nucleic acid complexed to a lipid carrier such as cationic liposomes. The method finds use to modulate the genotype and/or the phenotype of mammalian cells, particularly in vivo gene therapy. The modulation may be generalized, i.e. obtained in a multiplicity of cell types or tissues, or the modulation may be selective, for example inducible and/or in only selected cell or tissue types.

DESCRIPTION OF THE DRAWINGS

The patent or application file contains at least one drawing executed in color. Copies of this patent or patent application publication with color drawing(s) will be provided by the Office upon request and payment of the necessary fee.

In FIG. 4A is shown a phase contrast micrograph of freshly isolated human CD4$^+$ T lymphocytes 48 hours after transfection. FIG. 4B shows a fluorescence micrograph which demonstrates that essentially 100% of the T lymphocytes stain positively for CAT protein, i.e., they have been transfected.

FIGS. 6A–6C show a full restriction map of the immediate early enhancer and promoter region of HCMV (Towne) in FIG. 6A and HCMV(AD169) in FIG. 6C. FIG. 6B show a sequence comparison of the two HCMV promoters. The sequence of the Towne strain is designated as hs5miel on this comparison. The position of the NcoI site is indicated by an asterisk.

FIG. 7 shows an electron micrograph which demonstrates that cationic lipid carrier: DNA complexes (DOTMA:DOPE:pRSV-CAT) are internalized by cells via classical receptor-mediated endocytosis following binding to cell surface receptors. Lipid carriers were 1:1 DOTMA:DOPE. 20 µg DNA was complexed with 20 nmoles cationic lipid.

FIG. 9A shows analysis of lung, spleen, liver and heart two days following iv injection with either lipid carrier alone (lanes 1–4) or lipid carrier plus DNA (lanes 5–8); FIG. 9B shows the results at six days, following iv injection, in mouse lung, spleen, liver and heart (lanes as in 9A). The lipid carrier was DOTMA:DOPE 1 to 1 molar ratio. Cationic lipid to DNA ratio was 4 nanomoles to 1 $\mu$g. 100 $\mu$g DNA was injected per mouse. In both figures the chromatograph runs from bottom to top.

FIG. 10C shows that in tissue from B16 melanoma-bearing mice which did not receive an injection of DNA-lipid carrier complexes, no CAT activity is present in the surrounding normal lung or in any of the lung tumor cells.

FIG. 11 shows the construction of plasmid pZN27.

FIGS. 17A, 17C, and 17E are lung sections from control mice at 50×, 100×, and 250× magnification, respectively. FIGS. 17B and 17D are lung sections from control mice at 50× and 100× magnification. Lipid carriers were 1 to 1 molar DDAB:Cholesterol (SUV). Lipid carrier-DNA complexes were 5 nanomoles cationic lipid to 1 $\mu$g DNA. 100 $\mu$g DNA was injected per mouse.

FIG. 19A shows the construction of intermediate plasmids pZN52, pZN54, pZN56 and pZN58. FIG. 19B shows the construction of the final plasmids, pZN60 through pZN63, from the intermediates.

FIGS. 21A–21K show an autoradiograph of the thin layer chromatograph of CAT activity in heart (21F), lymph nodes (21G), spleen (21H), kidney (21I), lung (21J), and liver (21K) in tissue from uninjected mice (lanes 1–3), mice injected IV with pBE3.8CAT (lanes 4–6), or mice injected with pCIS.CAT (lanes 7–9). Lipid carriers were DDAB:Cholesterol, 1:1 SUV (1 microgram DNA to 5 nmoles cationic lipid); 100 micrograms injected per mouse.

DESCRIPTION OF THE SPECIFIC EMBODIMENTS

Figure 1A:
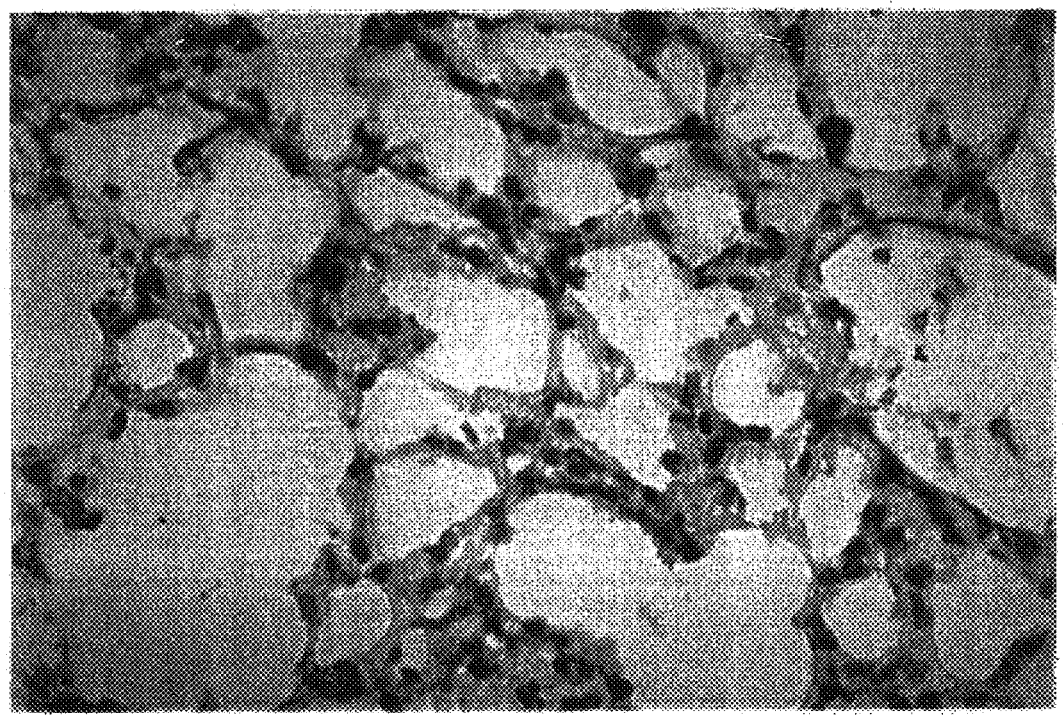
FIGS. 1A and 1B show photomicrographs of sections of mouse lung (A) from a mouse injected with a transfection cassette, or (B) a control mouse. The photomicrograph in (A) shows a section of mouse lung 48 hours following iv injection of PZN27:DDAB:Chol expression vector-cationic lipid carrier complexes. The lipid carrier composition was 1:1 molar DDAB:Chol. The carrier: plasmid ratio was 5 nanomoles cationic lipid to 1 µg DNA. A dose of 100 µg DNA was injected per mouse. This field shows alveoli and alveolar lining cells, the majority (50–70%) of which stain positively for the presence of CAT protein when probed with anti-CAT antibody and visualized using alkaline phosphatase. The treated animals' lungs stain uniformly with diffuse involvement of alveolar and vascular endothelial cells. Airway epithelial staining is also seen indicating airway cells are also transfected. The CAT (chloramphenicol acetyl transferase) protein normally is not present in mammalian cells and therefore the presence of CAT protein in these cells indicates that they have been transfected in vivo. The photomicrograph in (B) shows a section of mouse lung from a control animal treated with iv-injected lipid carrier only, and probed with anti-CAT antibody. Cells do not show significant staining, although low-level background staining is detectable in some alveolar macrophages, which possess endogenous alkaline phosphatase activity.

In accordance with the subject invention, nucleic acid constructs together with methods of preparation and use are provided which allow for in vivo change of genotype and/or modulation of phenotype of cells in a plurality of tissues of a mammalian host, following introduction of the constructs into a circulating body fluid at a sufficient dose to cause transfection of tissues and cells contacted by the nucleic acid. The tissues which are transformed include the lungs, heart, liver, bone marrow, spleen, lymph nodes, kidneys, thymus, skeletal muscle, ovary, uterus, stomach, small intestine, colon, pancreas, and brain in normal animals, as well as metastatic tumors and intravascular tumor emboli in tumor-bearing mammals. Particular cells which are transfected include macrophages, alveolar type I and type II cells, hepatocytes, airway epithelial cells, vascular endothelial cells, cardiac myocytes, myeloblasts, erythroblasts, B-lymphocytes and T-lymphocytes. The circulating bodily fluid is generally blood, but intrathecal administration can also be used.

The constructs may be either naked nucleic acid or associated with a lipid carrier. The amount of transfection desired is that which will result in a therapeutic effect, i.e. prevention, palliation, and/or cure of an animal or human disease ("in vivo" gene therapy). Optionally, the lipid carrier molecule and/or construct may provide for targeting and/or expression in a particular cell type or types. The nucleic acid constructs may be prepared from nucleic acid sequences which are synthetic, naturally derived or a combination thereof. The sequences can be obtained from a donor host homologous with an intended recipient host, or depending upon the nature of the nucleic acid sequence it may be desirable to synthesize the sequence with host preferred codons. The host preferred codons may be determined from the codons of highest frequency in the proteins expressed in the largest amount in the particular host of interest. Where the intended use is to treat disease resulting from an infectious organism, an appropriate source of sequence may be viral nucleic acid, either RNA or DNA. Transfection of multiple tissues and cells other than those solely at or afferent to the site of introduction of the nucleic acid constructs into the host is obtained and expression is at a vastly higher level and in a dramatically greater number of cells and cell types than previously has been reported. Many of these tissues and cell types have not been transfected previously in adults by any in vivo gene transfer approach.

Genes are high molecular weight, polyanionic molecules, for which carrier-mediated delivery is usually but not always required for DNA transfection of cells either in culture or in vivo. Cationic lipid carriers such as liposomes have been used to deliver transcriptional regulatory proteins. Further, liposomes themselves (unlike viral vectors) appear to be non-immunogenic in vivo. Liposome formulations, including those containing a cationic lipid, have been shown to be safe and well tolerated in human patients (Treat et al., *J. Natl. Cancer Instit.* (1990) 82:1706). Although a wide variety of transfection techniques can produce high level expression of transgenes in cultured cells, only a few such methods, including those using liposomes, are compatible with in vivo gene delivery. Previous attempts at using either cationic liposomes or naked DNA to obtain in vivo transfection have resulted in transfection of a single tissue and/or transfection only of the tissue of introduction of exogenous DNA. This pattern of transfection suggests that other than being taken up by normal cellular mechanisms, cells in the tissue of introduction are damaged by the introduction method and are then able to take up some of the exogenous DNA which has been introduced.

Applicants surprisingly discovered changes which provide for both transfection of a wide variety of tissues and cell types and a high-level of transgene expression after systemic administration into a mammalian host. These changes include the use of DNA:cationic lipid carrier complexes, wherein the ratio of DNA to cationic lipid in the lipid carrier can significantly affect obtaining of in vivo expression; use of a higher dose of complexes than has been used previously; use of an appropriate promoter element, for example which is both strong and constitutively active, such as the HCMV-1E1 element where it is desired to provide enhanced expression in a wide variety of cell types in vivo; and placement of greater than 100 bp of an intron 5' to the coding region of the transgene or removal of the intron altogether to facilitate production of a desired gene product. Additionally, it has surprisingly been discovered that a number of tissues, including the lung, liver, spleen, kidney, lymph nodes and heart can be transformed following direct administration of high doses of naked DNA into a circulating body fluid, such as blood or cerebral spinal fluid. Alternatively, selective expression can be obtained in specific cell and tissue types and at a desired time (i.e., expression is inducible) by alterations in the components, particularly promoters and/or enhancers of the constructs used, or by the use of targeting moieties on the liposomes.

Most gene therapy strategies have relied on transgene insertion into retroviral or DNA virus vectors. Potential disadvantages of retroviruses, as compared to the use of naked DNA or the use of cationic lipid carriers, include the limited ability of retroviruses to mediate in vivo (as opposed to ex vivo) transgene expression; the inability of retrovirus vectors to transfect non-dividing cells; possible recombination events in replication-defective retrovirus vectors, resulting in infectious retroviruses; possible activation of oncogenes or inhibition of tumor suppressor genes due to the random insertion of the transgene into host cell genomic DNA; size limitations: less than 15 kb of DNA typically can be packaged in a retrovirus vector; and potential immunogenicity, leading to a host immune response against the vector. In addition, all ex vivo approaches require that the cells be removed from the body and that they be maintained in culture for a period of time. While in culture, cells may undergo deleterious or potentially dangerous phenotypic and/or genotypic changes.

Adenovirus and other DNA viral vectors share several of the above potential limitations. Thus, the subject invention has several advantages over existing techniques, including ease of administration and the results achieved. The components of the transfection vector generally will include as operably linked components in the direction of transcription, a transcriptional initiation region, a DNA sequence of interest and a transcriptional termination region, wherein the transcriptional regulatory regions are functional in the host mammal's cells that are targeted for transfection. Optionally, an intron may be included in the construct, preferably 5' to the coding sequence. Generally, the construct does not become integrated into the host cell genome and is introduced into the host as part of a non-integrating plasmid.

In some cases, it may be desirable to use constructs that produce long term transgene effects in vivo, either by integration of the transgene into host cell genomic DNA at high levels or by persistence of the transgene in the nucleus of cells in vivo in stable, episomal form. Integration of the transgene into genomic DNA of host cells in vivo may be facilitated by administering the transgene in a linearized form (either the coding region alone, or the coding region together with 5' and 3' regulatory sequences, but without any plasmid sequences present). It may be possible to further increase the incidence of transgene integration into genomic DNA by incorporating a purified retroviral enzyme, such as the HIV-1 integrase enzyme, into the lipid carrier-DNA complex. Appropriate flanking sequences are placed at the 5' and 3' ends of the transgene DNA. These flanking sequences have been shown to mediate integration of the HIV-1 DNA into host cell genomic DNA in the presence of HIV-1 integrase. Alternatively, duration of transgene expression in vivo can be prolonged by the use of constructs that contain non-transforming sequences of a virus such as Epstein-Barr virus, and sequences such as oriP and EBNA-1, which appear to be sufficient to allow heterologous DNA to be replicated as a plasmid in mammalian cells (Buhans, et al., *Cell* (1986) 62:955).

The constructs for use in the invention include several forms, depending upon the intended use of the construct. Thus, the constructs include vectors, transcriptional cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

For the transcriptional initiation region, or promoter element, any region may be used with the proviso that it provides the desired level of transcription of the DNA sequence of interest. The transcriptional initiation region may be native to or homologous to the host cell, and/or to the DNA sequence to be transcribed, or foreign or heterologous to the host cell and/or the DNA sequence to be transcribed. By foreign to the host cell is intended that the transcriptional initiation region is not found in the host into which the construct comprising the transcriptional initiation region is to be inserted. By foreign to the DNA sequence is intended a transcriptional initiation region that is not normally associated with the DNA sequence of interest. Efficient promoter elements for transcription initiation include the SV40 (simian virus 40) early promoter, the RSV (Rous sarcoma virus) promoter, the Adenovirus major late promoter, and the human CMV (cytomegalovirus) immediate early 1 promoter.

Inducible promoters also find use with the subject invention where it is desired to control the timing of transcription. Examples of promoters include those obtained from a .beta.-interferon gene, a heat shock gene, a metallothionein gene or those obtained from steroid hormone-responsive genes, including insect genes such as that encoding the ecdysone receptor. Such inducible promoters can be used to regulate transcription of the transgene by the use of external stimuli such as interferon or glucocorticoids. Since the arrangement of eukaryotic promoter elements is highly flexible, combinations of constitutive and inducible elements also can be used. Tandem arrays of two or more inducible promoter elements may increase the level of induction above baseline levels of transcription which can be achieved when compared to the level of induction above baseline which can be achieved with a single inducible element.

Generally, the regulatory sequence comprises DNA up to about 1.5 Kb 5' of the transcriptional start of a gene, but can be significantly smaller. This regulatory sequence may be modified at the position corresponding to the first codon of the desired protein by site-directed mutagenesis (Kunkel T A, 1985, *Proc. Natl. Acad. Sci.* (*USA*), 82:488–492) or by introduction of a convenient linker oligonucleotide by ligation, if a suitable restriction site is found near the N-terminal codon. In the ideal embodiment, a coding sequence with a compatible restriction site may be ligated at the position corresponding to codon #1 of the gene. This substitution may be inserted in such a way that it completely replaces the native coding sequence and thus the substituted sequence is flanked at its 3' end by the gene terminator and polyadenylation signal.

Transcriptional enhancer elements optionally may be included in the expression cassette. By transcriptional enhancer elements is intended DNA sequences which are primary regulators of transcriptional activity and which can act to increase transcription from a promoter element, and generally do not have to be in the 5' orientation with respect to the promoter in order to enhance transcriptional activity. The combination of promoter and enhancer element(s) used in a particular expression cassette can be selected by one skilled in the art to maximize specific effects. Different enhancer elements can be used to produce a desired level of transgene expression in a wide variety of tissue and cell types. For example, the human CMV immediate early promoter-enhancer element can be used to produce high level transgene expression in many different tissues in vivo.

Examples of other enhancer elements which confer a high level of transcription on linked genes in a number of different cell types from many species include enhancers from SV40 and RSV-LTR. The SV40 and RSV-LTR are essentially constitutive. They may be combined with other enhancers which have specific effects, or the specific enhancers may be used alone. Thus, where specific control of transcription is desired, efficient enhancer elements that are active only in a tissue-, developmental-, or cell-specific fashion include immunoglobulin, interleukin-2 (IL-2) and β-globin enhancers are of interest. Tissue-, developmental-, or cell-specific enhancers can be used to obtain transgene expression in particular cell types, such as B-lymphocytes and T-lymphocytes, as well as myeloid, or erythroid progenitor cells. Alternatively, a tissue-specific promoter such as that derived from the human cystic fibrosis transmembrane conductance regulator (CFTR) gene can be fused to a very active, heterologous enhancer element, such as the SV40 enhancer, in order to confer both a high level of transcription and tissue-specific transgene transcription. In addition, the use of tissue-specific promoters, such as LCK, may allow targeting of transgene transcription to T lymphocytes. Tissue specific transcription of the transgene may be important, particularly in cases where the results of transcription of the transgene in tissues other than the target tissue would be deleterious.

Tandem repeats of two or more enhancer elements or combinations of enhancer elements may significantly increase transgene expression when compared to the use of a single copy of an enhancer element; hence enhancer elements find use in the expression cassette. The use of two different enhancer elements from the same or different sources flanking or within a single promoter can in some cases produce transgene expression in each tissue in which each individual enhancer acting alone would have an effect, thereby increasing the number of tissues in which transcription is obtained. In other cases, the presence of two different enhancer elements results in silencing of the enhancer effects. Evaluation of particular combinations of enhancer elements for a particular desired effect or tissue of expression is within the level of skill in the art.

Although generally it is not necessary to include an intron in the expression cassette, an intron comprising a 5' splice site (donor site) and a 3' splice site (acceptor site) separated by a sufficient intervening sequence to produce high level, extended in vivo expression of a transgene administered iv or ip can optionally be included. Generally, an intervening sequence of about 100 bp produces the desired expression pattern and/or level, but the size of the sequence can be varied as needed to achieve a desired result. The optional intron placed 5' to the coding sequence results in high level extended in vivo expression of a transgene administered iv or ip but generally is not necessary to obtain expression. Optimally, the 5' intron specifically lacks cryptic splice sites which result in aberrantly spliced mRNA sequences. If used, the intron splice donor and splice acceptor sites, arranged from 5' to 3' respectively, are placed between the transcription initiation site and the translational start codon as diagrammed in (1), below.

with the proviso that where the coding sequence encodes a polypeptide of interest, it should lack cryptic splice sites which can block production of appropriate mRNA molecules and/or produce aberrantly spliced or abnormal mRNA molecules. The nucleic acid sequence may be DNA; it also may be a sequence complementary to a genomic sequence, where the genomic sequence may be one or more of an open reading frame, an intron, a non-coding leader sequence, or any other sequence where the complementary sequence will inhibit transcription, messenger RNA processing, for example splicing, or translation.

A number of nucleic acid sequences are of interest for use in vivo gene therapy. Where the nucleic acid codes for a polypeptide, the polypeptide may be one which is active intracellularly, a transmembrane protein, or it may be a secreted protein. It may also code for a mutant protein, for example, which is normally secreted, but which has been altered act intracellularly. The nucleic acid may also be a DNA sequences coding for mRNA (antisense or ribozyme sequences such as those to HIV-REV or BCR-ABL sequences) or for proteins such as transdominant negative mutants which specifically prevent the integration of HIV genes into the host cell genomic DNA, replication of HIV sequences, translation of HIV proteins, processing of HIV mRNA or virus packaging in human cells; the LDL (low density lipoprotein) receptor, which specifically lowers serum cholesterol, and which can reduce the risk of heart attack in individuals with elevated serum cholesterol levels, and proteins such as granulocyte macrophage colony stimulating factor (GM-CSF) which can stimulate the production of white blood cells from the bone marrow of immunocom-

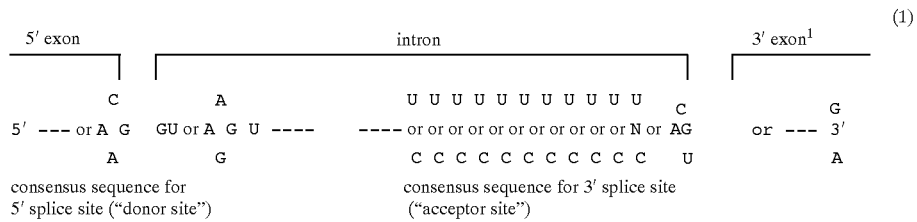

(1)

Consensus sequences for the 5' and 3' splice sites used in RNA splicing

[1] The sequence given is that for the RNA chain; the nearly invariant GU and AG dinucleotides at either end of the intron are shaded.

Alternatively, the intervening sequence may be placed 3' to the translational stop codon and the transcriptional terminator or inside the coding region. The intron can be a hybrid intron with an intervening sequence or an intron taken from a genomic coding sequence. An intron 3' to the coding region, particularly one of less than 100 bp, or any intron which contains cryptic splice sites may under certain condition substantially reduce the level of transgene expression produced in vivo. However, unexpectedly, a high level of in vivo expression of a transgene can be achieved using a vector that lacks an intron. Such vectors therefore are of particular interest for in vivo transfection.

Downstream from and under control of the transcriptional initiation regulatory regions is a multiple cloning site for insertion of a nucleic acid sequence of interest which will provide for one or more alterations of host genotype and modulation of host phenotype. Conveniently, the multiple cloning site may be employed for a variety of nucleic acid sequences in an efficient manner. The nucleic acid sequence inserted in the cloning site may have any open reading frame encoding a polypeptide of interest, for example, an enzyme, promised patients and produce significant anti-tumor activity or cystic fibrosis transmembrane conductance regulator (CFTR) for the treatment of cystic fibrosis. These, or other beneficial (therapeutic) nucleic acid sequences can be expressed in appropriate cells in vivo using this invention. Examples of beneficial therapeutic nucleic acid sequences are those encoding molecules have superoxide dismutase activity or catalase activity to protect the lung from oxidant injury; endothelial prostaglandin synthase to produce prostacyclin and prostaglandin E2; and antiprotease alpha-1 antitrypsin. Thus, this approach could dramatically improve the treatment of acquired immune deficiency syndrome (AIDS), cystic fibrosis, cancer, heart disease, autoimmune diseases and a variety of life threatening infections. For the treatment AIDS, anti-TAT, REV, TAR or other critical anti-HIV sequences may be used, particularly for expression of the appropriate coding sequences in T lymphocytes, macrophages and monocytes which can be achieved following iv administration of the appropriate coding sequences; expression of wild-type CFTR gene in the lungs of cystic fibrosis patients (see Collins, *Science* (1992) 256:774–783) CFTR cDNA can be obtained from Dr. Collins at University of Michigan or Dr. Tsui at Toronto Sick Children's Hospital; expression of wild-type p53 in tumors of cancer patients with absent or aberrant expression of this gene, p53 is obtainable from Dr. Vogelstein at John Hopkins Univ; antisense sequences to over-expressed, transforming oncogenes, such as myc or ras in tumors; genes which block activity of activated T cell clones which attack myelin in multiple sclerosis or other targets in autoimmune diseases. A T-cell lymphocyte clone activated to recognize and attack myelin can be targeted by using an anti-sense sequence, ribozyme sequence or transgene coding for a transdominant negative mutant which specifically blocks surface expression on the T-cell of T-cell receptor components which mediate recognition and/or attack of myelin-sheathed cells.

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Adenylation residues, preferably more than 32 and up to 200 or more as necessary may be included in order to stabilize the mRNA. Alternatively, a terminator and polyadenylation signal from different gene/genes may be employed with similar results. Specific sequences which regulate post-transcriptional mRNA stability may optionally be included. For example, certain polyA sequences (Volloch et al. *Cell* (1981) 23:509) and β-globin mRNA elements can increase mRNA stability, whereas certain AU-rich sequences in mRNA can decrease mRNA stability (Shyu et al., *Genes and Devel.* (1989) 3:60). In addition, AU regions in 3' non-coding regions may be used to destabilize mRNA if a short half-life mRNA is desirable for the gene of interest.

The construct may additionally include sequences for selection, such as a neomycin resistance gene or a dihydrofolate reductase gene and/or signal sequences to regenerate recombinant proteins that are targeted to different cellular compartments or secreted when the wild type sequence is not. Any of a variety of signal sequences may be used which are well-known to those skilled in the art. These signal sequences may allow generation of new vaccine strategies or produce soluble antagonists directed against specific cell surface receptors such as transformed oncogenes. The sequences for selection may be on a separate plasmid and cotransfected with the plasmid carrying the therapeutic nucleic acid. Where a carrier is used, the selection plasmid may be complexed to a different carrier or to the same carrier as the therapeutic plasmid.

The recombinant coding-sequence flanked at its 5' end by the promoter and regulatory sequences and at its 3' end by a terminator and regulatory sequences may be introduced into a suitable cloning plasmid (e.g., pUC18, pSP72) for use in direct DNA uptake in host cells following introduction into the host. The nucleic acid construct also may be complexed with a carrier such as lipid carriers, particularly cationic lipid carriers. Lipid carriers can be prepared from a variety of cationic lipids, including DOTAP, DOTMA, DDAB, L-PE, and the like. Lipid carriers containing a cationic lipid, such as {N(1-(2,3-dioleyloxy)propyl)-N,N,N, trimethylammonium} chloride (DOTMA) also known as "lipofectin", dimethyl dioctadecyl ammonium bromide (DDAB), 1,2-dioleoyloxy-3-(trimethylammonio)propane (DOTAP) or lysinyl-phosphatidylethanolamine (L-PE) and a second lipid, such as distearoylphosphatidylethanolamine (DOPE) or cholesterol (Chol), are of particular interest. DOTMA synthesis is described in Felgner, et al., *Proc. Nat. Acad. Sciences*, (*USA*) (1987) 84:7413–7417. DOTAP synthesis is described in Stamatatos, et al., *Biochemistry* (1988) 27:3917. DOTMA:DOPE lipid carriers can be purchased from, for example, BRL. DOTAP:DOPE lipid carriers can be purchased from Boehringer Mannheim. Cholesterol and DDAB are commercially available from Sigma Corporation. DOPE is commercially available from Avanti Polar Lipids. DDAB:DOPE can be purchased from Promega. Biodegradable cationic amphiphiles also have been shown to form stable complexes with polyanionic DNA.

Cationic liposomes have been shown to be capable of mediating high level cellular expression of transgenes or mRNA by delivering the nucleic acid into a wide variety of cells in culture. The use of specific cationic lipids can confer specific advantages for in vivo delivery. For example, iv injection of nucleic acid complexed to DOTAP-containing liposomes or ethyl-phosphatidylcholine (E-PC) lipid carriers can target transgene expression primarily to the lung. Furthermore, DOTAP, as well as L-PE and CEBA are fully metabolized by cells, whereas DOTMA cannot be fully metabolized by cells. Therefore, DOTAP, E-PC, and L-PE, but not DOTMA, are suitable for repeated injection into mammalian hosts. Additionally, complexing the cationic lipid with a second lipid, primarily either cholesterol or DOPE can maximize transgene expression in vivo. For example, mixing a steroid, such as cholesterol, instead of DOPE with DOTAP, DOTMA, or DDAB, substantially increases transgene expression in vivo.

Particular cells and tissues may be targeted, depending upon the route of administration and the site of administration. For example, transfection of a tissue which is closest to the site of injection in the direction of blood flow will be transfected in the absence of any specific targeting. Additionally, if desired, the lipid carriers may be modified to direct the lipid carriers to particular types of cells using site-directing molecules. Thus antibodies or ligands for particular receptors may be employed, with a target cell associated with a particular surface protein. For example, with the AIDS virus, the AIDS virus is primarily directed to cells having the CD4 surface protein. By having anti-CD4 antibody bound to the surface of the lipid carrier, the lipid carrier may be directed primarily to T-helper cells. A particular ligand or antibody may be conjugated to the lipid carrier in accordance with conventional ways, either by conjugating the site-directing molecule to a lipid for incorporation into the lipid bilayer or by providing for a linking group on a lipid present in the bilayer for linking to a functionality of the site-directing compound. Such techniques are well known to those skilled in the art. Ligand-directed DNA-polycation complexes have been shown to transfect to hepatocytes in the liver after iv injection; the ability to transfect other cell types or tissue types by this approach has not been demonstrated. Non-cationic lipid carriers, particularly pH sensitive liposomes, offer another potentially attractive approach to in vivo gene therapy. However, as compared to cationic liposomes, pH sensitive liposomes are less efficient in capturing DNA and delivering DNA intracellularly and may be inactivated in the presence of serum, thus limiting their iv use.

Unexpectedly, either the liposomal lipid composition or the mean diameter of the lipid carriers (when in particle form such as a liposome) injected can dramatically affect the level of transgene expression produced in vivo. Thus, the liposomal lipid compositions generally have a composition of 50% molar ratio of cationic lipid to non-cationic lipid, but may range from 5% to 100%. The diameter of the lipid carriers should generally be within the range of 100 nm to 10 microns. Cationic lipid carrier-DNA complexes wherein the lipid carriers range from 100 nanometers to several microns in diameter can produce significant levels of transgene expression after systemic introduction into a mammalian host.

The use of lipid carriers of greater than 500 nanometers (in other words multicellular vesicles (MLV) or large unilamellar vesicles (LUV)) can in certain cases significantly increase the level of transgene expression achieved in a mammalian host when compared to small unilamellar vesicles (SUV). MLV and LUV are prepared by vortexing rather than sonicating after addition of the aqueous material to the dry lipid film. If desired, the resulting lipid carriers can be extruded under high pressure through sized polycarbonate membranes to achieve more uniform size distributions.

Also unexpectedly, the use of particular nucleic acid to lipid carrier ratio also is essential; the ratios used determine whether and to what level transgenes are expressed in vivo and needs to be optimized, depending upon various factors including the nature of the construct, the size and lipid composition of the lipid carrier and whether it is MLV or SUV the route of administration and the host mammal. As an example, using a reporter gene CAT (chloramphenicol acetyl transferase), an approximately 1:1 (range 0.5:1 to 2:1) DNA to lipid carrier ratio ($\mu$g DNA to nmoles of the cationic lipid) produces the highest levels of gene expression in a mouse in all organs after ip administration, and an approximately 1:4 ratio, (range 2:1 to 1:7) produces the highest levels of gene expression in all organs after iv administration. In addition to achieving a high level of transgene expression in a wide variety of tissues using optimal conditions, the majority of all cells present in the lung, spleen, lymph nodes and bone marrow are transfected in vivo, as well as the majority of all endothelial cells present in the heart.

The DNA:lipid carrier ratio determines whether or not, and at what level, transgenes are expressed in mammalian hosts after systemic injection of the complexes. Several factors are important in order optimize the DNA:lipid carrier ratio. Thus, specific DNA:lipid carrier ratios are required for each type of cationic lipid used as well as for each different lipid carrier size used. To optimize, for each lipid carrier composition used, DNA must be mixed together with the lipid carriers in multiple different ratios, ranging from 6:1 to 1:10 (micrograms DNA to nanomoles cationic lipid), in order to determine which ratios result in aggregation of the DNA:lipid carrier complexes. Ratios which result in aggregation cannot be used in vivo. The ratios which do not result in aggregation are tested in animal models to determine which of the DNA:lipid carrier ratios confers the highest level of transgene expression in vivo. For example, the optimal DNA:lipid carrier ratios for SUV for DOTMA/DOPE, DDAB/DOPE, DOTAP/DOPE, DOTAP/Chol, LPE:CEBA, DDAB:Chol. and L-PE:DOPE are 1:4, 1:3, (very low activity at all ratios), 1:6, 1:1, 1:5, and 2:1, respectively. DNA:lipid carrier complexes must be made in appropriate physiologic solutions. The DNA:lipid carrier complexes must be mixed in physiologic solutions (approximately 290 milliosmoles) which do not themselves induce aggregation of the DNA:lipid carrier complexes. The solutions include 5% dextrose in water or normal saline.

Cell surface receptors for cationic lipid carriers can be used to both regulate and confer target cell specificity on transgene expression in mammalian hosts. Cationic lipid carrier:DNA complexes are internalized by cells by a classical receptor-mediated endocytosis (see FIG. 7) using cell surface receptors which contain specific binding sites for, and are able to internalize, cationic molecules. Using agents such as cytokines, growth factors, other soluble proteins and certain drugs, it is thus possible to selectively up or down regulate these cation-binding receptors. The rate of up or down regulation of these receptors by the appropriate agent will allow selection of specific cells for enhanced or reduced levels of transfection in vivo. Furthermore, surprisingly cell surface receptors for naked DNA can be used both to regulate and to confer target cells specificity on transgenic expression in a mammalian host.

The most frequent interaction between DOTMA lipid carriers, either the uni- or multilamellar lipid carriers, complexed to plasmid DNA and the various cell types (for example, CV-1 monkey kidney cells, U937 human myelomonocytic leukemia cells, K562, MEL (murine erythroblastic leukemia cells), rat alveolar macrophages, and alveolar type II cells), is that of lipid carrier adhesion and internalization. This interaction is common to well-defined examples of receptor-mediated endocytosis. All cells which appear to have contacted cationic lipid carrier:DNA complexes ingest the complexes after binding to the plasma membrane. All these cell types demonstrate the same classical receptor-mediated endocytic pathway of internalization.

The mammalian host may be any mammal, particularly a mammal having symptoms of a genetically-based disorder. Thus, the subject application finds use in domestic animals, feed stock, such as bovine, ovine, and porcine, as well as primates, particularly humans. The mammalian host may be pregnant, and the intended recipient of the gene-based therapy may be either the gravid female or the fetus or both. In the method of the invention, transfection in vivo is obtained by introducing a therapeutic transcription or expression vector into the mammalian host, either as naked DNA or complexed to lipid carriers, particularly cationic lipid carriers. The constructs may provide for integration into the host cell genome for stable maintenance of the transgene or for episomal expression of the transgene. The introduction into the mammalian host may be by any of several routes, including intravenous or intraperitoneal injection, intratracheally, intrathecally, parenterally, intraarticularly, intramuscularly, etc. Of particular interest is the introduction of a therapeutic expression vector into a circulating bodily fluid. Thus, iv administration and intrathecal administration are of particular interest since the vector may be widely disseminated following such a route of administration. Any physiologically acceptable medium may be employed for administering the DNA or lipid carriers, such as deionized water, saline, phosphate-buffered saline, 5% dextrose in water, and the like, depending upon the route of administration. Other components may be included in the formulation such as buffers, stabilizers, biocides, etc. These components have found extensive exemplification in the literature and need not be described in particular here.

The amount of lipid carriers used will be sufficient to provide for adequate dissemination to a variety of tissues after entry of the DNA or complexes into the bloodstream and to provide for a therapeutic level of expression in transfected tissues. A therapeutic level of expression is a sufficient amount of expression to, prevent, treat or palliate a disease of the host mammal. In addition, the dose of the plasmid DNA expression vector used must be sufficient to produce significant levels of transgene expression in multiple tissues in vivo for example, $\geq 1$ mg of an expression plasmid alone is injected into a mouse to achieve high level expression of the CAT gene in multiple tissues. Other DNA sequences, such as adenovirus VA genes can be included in the administration medium and be co-transfected with the gene of interest. The presence of genes coding for the adenovirus VA gene product may significantly enhance the translation of mRNA transcribed from the plasmid.

The level and tissues of expression of the recombinant gene may be determined at the mRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reporter gene product present in the expression cassette. Alternatively, potential therapeutic effects of the gene product can be measured, for example where the DNA sequence of interest encodes GM-CSF, by determining the effects of gene expression on survival of lethally irradiated animals in which the GM-CSF transgene is expressed. Production of significant amounts of a transgene product will substantially prolong the survival of these mice.

Where expression of the polypeptide/protein or even the mRNA itself confers a changed biochemical phenotype upon the host, the presence of a new phenotype or absence of an old phenotype may be evaluated; for example, as a result of transfection of the host cells, there may be enhanced production of pre-existing desirable products formerly produced in insufficient quantities or there may be reduction or even suppression of an undesirable gene product using antisense, ribozyme or co-suppression technologies; in the case of suppression, a reduction of the gene product may be determined. Typically, the therapeutic cassette is not integrated into the host cell genome. If necessary, the treatment can be repeated on an ad hoc basis depending upon the results achieved. If the treatment is repeated, the mammalian host can be monitored to ensure that there is no adverse immune response to the treatment.

The subject compositions can be provided for use in one or more procedures. Kits will usually include the DNA either as naked DNA or complexed to lipid carriers. Additionally, lipid carriers may be provided in a separate container for complexing with the provided DNA. The DNA either for direct injection or for complexing with lipid carriers, or the lipid carrier/DNA complexes may be present as concentrates which may be further diluted prior to use or they may be provided at the concentration of use, where the vials may include one or more dosages. Conveniently, single dosages may be provided in syringes, contained in sterilized containers, so that the physicians or veterinarian may employ the syringes directly, where the syringes will have the desired amount and concentration of agents. Thus, the kit may have a plurality of syringes containing the DNA or the DNA/lipid carrier complexes in appropriate proportional amounts. When the syringes contain the formulation for direct use, usually there will be no need for other reagents for use with the method.

The invention finds use in in vivo prevention, treatment and/or palliation of a number of diseases. In vivo replacement of a gene can be accomplished by techniques such as homologous recombination or initial knockout of the aberrant gene and subsequent replacement with the desired transgene.

The following examples are offered by way of illustration and not by limitation.

EXAMPLES

Example 1

Preparation of Plasmids for In Vivo Gene Therapy

Figure 6A:
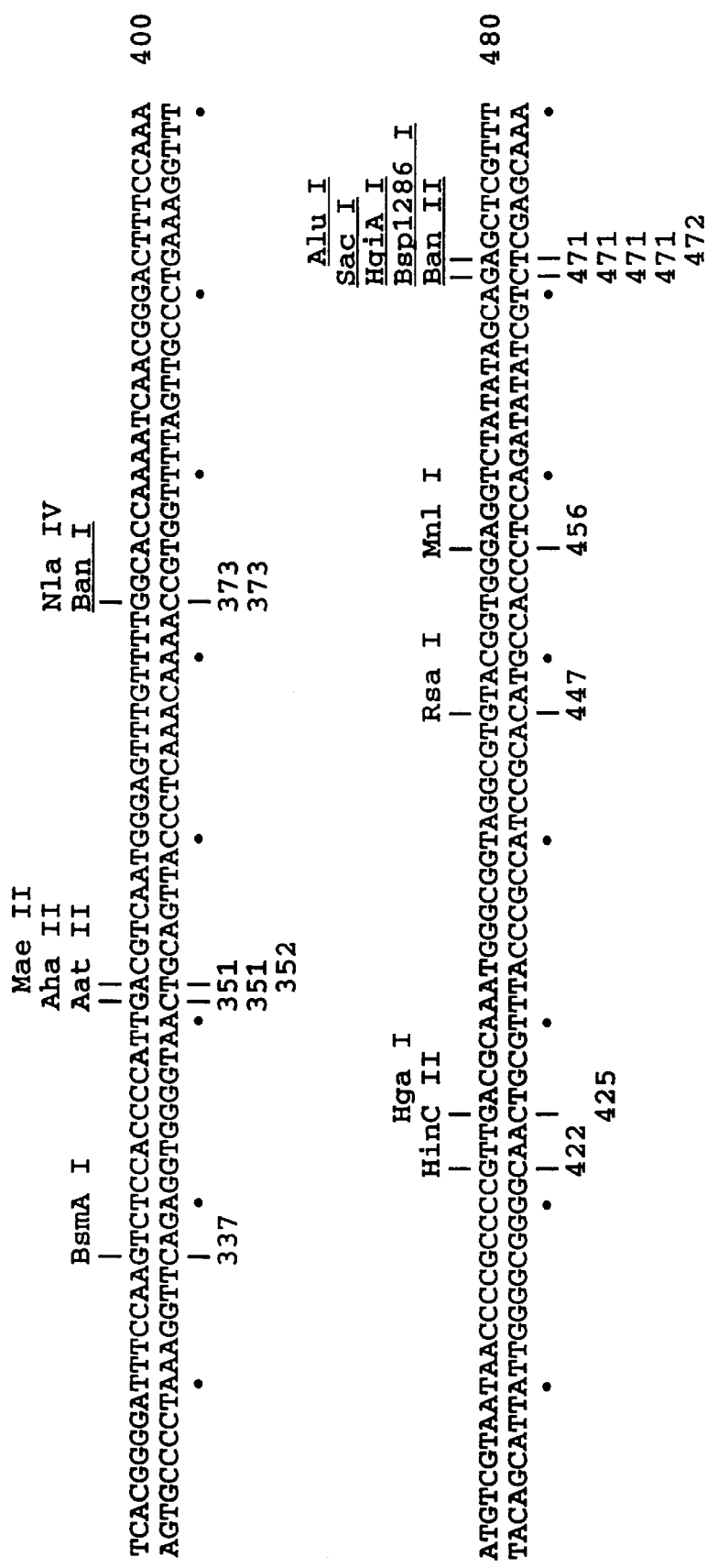
Figure 13A:
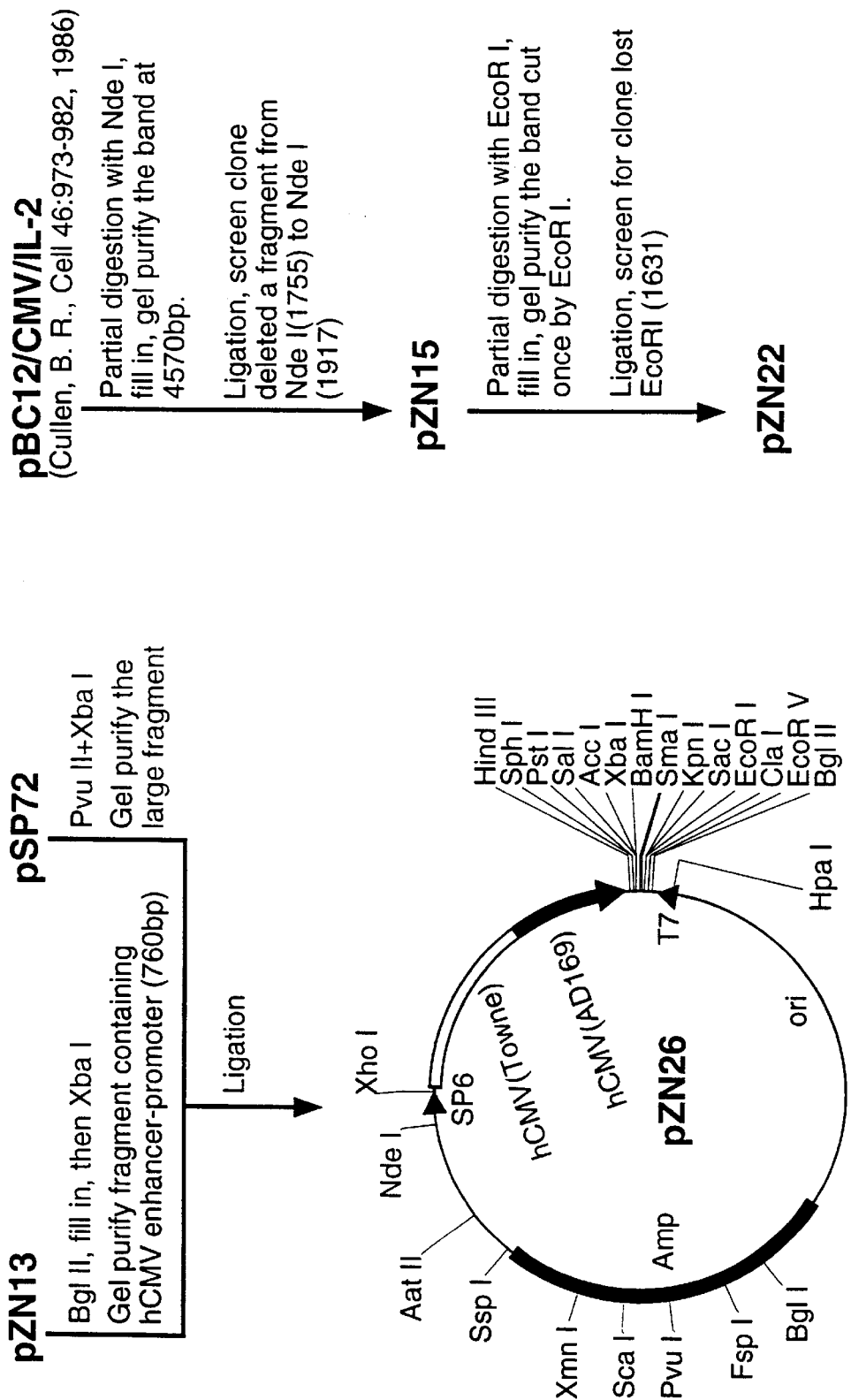
FIG. 13A and FIG. 13B show the construction of plasmid pZN46.
Figure 13A:
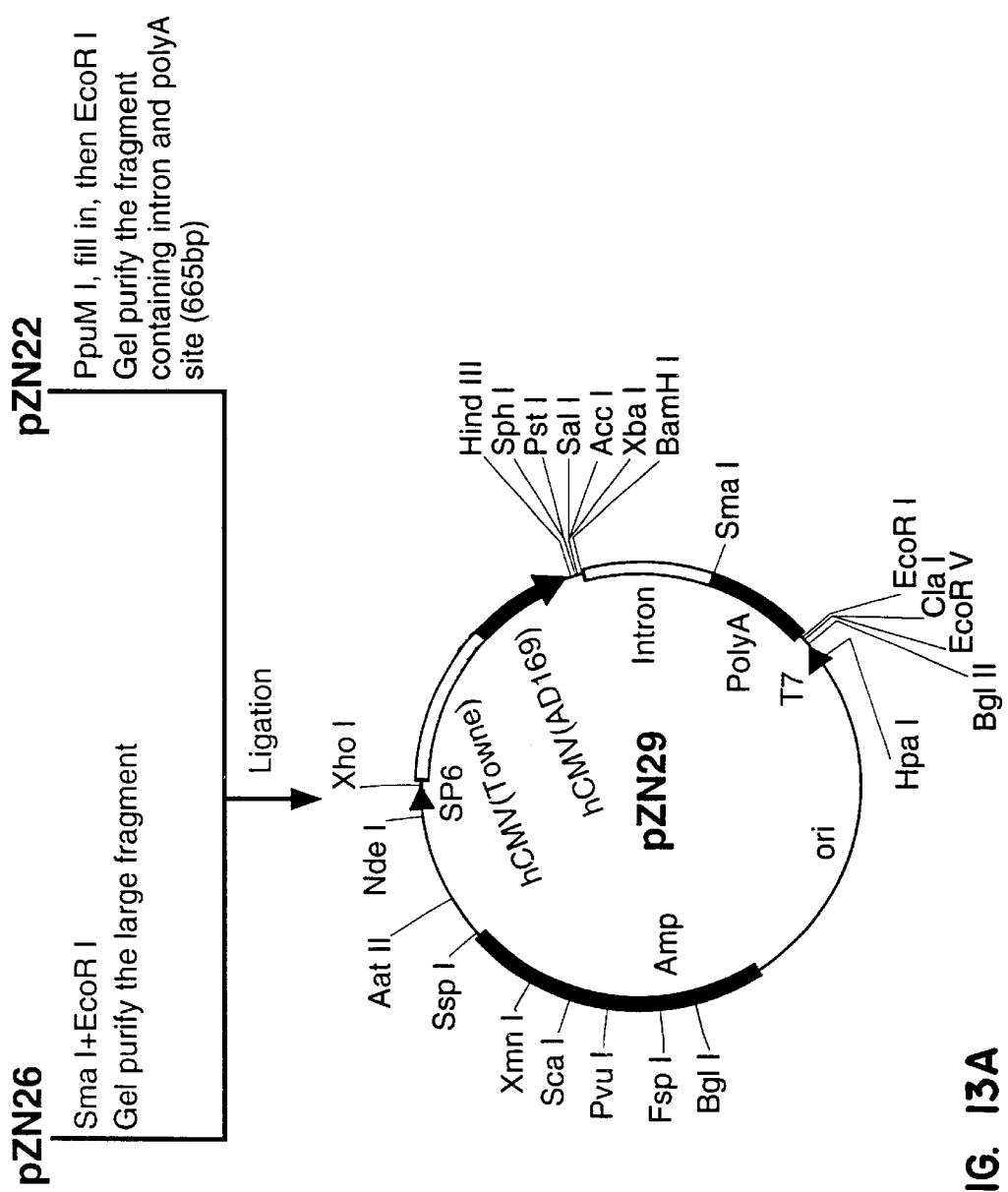
Figure 13A:
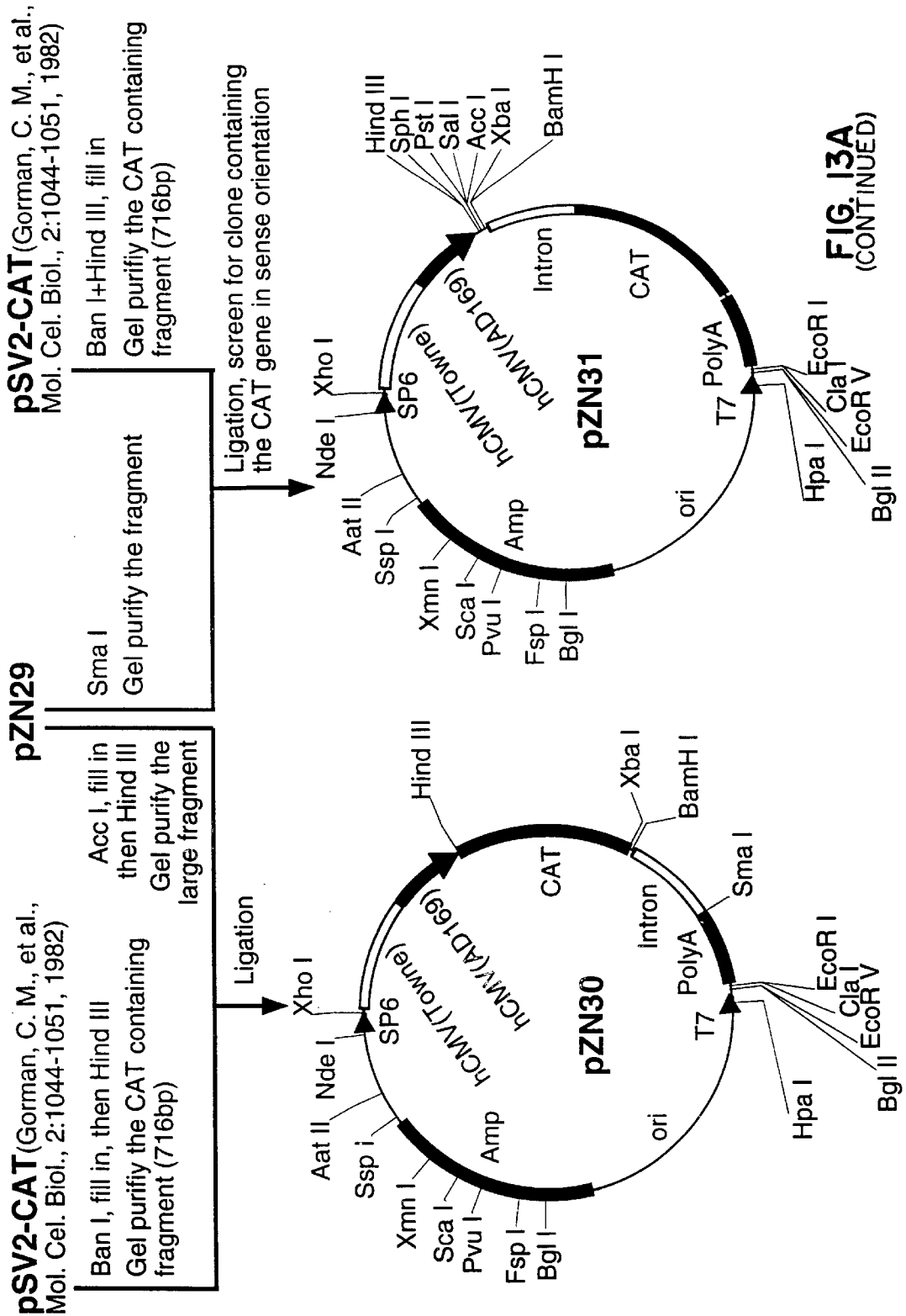
Figure 13B:
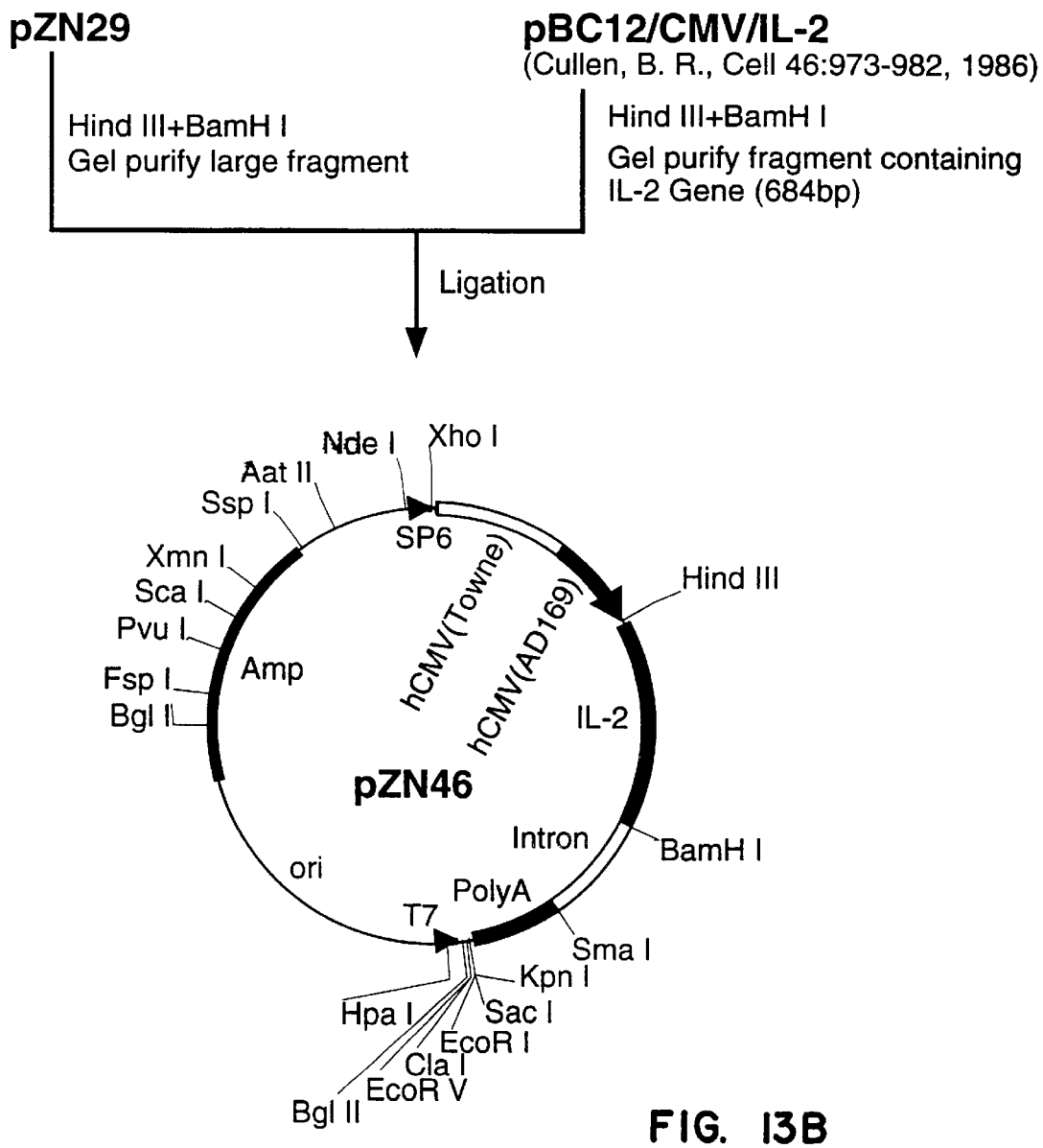
Figure 16:
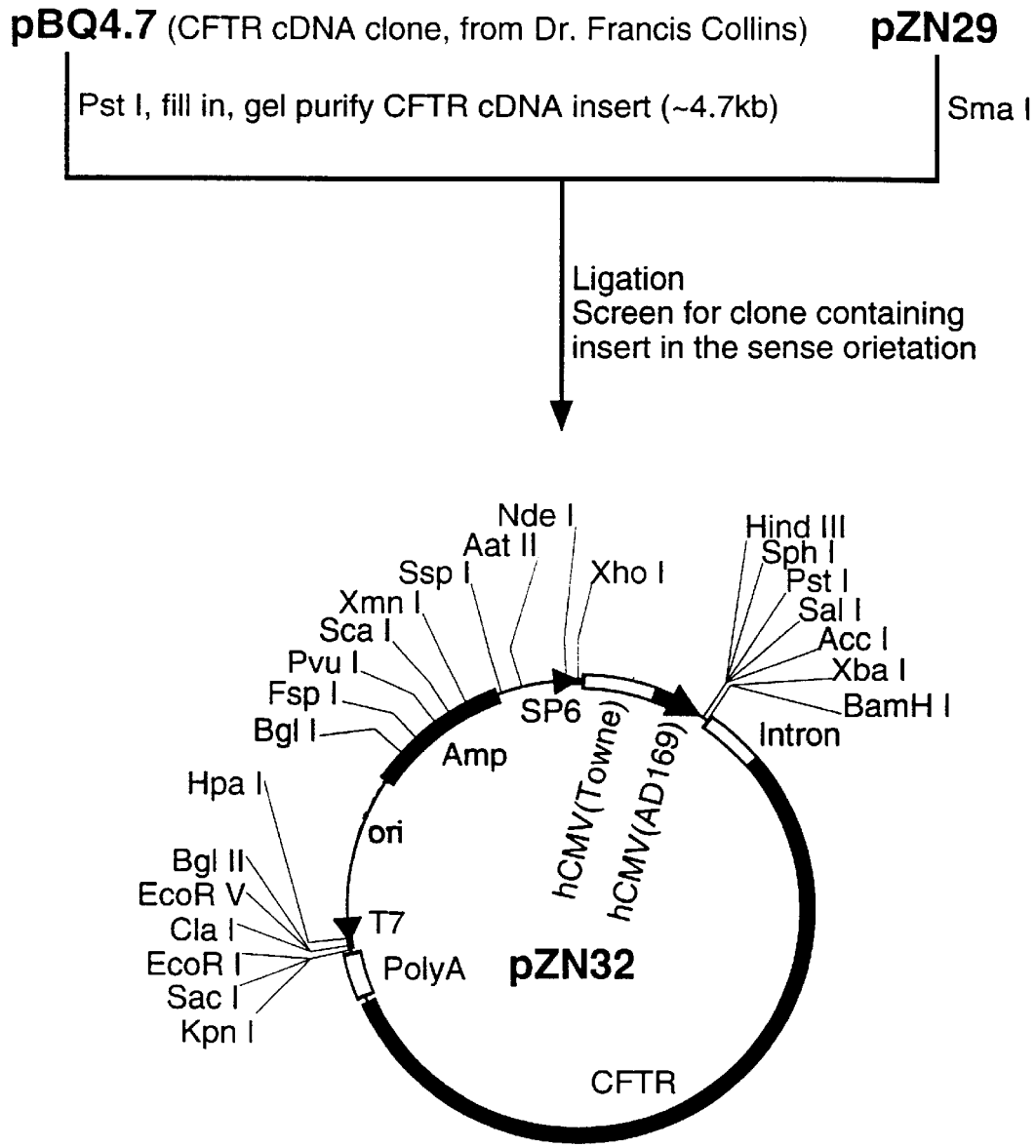
FIG. 16 shows the construction of plasmid pZN32.
Figure 17A:
FIGS. 17A–17E show a photomicrograph of immunohistochemically stained frozen sections of lung tissue from mice treated by intravenous administration of either pZN32:cationic lipid carrier complexes or lipid carrier alone (control mice).
Figure 17B:
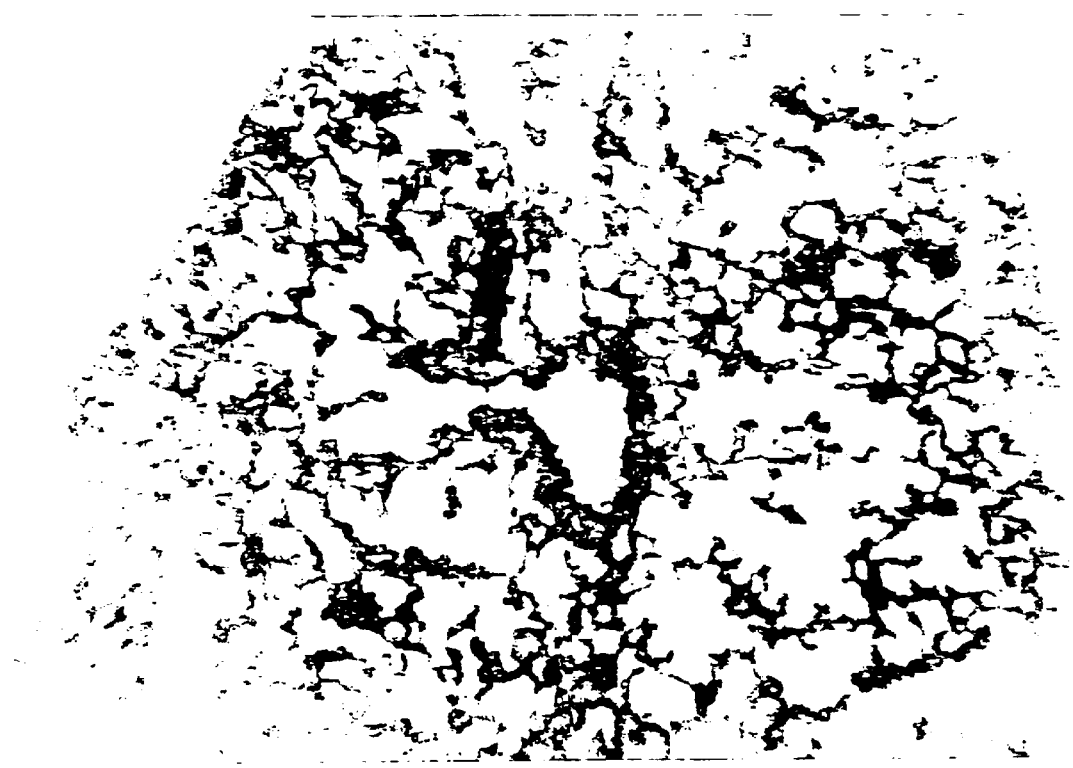
Figure 17C:
Figure 17D:
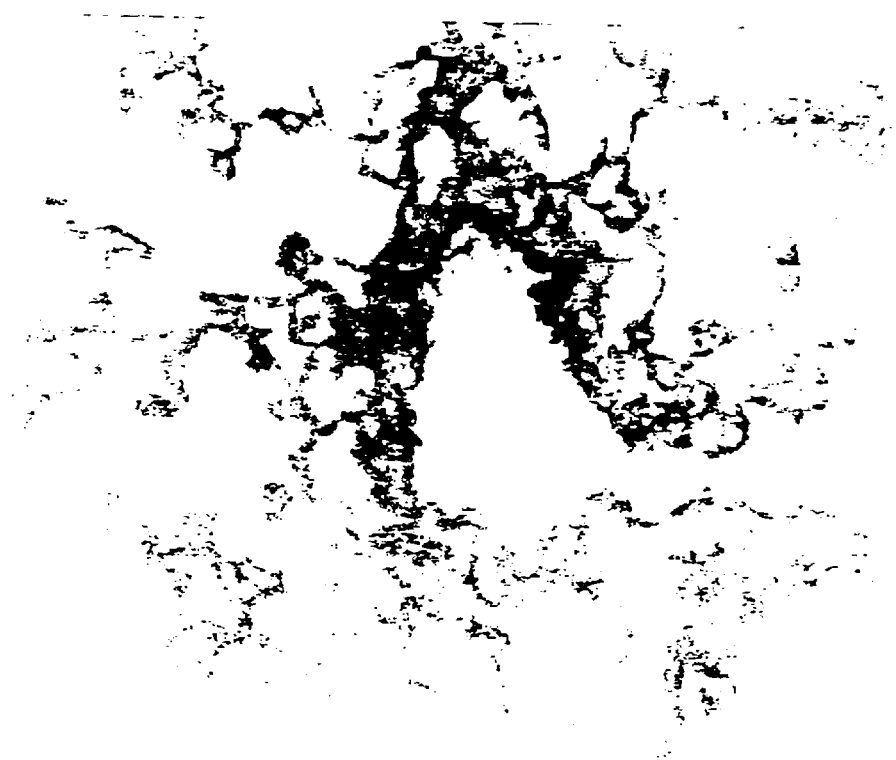
Figure 17E:
Figure 18:
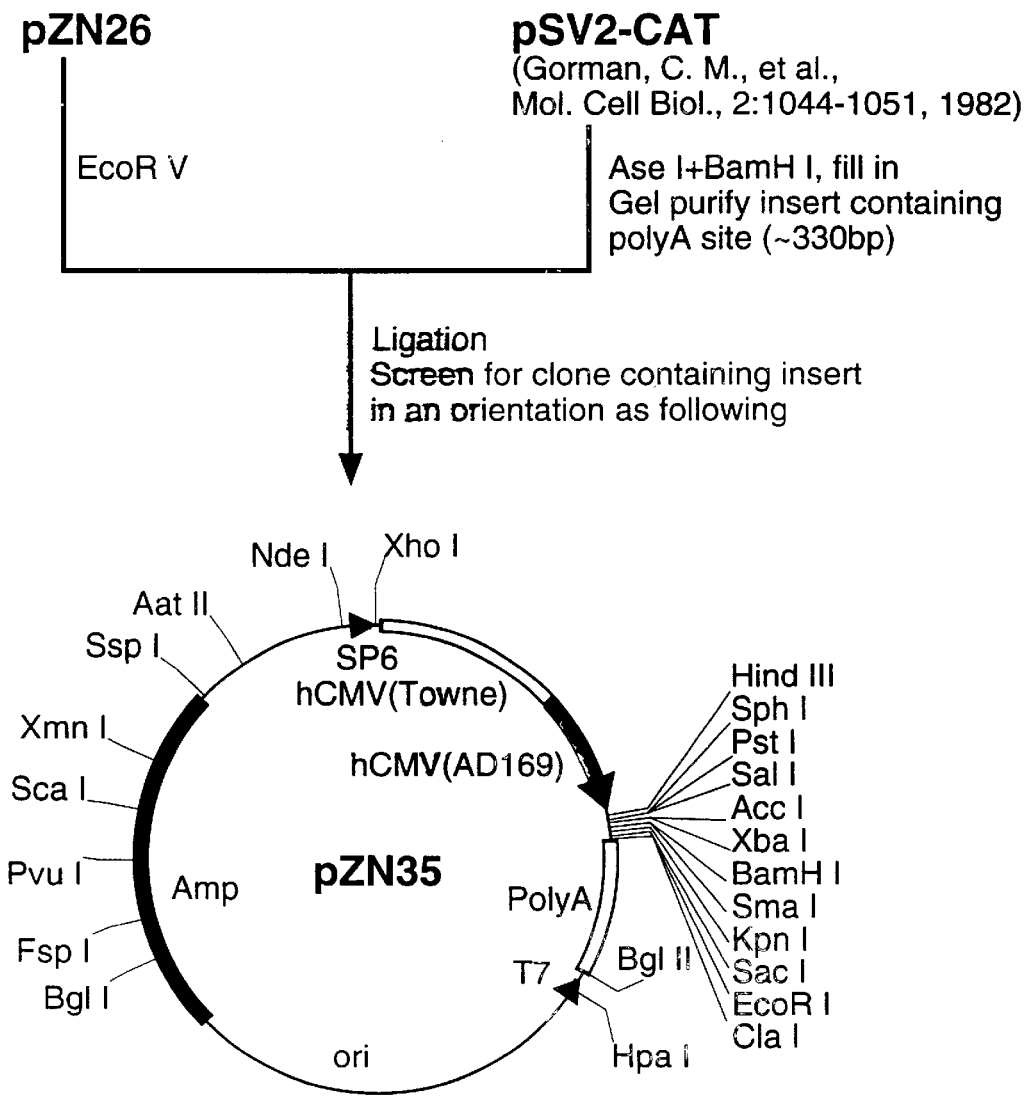
FIG. 18 shows the construction of plasmid pZN51.
Figure 18:
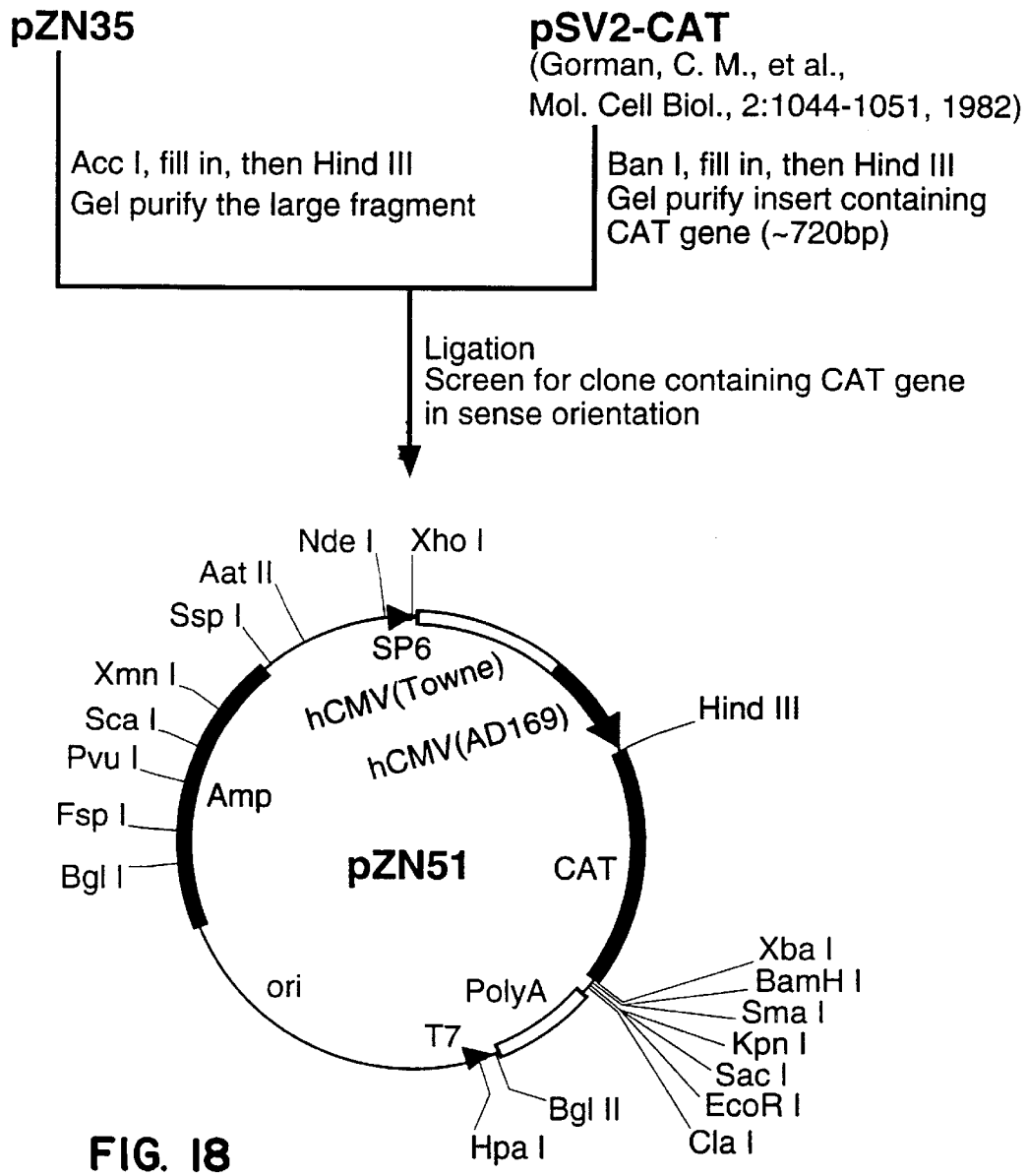
Figure 19A:
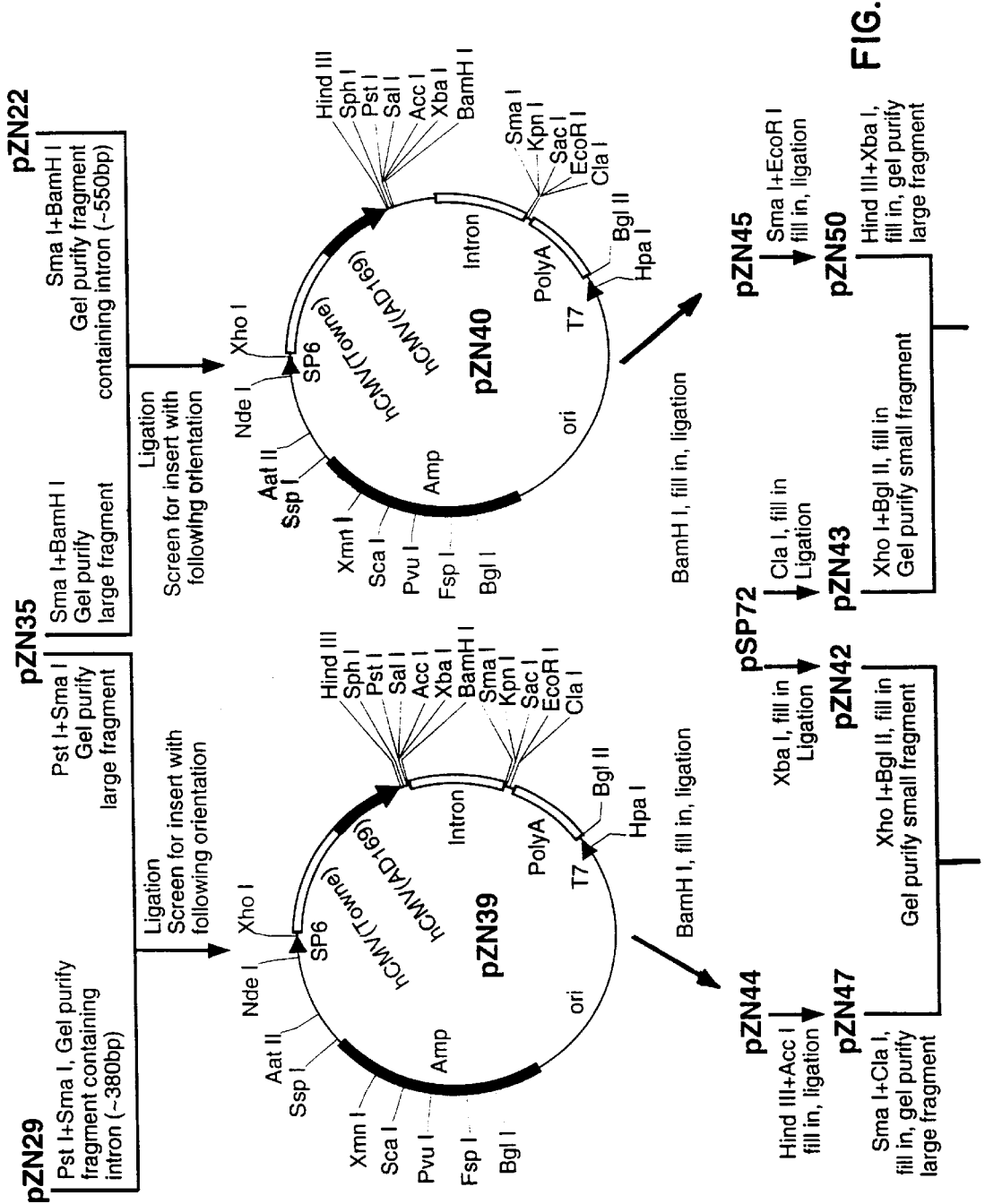
FIGS. 19A–19C show the construction of plasmids pZN60, pZN61, pZN62 and pZN63.
Figure 19B:
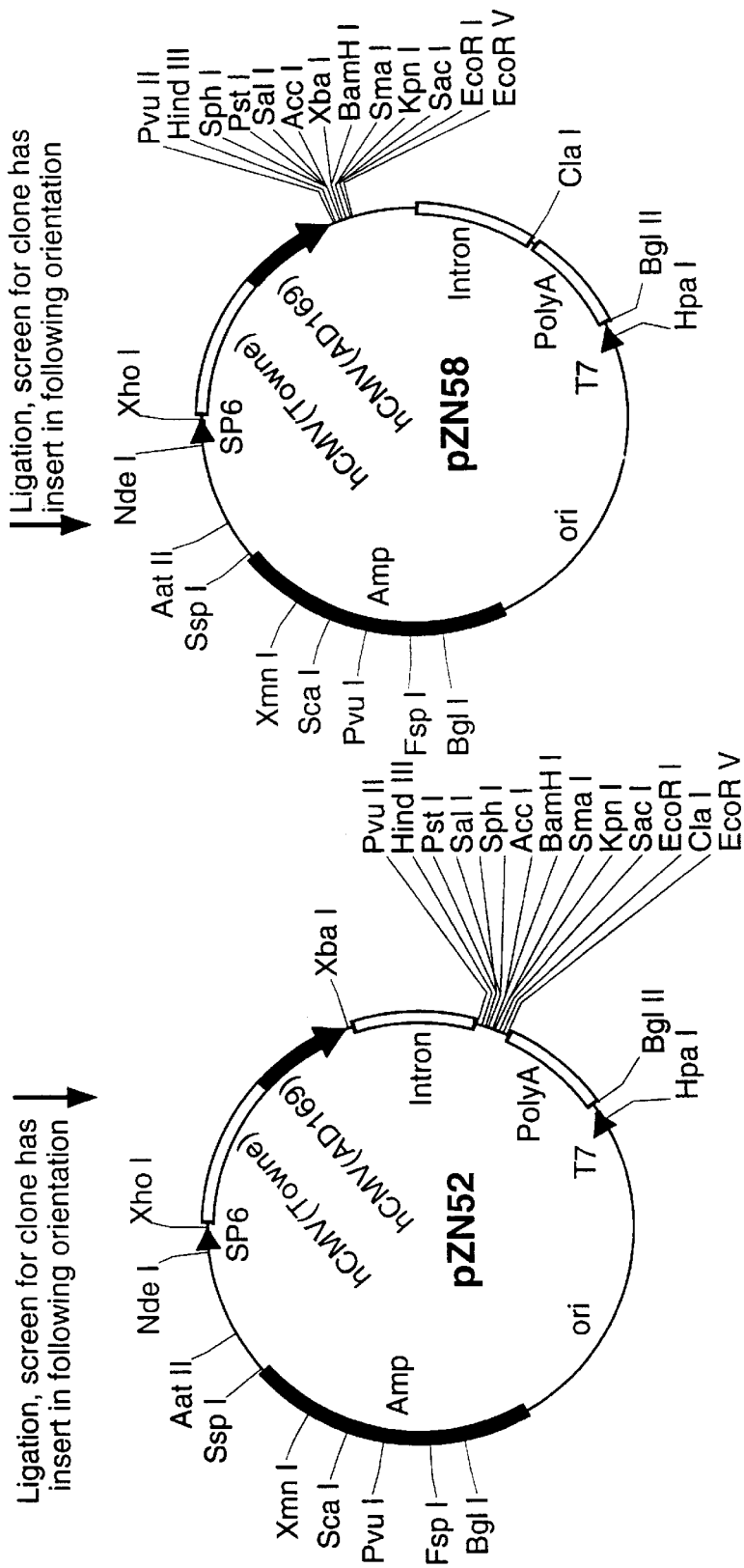
Figure 19B:
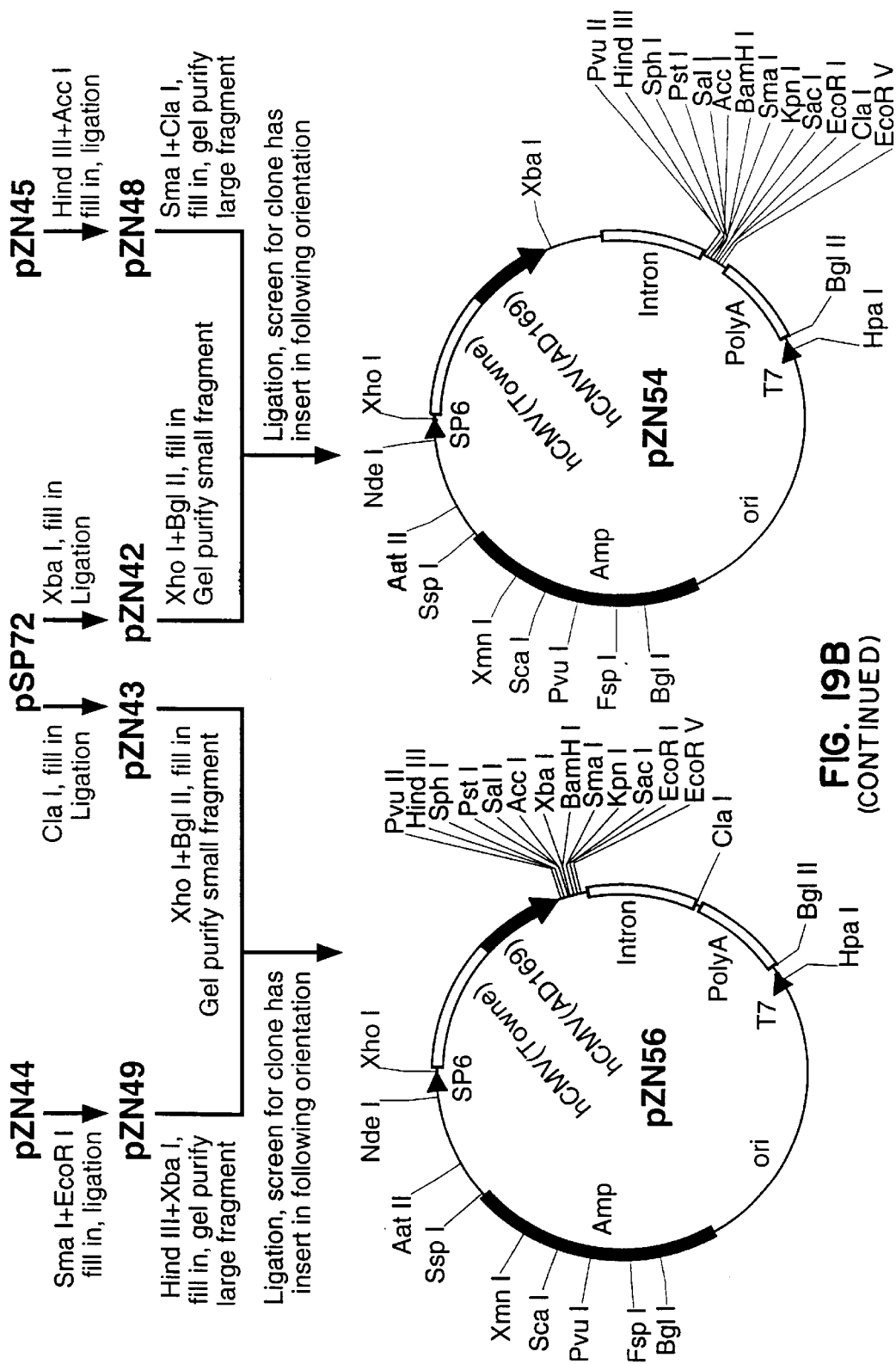
Figure 19C:
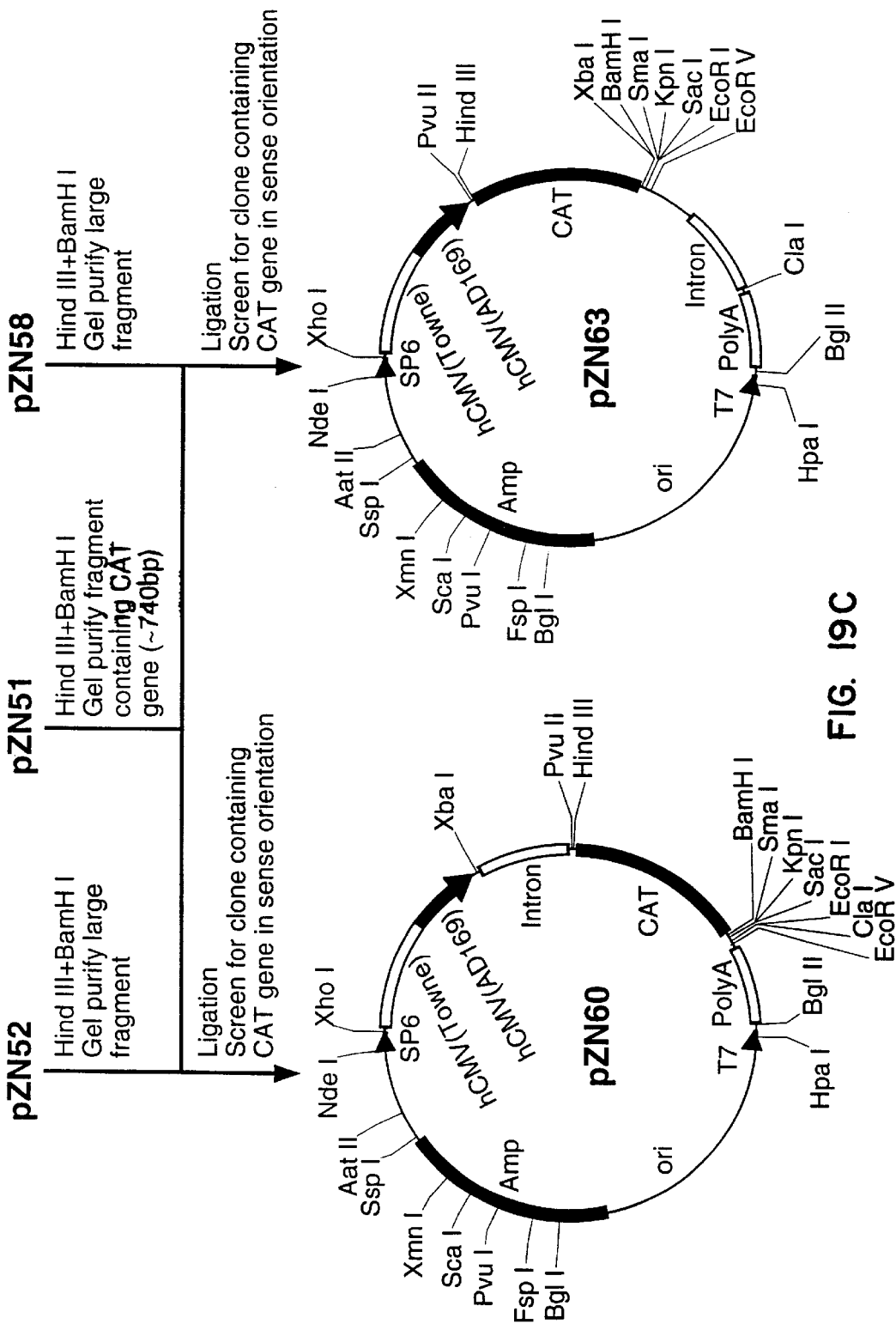
Figure 19C:
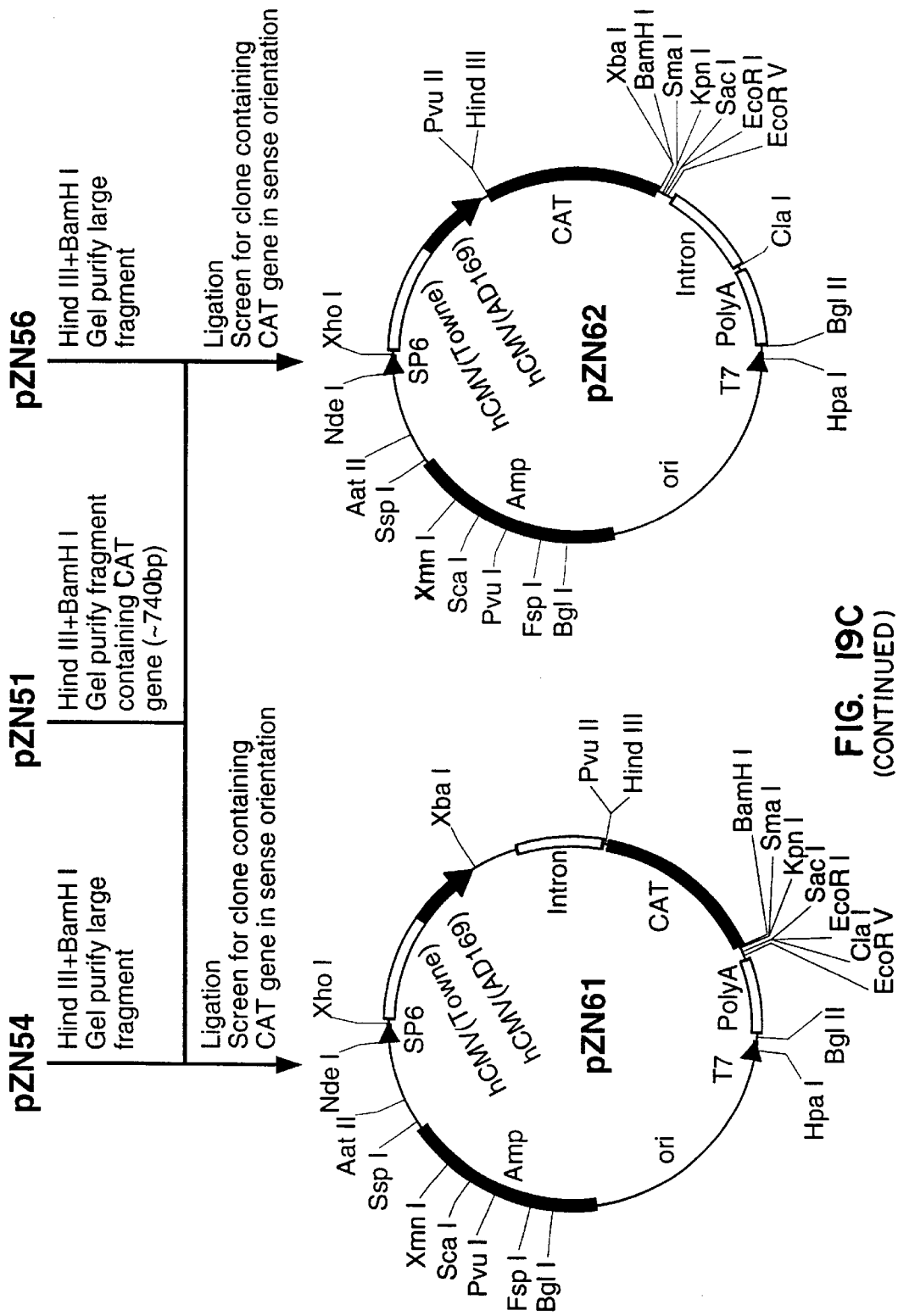
Figure 20:
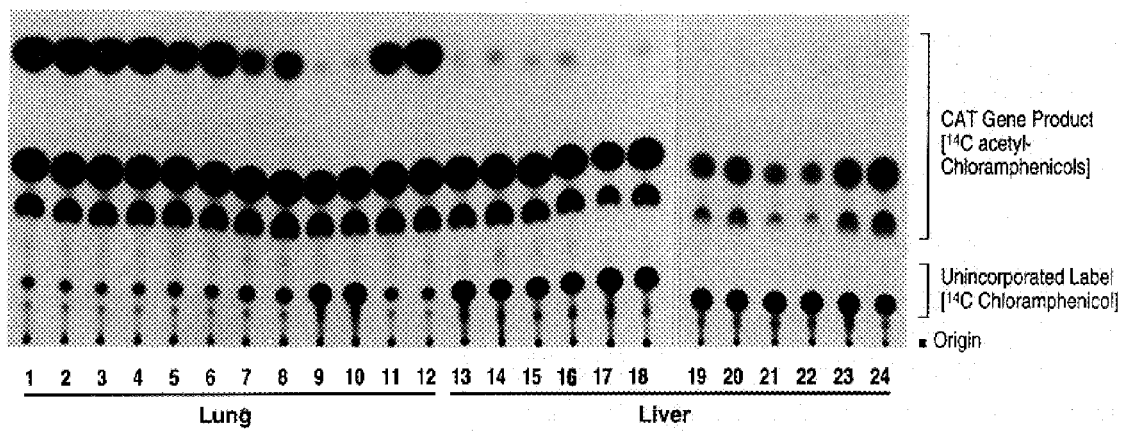
FIG. 20 shows an autoradiograph of the thin layer chromatograph of a CAT assay for six different plasmids injected intravenously in mice. Lanes 1–12 show the CAT activity in lung tissue; Lanes 13–24 show the CAT activity in liver tissue. Lanes 1, 2, 13, 14-pZN51; lanes 3, 4, 15, 16-pZN60; lanes 5, 6, 17, 18-pZN61; lanes 7, 8, 19, 20-pZN62; lanes 9, 10, 21, 22-pZN63; lanes 11, 12, 23, 24-pZN27. Lipid carriers were DDAB:Chol (1:1). Lipid carriers-DNA complexes were 5 nmoles cationic lipid to 1 $\mu$g DNA. 100 $\mu$g DNA was injected per mouse. Each lane represents a single mouse. Chromatograph runs from bottom to top of the Figure as shown.

Details regarding the plasmids that have been used for transfection of mammalian cells are as follows.

pRSVCAT: construction of this plasmid is described in Gorman et al., *Proc. Nat. Acad. Sciences (USA)* (1982), 79:6777–6781. In the pRSVCAT plasmid, the 3'-RSVLTR is juxtaposed as a promoter upstream from CAT encoding sequences. The distance between the LTR transcriptional start site and the CAT initiation codon (the first AUG downstream from the start site) is about 70 bp.

p5'PRL3-CAT: construction of this plasmid is described in Sakai et al., *Genes and Development* (1988) 2:1144–1154.

pSIS-CAT: construction of this plasmid is described in Huang and Gorman, *Nucleic Acids Research* (1990) 18:937–948.

pZN20: construction of this plasmid is illustrated in FIG. 5. The plasmid was prepared as follows. pCATwt760 (Stinski and Roehr (1985) *J. Virol.* 55:431–441) was treated with HindIII and the fragment containing the HCMV base IE 1 enhancer and promoter element purified. The isolated fragment was then cloned into the HindIII site of pSP72 (Promega) creating pZN9. Clones were screened in which the enhancer and promoter element is as shown in FIG. 5. Following partial HindIII digestion of pZN9, the blunt ends were filled in with DNA polymerase I Klenow fragment. The resulting clone pZN12 has lost the HindIII site 5' to the enhancer and promoter element. pZN12 was then treated with Nco1 and HindIII and the large Nco1-HindIII fragment purified and ligated to a purified small Nco1-HindIII fragment from pBC12/CMV/IL-2 (Cullen, *Cell* (1986) 46:973–982). pBC12/CMV/IL-2 contains the HCMV promoter from the AD169 strain. The resulting clone was pZN13. pZN13 was partially digested with BamH1, filled in with DNA polymerase I Klenow fragment and the resulting clones screened for the clone which has lost the BamHI site at the 5' end of the enhancer and promoter element. The resulting clone was called pZN17. pZN17 was treated with HindIII and BamHI and the resulting HindIII-BamHI large fragment was purified and ligated to a purified small HindIII-BamHI fragment obtained from pSV2-CAT (Gorman et al. (1982), *Molecular Cell Biology*, 2:1044–1051). The resulting clone was pZN20. The full restriction map of HCMV (Towne) is shown in FIG. 6A. HCMV (AD169) is shown in FIG. 6C. A comparison of the two promoters is shown in FIG. 6B. Significantly more expression is obtained when a promoter from the AD169 strain is used as compared to one from the Towne strain. pZN20 contains a composite promoter which has the Towne sequence 5' of the NcoI site and the AD169 sequence 3' of the NcoI site. The NcoI site is indicated by the asterisk in FIG. 6B. pZN20 has this composite HCMV promoter followed by the CAT gene, SV40 t-intron and SV40 polyA addition site.

pZN27: Construction of this plasmid is illustrated in FIG. 11. pZN27 contains the composite HCMV promoter followed in order by the SV40 t-intron, the CAT coding sequence and the SV40 polyA addition site.

pZN46: Construction of this plasmid is shown in FIG. 13A and FIG. 13B. pZN46 contains the composite HCMV promoter, followed by the human IL-2 gene, rat preproinsulin 2 intron and polyA addition site from the rat preproinsulin 2 gene. These last three components were derived from pBC12/CMV/IL-2 plasmid of Cullen (*Cell* 46:973–982 (1986)). The rat preproinsulin2 intron was modified by deleting an internal 162 base pair NdeI fragment.

pZN32: Construction of this plasmid is shown in FIG. 16. pZN32 contains the composite HCMV promoter followed in order by the modified rat preproinsulin2 intron described for pZN46, CFTR cDNA, and rat preproinsulin2 gene polyA addition site as described for pZN46. CFTR cDNA was obtained from pBQ4.7 from F. Collins (Univ. of Michigan).

pZN51: Construction of this plasmid is shown in FIG. 18. pZN51 contains the composite HCMV promoter followed by the CAT coding sequence and the SV40 polyA site.

pZN60, pZN61, pZN62, pZN63: Construction of these plasmids is shown in FIG. 19. pZN60 contains the HCMV composite promoter followed by the modified rat preproinsulin 2 intron, the CAT coding sequence, and the SV40 polyA addition site. pZN61 is identical to pZN60 but contains an additional 166 base pairs 5' to the intron. This additional DNA is the 166 bp immediately 5' of the intron in the pBC12/CMV/IL-2 plasmid and may contain rat preproinsulin 2 gene coding sequence. pZN62 is similar to pZN60 except that the intron is 3' of the CAT coding sequence rather than 5' as in pZN60. pZN63 is identical to pZN62 except for the additional 166 base pairs 5' to the intron. This is the same additional sequence described for pZN61.

pCIS-CAT: This plasmid was made as described in Huang, M. T. F. and Gorman, C. M. *Nuc. Acids Res.* (1990) 18:937–947, with the exception that a CMV promoter and a hybrid intron sequence were used rather than the SV40 promoter in the plasmid pML.I.CAT, described therein. Briefly, the CAT lipid carrier was constructed by first making a pML-based plasmid containing the CMV promoter immediately followed by a portion of the 5'-untranslated leader from the adenovirus-major late (AML) region. This region contained all but the first 13 nucleotides of the first exon of the tripartite leader plus a portion of an intervening sequence (IVS) from the AML region. A synthetic oligonucleotide was inserted which merged with the adenovirus intron to provide a functional splice acceptor sequence derived from an IgG variable region. Bothwell, et al., *Cell* (1981) 24:625–637. This plasmid was then cut at two restriction sites bordering the intron (ClaI and PstI) to remove a 292 bp fragment. A matching synthetic oligonucleotide linker was inserted. The plasmid was termed pCIS-CAT.

Example 2

Preparation of Lipid Carriers and DNA Complexing With Lipid Carriers

Lipid carriers containing a cationic lipid, such as N{1-(2,3-dioleyloxy)propyl}-N,N,N-trimethylammonium (DOTMA), dimethyl dioctadecyl ammonium bromide (DDAB), or 1,2-dioleoyloxy-3-(trimethylammonio)propane (DOTAP) or lysinyl-phosphatidylethanolamine and a second lipid, such as dioleoylphosphatidylethanolamine (DOPE) or cholesterol, were prepared as follows.

Preparation of Lipid Carriers:

Lipids, e.g. DDAB, L-lysinyl-phosphatidylethanolamine (L-PE), cholesterol-ester-β-alanine (CEBA), DOTAP, and cholesterol (Chol) were dissolved in chloroform. Proper amounts of each lipid (determined by the desired molar ratio of each lipid in the final lipid carrier formulation usually 1 to 1 moles cationic lipid to moles non-cationic lipid but ranging from 5 to 1 to 1 to 5) were mixed together and evaporated to dryness on a rotary evaporator. The lipid film was then resuspended by vortexing after the addition of 5% dextrose in water or lipid carrier buffer (25 mM Tris-HCl pH7.4, 100 $\mu$M $ZnCl_2$ isotonic solution) to make a final lipid concentration of 20 mM of multi-lamellar vesicles (MLV). For the preparation of small unilamellar vesicles (SUV), the mixture was then sonicated in a bath sonicator for 15 min, and the lipid carriers were stored under argon at 4° C. until use.

Plasmid Preparation:

The *E. coli* strain which carries the plasmid was grown in TB at 37° C. The method of plasmid purification is a modification of the protocol of "lysis by alkali" and "purification of plasmid DNA by precipitation with polyethylene glycol" described by Sambrook, et al. (*Molecular Cloning*, 2nd edition, 1989, Cold Spring Harbor Laboratory Press). The modification is that the precipitation of DNA by PEG is omitted. The final DNA preparation is dissolved in 10 mM Tris-HCl pH 8.0.

Preparation of Lipid Carrier-plasmid Complexes:

Plasmids were diluted separately in 5% dextrose in water solution to the desired concentration (usually 1 $\mu$g/$\mu$l). The lipid carriers were also diluted in 5% dextrose in water to the same volume as the plasmid.

The amounts of lipid carriers used were determined based on the ratio of moles of liposomal lipid to $\mu$g of plasmid added, e.g. for lipid carrier:plasmid=1:1, one nanomole of cationic lipid is mixed with 1 $\mu$g of plasmid DNA. Plasmid and lipid carriers were then mixed together to form DNA:lipid carrier complexes.

Dose injected. At least 50 $\mu$g, and routinely 100 $\mu$g of plasmid DNA complexed to cationic lipid carriers is injected per mouse. For injection of plasmid alone, at least 500 $\mu$g and routinely 2 mg of plasmid DNA is injected by tail vein per mouse.

Example 3

Demonstration by Immunohistochemistry of CAT Gene Expression in the Lung After Intravenous (iv) Injection of pZN27-DDAB:Cholesterol Lipid Carrier Complexes Lipid carrier: DDAB:Chol=1:1, stock 20 mM in lipid carrier buffer.

Plasmid: pZN27.

DNA:Lipid carrier Ratio: lipid carrier:plasmid=5 nanomoles cationic lipid: 1 $\mu$g DNA DNA dose: 100 $\mu$g plasmid DNA in 200 $\mu$l 5% dextrose in water was injected iv by tail vein per mouse.

Mice: ICR, female, 25 grams.

Immunohistochemical staining to detect CAT protein in lung sections of mice treated in vivo. Procedure: Forty eight hours after injection of the pZN27-DDAB:Chol complexes, the lungs are removed, perfused with 33% O.C.T., embedded in O.C.T. and snap frozen. Frozen tissues are sectioned at 6 microns, collected onto glass slides, fixed for 10 minutes in 4° C. acetone and then placed in 0.2% Triton X-100 to permeabilize membranes. Sections are then incubated for 12–48 hours with the monoclonal anti-CAT antibody (available from Dr. Parker Antin, Univ. of Arizona) or isotype negative control antibody at the appropriate dilution. After washing, 1) a biotinylated antibody directed against the primary antibody (Zymed, S. San Francisco) is added for a minimum of 60 minutes, 2) followed by application of the streptavidin-alkaline phosphatase complex (Zymed) for 60 minutes and 3) application of the substrate-chromogen appropriate for the enzyme label per manufacturers instructions. Slides are then coverslipped in water-soluble mounting media for examination.

Figure 1B:
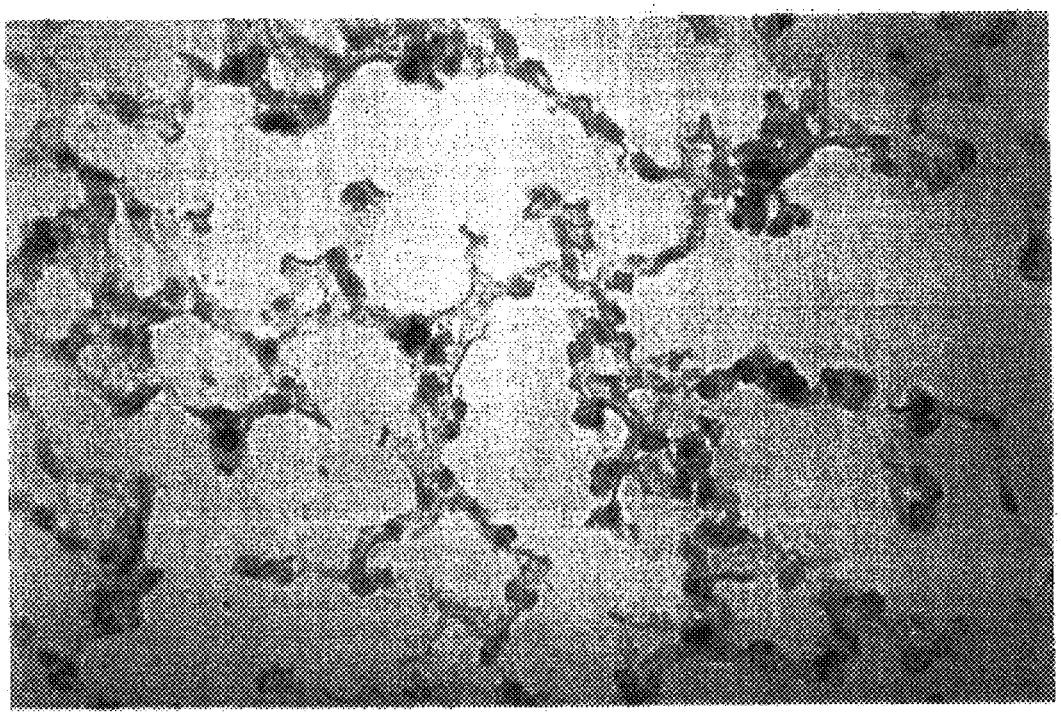

Results:

The results are shown in FIG. 1 and demonstrate diffuse staining of the lung. The stain localizes to the alveolar walls, indication that greater than 70% of pulmonary vascular endothelial cells, as well as alveolar lining cells, including type I and type II cells and alveolar macrophages are transfected by a single iv injection of DNA lipid carrier complexes. In addition, significant numbers of bronchiolar airway lining cells stain positively for CAT protein, and are therefore transfected in vivo by iv injection of lipid carrier:DNA complexes. Thus, the great majority of all cells in the lung are transfected by a iv injection of pZN27-DDAB:CHOL complexes.

Example 4

Expression of pCIS-CAT Following Intraperitoneal Administration

Effect of the Amount of pCIS-CAT-cationic Lipid Carrier Complexes Injected ip on the Level of CAT Gene Expression In Vivo.

Female ICR mice (Simonson Labs, Gilroy, Calif.) were injected ip with 1 ml of 5% dextrose in water containing 0.01, 0.1 or 1 mg of pCIS-CAT expression plasmid complexes to 0.01, 0.1 or 1 moles, respectively of DDAB:DOPE lipid carriers. Mice were sacrificed 48 hours later, the organs removed, and tissues were homogenized in 0.25M Tris-HCl buffer pH 7.8, using a hand-held homogenizer. Cytoplasmic extracts were made, normalized by protein content and level of CAT protein was then measured. The experiments comprise three animals per group and the results show the mean dpm±SEM of acetylated chloramphenicol.

Methods: Lipid carriers containing DDAB were prepared in 1:1 molar ratio with DOPE, as follows: 10 $\mu$moles of DOPE dissolved in chloroform and 10 $\mu$moles of the cationic lipid, dissolved in ethanol were evaporated to dryness on a rotary evaporator. One ml sterile of water was added, and the mixture was sonicated in a bath sonicator (Laboratory Supply, Hicksville, N.Y.) for 20 min. Lipid carriers had mean diameters of approximately 100±25 nm. For CAT assays, cell extracts were made, and their protein content determined by the Coomasie blue assay (BioRad, Richmond, Calif.). One hundred $\mu$g of protein from the lung, spleen, liver, and heart extracts, and 50 $\mu$g of lymph node extract were reacted with $^{14}$C labeled chloramphenicol and chromatographed as previously described (Gorman, supra). To calculate dpm, both the acetylated and unacetylated species were cut from TLC plates and radioactivity counted in a scintillation counter. The ratio between acetylated and unacetylated counts was used to calculate the mean dpm. The mean dpm from tissues of untreated control animals were subtracted from each treated animal for each tissue.

Results:

To assess potential dose-response relationships in vivo, animals were injected in groups of three with 0.01 mg, 0.1 mg, or 1 mg of pCIS-CAT plasmid complexed to 0.01 $\mu$mole, 0.1 $\mu$mole, or 1 $\mu$mole respectively of DDAB:DOPE lipid carriers. Both the 0.1 mg and 1 mg DNA doses produced highly significant levels of CAT protein (p<0.005) in all the organs assayed. Maximal levels of CAT gene expression in each organ were produced by the 1 mg DNA dose: increasing the DNA-lipid carrier dose 10 fold resulted in an approximately 2 fold increase in lymph node CAT levels and a 3 fold increase in the spleen.

Example 5

Demonstration of CAT Gene Expression in the Spleen After Intravenous (iv) Injection of p5'PRL3-CAT:L-PE:CEBA Complexes Lipid carrier: L-PE:CEBA=1:1, stock 20 mM in lipid carrier buffer.

Plasmid: p5'PRL3-CAT.

DNA:Lipid carrier Ratio: lipid carrier:plasmid=1 nanomole cationic lipid: 1 $\mu$g plasmid DNA.

DNA dose: 200 $\mu$g plasmid DNA in 200 $\mu$l 5% dextrose in water was injected by tail vein per mouse.

Mice: BalB/c, female, 25 grams.

Tissue extraction procedure: Forty eight hours after tail vein injection, mice were sacrificed, whole spleen was homogenized in 1 ml of 0.25M Tris-HCl pH 7.8, 5 mM EDTA, 80 $\mu$g/ml PMSF and the resulting extract was centrifuged and then the supernatant was subjected to 3 cycles of freeze-thaw and then heated to 65° C. for 20 min.

CAT assay procedure: 100 $\mu$l of extract+10 $\mu$L of 20 mM acetyl CoA+4 $\mu$l of $^{14}$C-chloramphenicol (25 $\mu$Ci/ml, 55 mCi/mmole, Amersham) were incubated together at 37° C. for 6 hr. At 3 hours, an additional 10 $\mu$l of acetyl CoA was added.

Figure 14:
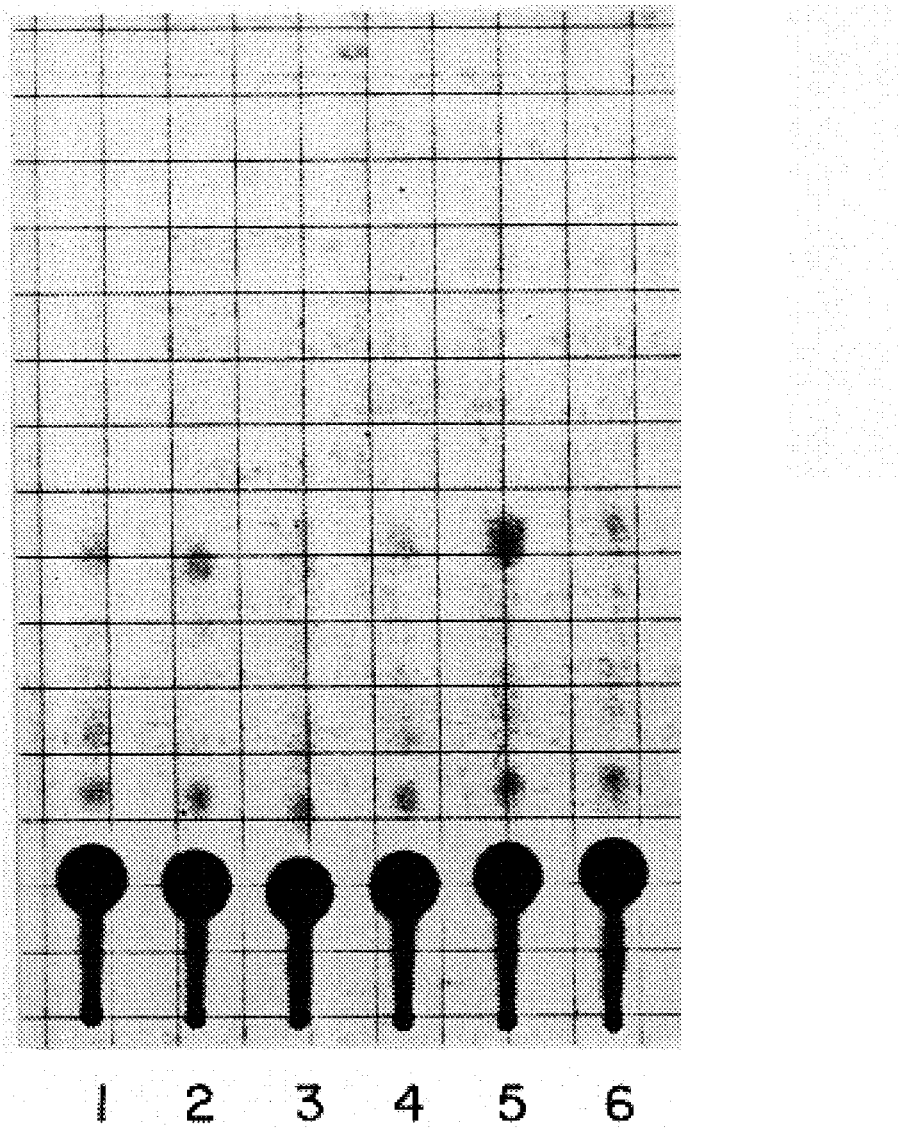
FIG. 14 is a photomicrograph showing CAT expression in spleen after intravenous injection of p5'PRL3-CAT:L-PE:CEBA complexes. Lipid carriers were 1 to 1 molar L-PE:CEBA. Lipid carrier-DNA complexes were 1 nanomole cationic lipid to 1 $\mu$g DNA. 200 $\mu$g DNA was injected per mouse. The chromatograph was run from bottom to top of the Figure as shown.

Results:

The results are shown in FIG. 14, lane 2 (lipid carriers only) and lane 5 (lipid carrier-DNA complex), and indicate that a significant level of CAT activity is present in the spleen extract of the treated animal, but not in the extract of control spleen, taken from an animal injected with lipid carrier alone.

Demonstration of CAT Gene Expression in the Lung After Intravenous (iv) Injection of PRSV-CAT:L-PE:CEBA Complexes.

Lipid carrier: L-PE: CEBA=1:1, stock 20 mM in lipid carrier buffer.

Plasmid: pRSV-CAT.

DNA:Lipid carrier Ratio: lipid carrier:plasmid=1 nanomole cationic lipid: 1 $\mu$g plasmid DNA.

DNA dose: 100 $\mu$g plasmid DNA in 200 $\mu$l 5% dextrose in water was injected by tail vein per mouse.

Mice: BalB/c, female, 25 grams.

Tissue extraction procedure: Forty eight hours after tail vein injection, the animals were sacrificed, whole lung was homogenized in 1 ml of 0.25M Tris-HCl pH 7.8, 5 mM EDTA, 80 $\mu$g /ml PMSF and the resulting extract was centrifuged and then the supernatant was subjected to 3 cycles of freeze-thaw and then heated to 65° C. for 20 min.

CAT assay procedure: 100 $\mu$l of extract+10 $\mu$l of 20 mM acetyl CoA+4 $\mu$l of $^{14}$C-chloramphenicol (25 $\mu$Ci/ml, 55 mCi/mmole, Amersham) were incubated together at 37° C. for 6 hr. At 3 hours, an additional 10 $\mu$l of acetyl CoA was added.

Figure 15:
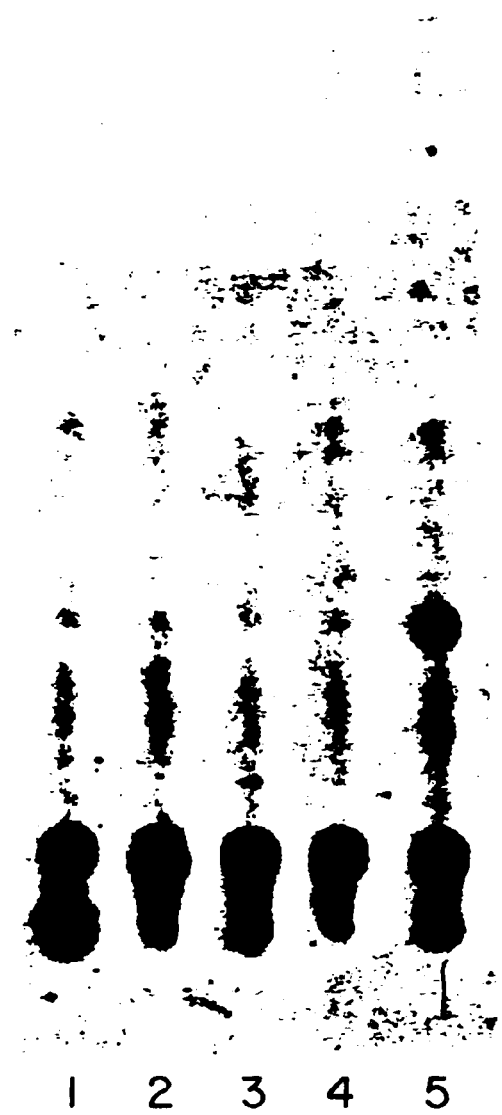
FIG. 15 is a photomicrograph showing CAT expression in the lung after intravenous injection of pRSV-CAT:L-PE:CEBA complexes. Lanes 1–3 are samples from untreated mouse lung; lane 4 is from a lung sample from a mouse treated with lipid carriers only; lane 5 is a sample from a mouse treated with the lipid carrier-DNA complex. Lipid carriers were 1 to 1 molar L-PE:CEBA. Lipid carrier-DNA complexes were 1 nanomole cationic lipid to 1 $\mu$g DNA. 100 $\mu$g DNA was injected per mouse. The chromatograph runs from bottom to top of the Figure as shown.

Results:

The results are shown in FIG. 15, and indicate that a significant level of CAT activity (indicative of expression of the transgene) was present in the lung of the animal injected with lipid carrier:DNA complexes (lane 5), but not present in the lungs from control animals (lanes 1–4).

Demonstration of CAT Gene Expression in Multiple Tissues After Intravenous (iv) Injection of pZN20-CAT:DDAB:DOPE Complexes.

Lipid carrier: DDAB:DOPE=1:1, stock 10 mM in 5% dextrose.

Plasmid: pZN20.

DNA:Lipid carrier Ratio: lipid carrier:plasmid=(A) 3 nanomole cationic lipid: 1 μg plasmid DNA (SUV). (B) 6 nanomole cationic lipid: 1 μg plasmid DNA (MLV).

DNA dose: 100 μg plasmid DNA in 200 μl 5% dextrose in water was injected by tail vein per mouse. Three mice each received this dose of MLV:pZN20 and 3 mice each this dose of SUV:pZN20.

Tissue extraction procedure: each organ was homogenized in 0.3 ml of 0.25 M Tris-HCl pH 7.8, 5 mM EDTA, and the resulting extract was centrifuged and then the supernatant was subjected to 3 cycles of freeze-thaw and then heated to 65° C. for 20 min.

CAT assay procedure: the protein concentration of each tissue extract was quantitated using a Coomasie blue-based protein assay (Bio-Rad, Richmond, Calif.), and the same amount of total protein from each tissue extract was added in the CAT assay, together with 10 μl of 20 mM acetyl CoA+12 μl of $^{14}$C-chloramphenicol (25 μCi/ml, 55 mCi/mmole, Amersham), at 37° C. for 13 hrs.

Figure 8:
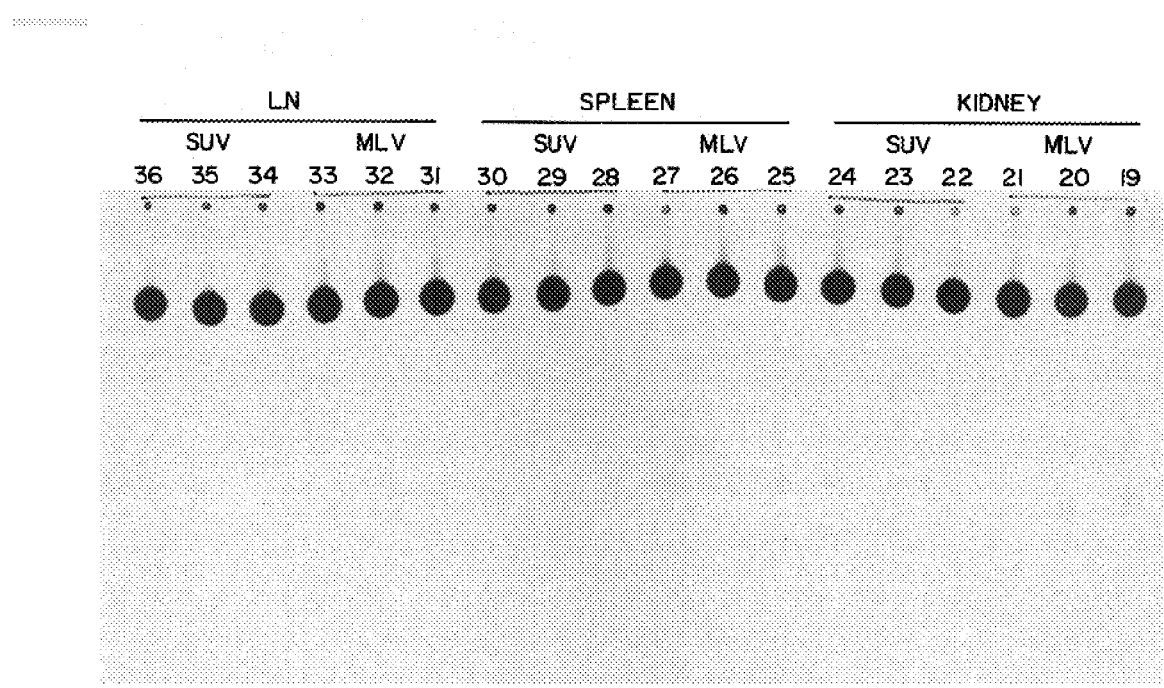
FIG. 8 shows CAT gene expression in the indicated tissues following intravenous injection of pZN20:DDAB:DOPE complexes. The lipid carrier was DDAB:DOPE 1 to 1 molar ratio. Two lipid carrier-to-plasmid ratios (nanomoles cationic lipid: µg plasmid DNA) were used, MLV, 6:1 and SUV, 3:1. Lanes 1–6 are samples from lung tissue; lanes 7–12, heart tissue; lanes 13–18, liver; lanes 19–24, kidney; lanes 25–30, spleen; lanes 31–36, lymph nodes. The first 3 samples of each tissue set were from animals injected with MLV, the next 3 samples of each tissue set were from animals injected with SUV. In lanes 1–18 the chromatograph runs from bottom to top, in lanes 19–36 the chromatograph runs from top to bottom. These results demonstrate that iv injection of pZN20:DDAB:DOPE complexes produces significant levels of CAT gene expression in six different tissues. Furthermore, MLV appear to mediate equal or greater levels of in vivo gene expression than do SUV composed of the same lipids. Construction of pZN20 is shown in FIG. 5.
Figure 8:
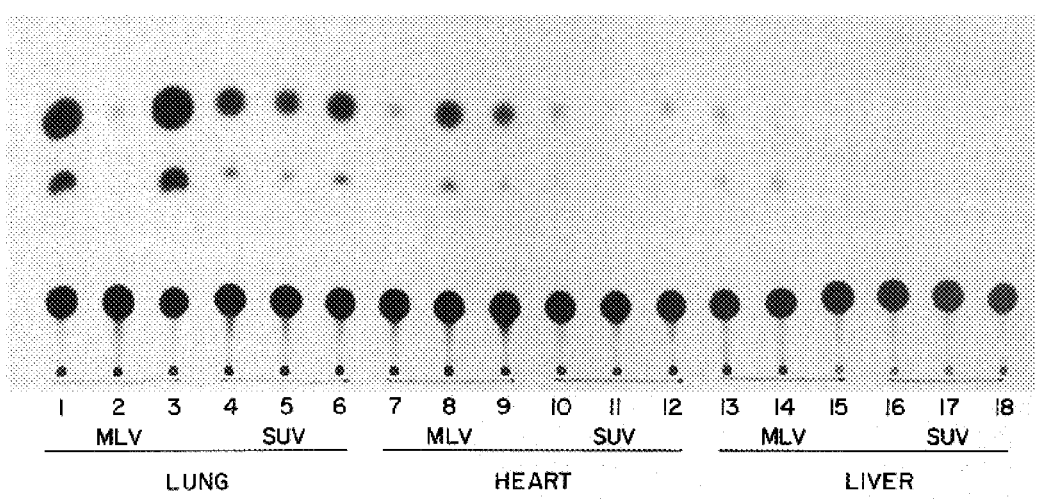

Results:

The results are shown in FIG. 8, and demonstrate that iv injection of pZN20:DDAB:DOPE complexes results in significant levels of CAT gene expression in each of 6 different tissues including lung, heart, liver, spleen, kidney and lymph nodes. Furthermore, MLV lipid carriers mediate equal or higher levels of in vivo transgene expression than do SUV lipid carriers composed of the same lipids.

Demonstration of CAT Gene Expression In Vivo After Intravenous (iv) Injection of pZN20 alone.

Plasmid: pZN20.

DNA:Lipid carrier Ratio: Plasmid DNA alone, without lipid carriers, was injected.

DNA dose: 300 μg plasmid DNA in 200 μl 5% dextrose in water was injected by tail vein per mouse.

Mice: ICR, female, 25 grams.

Tissue extraction procedure: each organ was homogenized in 0.3 ml of 0.25M Tri-HCl pH 7.8, 5 mM EDTA, and the resulting extract was centrifuged and then subjected to 3 cycles of freeze-thaw and then heated to 65° C. for 20 min.

CAT assay procedure: the protein concentration of each tissue extract was quantitated using a ninhydrin-based protein assay (Bio-Rad, Richmond, Calif.), and same amount of total protein from each tissue extract was added in the CAT assay, together with 10 μl of 20 mM acetyl CoA+12 μl of $^{14}$C-chloramphenicol (25 μCi/ml, 55 mCi/mmole, Amersham) at 37° C. for 13 hrs.

Example 6

Injection of DOTMA:DOPE+pSIS-CAT Plasmid Clearly Did Not Produce Detectable CAT Gene Expression In Vivo Lipid carrier: DOTMA:DOPE=1:1, in 5% dextrose in water Plasmid: pSIS-CAT (Huang, M. T. F. and C. M. Gorman, 1990, *Nucleic Acids Research* 18:937–947).

Ratio: Cationic lipid:plasmid=4 nmoles: 1 μg, dose: 100 μg DNA in 200 μl 5% dextrose in water.

Mouse: ICR, female, 25 grams.

Injection: tail vein.

Tissue Collection and Processing:

Mice were sacrificed at day 2 and day 6, and lung, spleen, liver, and heart were collected. The whole organs were homogenized in 0.5 ml, except livers which were homogenized in 2.0 ml, of 0.25M Tris-HCl pH 7.8, 5 mM EDTA, 2 μg/ml aprotinin, 1 μg/ml E-64, and 0.5 μg/ml leupeptin (all protease inhibitors were purchased from Boehringer Mannheim). Extracts were subjected to three cycles of freeze-thaw, then heated to 65° C. for 10 min.

CAT assay: 100 μl of extracts for each assay with 0.3 μCi of $^{14}$C-chloramphenicol and 10 μl of 20 mM acetyl CoA at 37° C. for either 5 hrs or 24.5 hrs, and the materials were then extracted using ethyl acetate and analyzed on TLC plates.

Results:

There were no acetylated chloramphenicol species presented as determined by comparing the extracts from treated animals with that from control animals. Thus, under similar experimental conditions that produce high level expression of pZN27, the use of the pSIS-CAT expression vector does not result in any detectable expression of the linked-CAT gene in any of the tissues assayed in vivo. The lack of expression of pSIS-CAT in vivo may be due either to a different promoter-enhancer element (SV40) or to a different intron sequence when compared to the pZN27 vector, which yields high level in vivo expression.

Figure 9A:
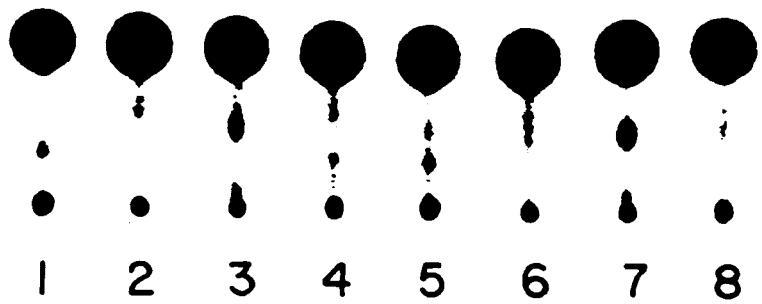
FIGS. 9A and 9B show the results of iv injection of DOTMA:DOPE complexed to pSIS-CAT; the plasmid does not produce detectable CAT expression in vivo.
Figure 9B:
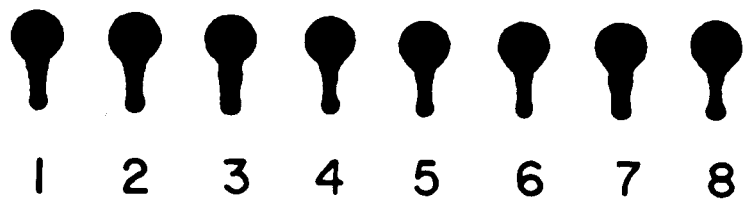

The results are shown in FIG. 9.

Example 7

Interaction of DNA:Lipid Carrier Complexes With Cell Surface Receptors

Cells and cell culture: CV-1 (African green monkey kidney), U937 (human myelocytic leukemia), murine erythroleukemia (MEL) cells, and K562 cells (human erythroleukemia cells were obtained from the American Type Culture Collection (Rockville, Md.). CV-1 and MEL cells were maintained in Dulbecco minimum essential medium (DME)-H-21 with 5% fetal bovine serum (FBS) at 37° C. and 7% $CO_2$. Rat alveolar type II cells and rat alveolar macrophages were isolated and purified as previously described. (Debs et al., *Amer. Rev. Respiratory Disease* (1987) 135:731–737; Dobbs, L. *Amer. Rev. Respiratory Disease* (1986) 134:141–145). Type II cells were maintained in DME-H-16 with 5% FBS at 37° C. and 7% $CO_2$. Twenty nanomoles of DOTMA:DOPE lipid carriers complexed to 20 μg of pRSV-CAT plasmid DNA were added to 2 million cells growing in 60 mm Falcon plastic dishes (either SUV or MLV), and fixed for EM at time points from 15 minutes to 2 hours thereafter.

Fixation and Processing for Electron Microscopy

DOTMA lipid carriers and cells in tissue culture or freshly isolated from blood or pulmonary alveoli were fixed in 1.5% glutaraldehyde in 0.1 molar sodium cacodylate buffeir containing 1% sucrose, pH 7.4, at room temperature for 1 hr. Following tannic acid and uranyl acetate enhancement, tissue was dehydrated in a graded series of alcohols and embedded in epoxy 812 resin (Ernest F. Fullam, Inc., Latham, N.Y.) sectioned on an MT 2 microtome using diamond knives and examined with a Jeol 100CX transmission electronmicroscope operating at 80 kv. The results are shown in FIG. 7.

The most frequent interaction between DOTMA lipid carriers, either uni- or multilammelar lipid carriers, complexed to plasmid DNA and the various cell types (CV-1 monkey kidney cells, U937 human myelomonocytic leukemia cells, K562, MEL erythroblastic leukemia cells, rat alveolar macrophages, and alveolar type II cells), is that of lipid carrier adhesion and internalization in a typical coated vesicle pathway (FIGS. 7a–f). This interaction is common to well defined examples of receptor-mediated endocytosis. All cells which appear to have contacted cationic lipid carrier:DNA complexes ingest the complexes after binding to the plasma membrane. All these cell types (derived from rodent, monkey and human cells, demonstrate the same classical receptor-mediated endocytic pathway of internalization. DNA-cationic liposome complexes are generally taken up by human cells as well as or better than nonhuman and particularly rodent cells of similar lineage.

Example 8

Demonstration That Mouse T Lymphocytes are Transfected In Vivo

Figure 2A:
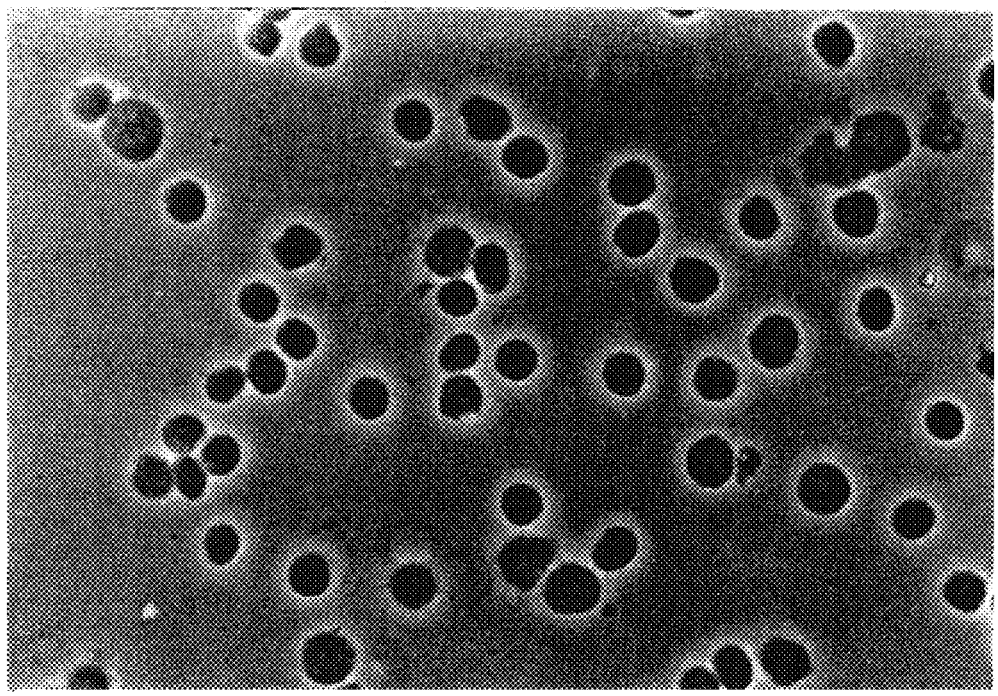
FIG. 2A shows a phase contrast micrograph of mouse T lymphocytes isolated 48 hours after intraperitoneal (ip) injection of DNA-cationic lipid carrier complexes. Lipid carriers were DDAB:DOPE, 1 to 1 molar. DNA-cationic lipid carrier complexes were 1 mg pCIS-CAT with 1 µmole cationic lipid. 1 mg DNA was injected ip.
Figure 2B:
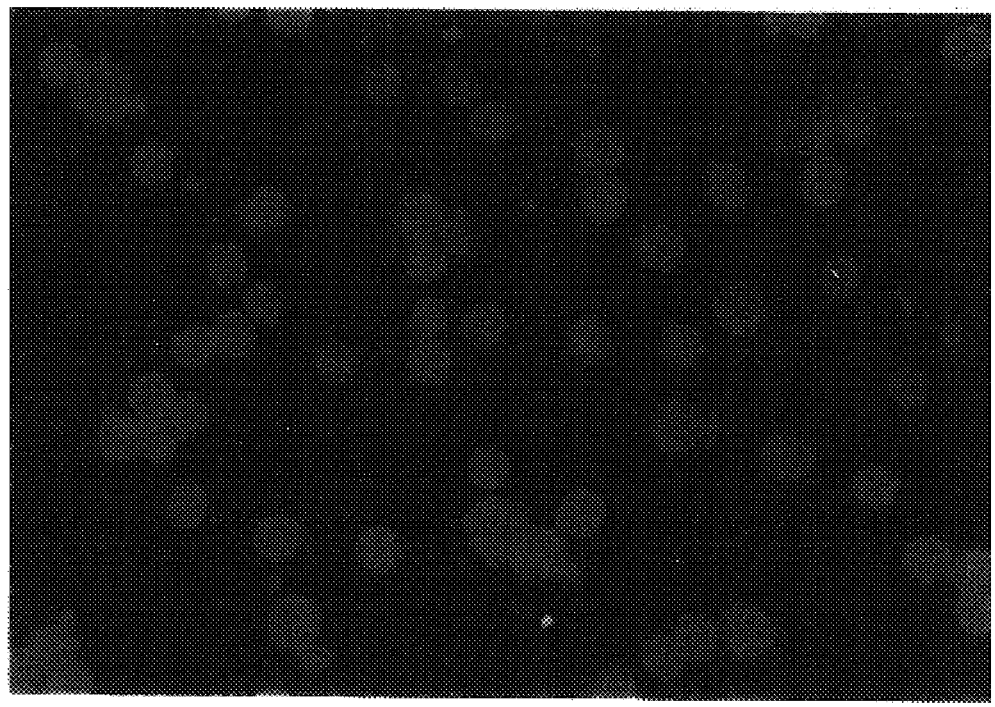
FIG. 2B shows a fluorescence micrograph showing that essentially all T lymphocytes present were transfected following ip injection of DNA/cationic lipid carrier complexes.
Figure 3:
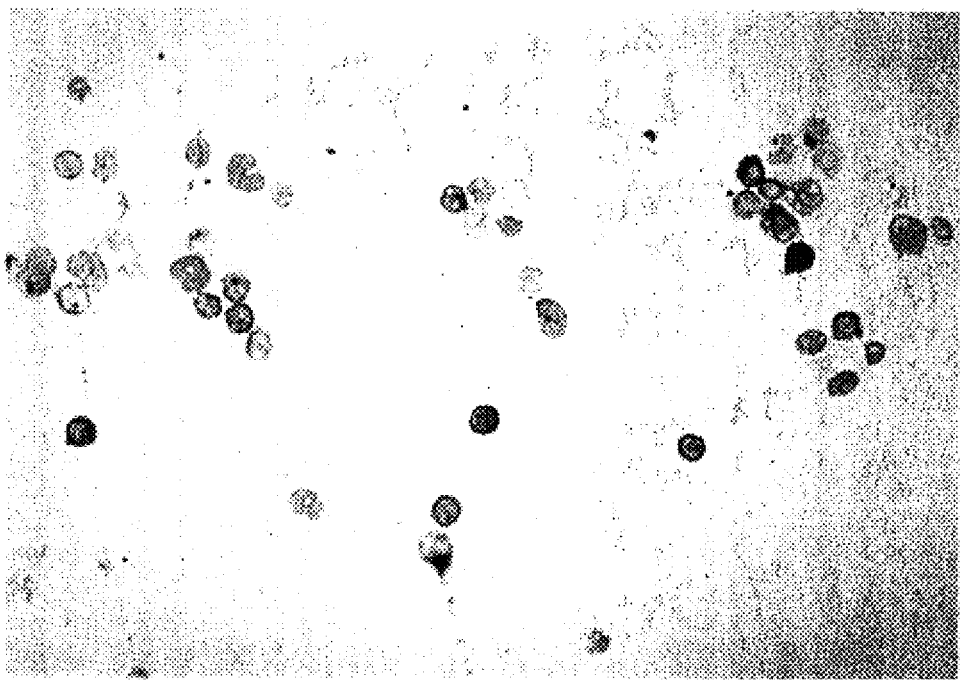
FIG. 3 shows hematopoietic bone marrow-derived cells from a mouse treated with a DNA:lipid carrier complex DDAB:DOPE:pCIS-CAT intraperitoneally 48 hours earlier. The photomicrograph shows that approximately 20 percent of the bone marrow-derived cells, including primitive or blast cells, are transfected in vivo. Lipid carriers were 1:1 DDAB:DOPE. DNA:cationic lipid ratio was 1 mg DNA to 1 µmole cationic lipid. 1 mg DNA was injected ip into each mouse.

Female ICR mice (Simonson Labs, Gilroy, Calif.) were injected ip with 1 ml of 5% dextrose in water containing 1 mg of a pZN27 plasmid complexed to 1 μmole of DDAB:DOPE (1:1 molar, SUV) lipid carriers. Mice were sacrificed 48 hrs. later, the spleen and lymph nodes were removed, and rendered into single cell suspensions by homogenizing in serum containing medium. The cells were then incubated with FITC-conjugated anti-Thy 1.2 antibody (provided by Dr. J. Beck, San Francisco Veterans Administration Medical Center) and FACS sorted. The Thy $1.2^+$ T lymphocyte fraction was cytospun onto microscope slides and fixed and probed for the presence of intracellular CAT protein after permeabilizing the cells using 0.25% Triton x-100. The cells were incubated with an anti-CAT monoclonal antibody (gift from Dr. P. Antin, Univ. of Arizona) for 1 hr. at 20° C. and then stained with a Texas Red conjugated goat-anti-mouse IgG for 1 hr. at 20° C. FIG. 2A shows a field of T lymphocytes by phase contrast microscopy and 2B shows the same field viewed by fluorescence microscopy. These results demonstrate that more than 70% of Thy$1.2^+$ T lymphocytes are transfected in vivo by a single ip injection of pZN27:DDAB:DOPE complexes. Thy$1.2^+$ lymphocytes from untreated mice do not show immunofluorescent staining.

Example 9

Demonstration That Mouse Hematopoietic Bone Marrow-Derived Cells are Transfected In Vivo Female ICR mice (Simonson Labs, Gilroy, Calif.) were injected ip with 1 ml of 5% dextrose in water containing 1 mg of a pZN27 plasmid complexed to 1 μmole of DDAB-:DOPE SUV lipid carriers. Mice were sacrificed 48 hrs. later, bone marrow-derived hematopoietic cells were then obtained by perfusing the femur cavity with RPMI-1640 medium and then homogenizing clumps to obtain a single cell suspension. Bone marrow cells were then centrifuged onto glass slides and fluorescently stained as described in Example 8. These results demonstrate that approximately 20% of mouse bone marrow hematopoietic cells (including cells that on the basis of morphology are primitive myeloblastic and erythroblastic precursor cells) are transfected in vivo by a single ip dose of pZN27:DDAB:DOPE complexes.

Example 10

Demonstration That Human $CD4^+$ T Lymphocytes, Freshly Isolated From Normal Donors, are Transfected In Vitro Buffy coat preparations were freshly isolated from normal human donors by gradient centrifugation. The cells were then panned using an anti-CD3 (Becton-Dickinson, Mountain View, Calif.) monoclonal antibody to isolate the $CD3^+$ T lymphocyte fraction. These cells were then transfected using the following protocol: 10 million cells were plated on 100 mm dishes and then 25 μg of pZN27 complexed to 50 μmoles of DDAB:DOPE (1/1) SUV lipid carriers were added for 48 hours. The cells were then incubated with a FITC-conjugated monoclonal anti-CD4 antibody (Becton-Dickinson) and FACS sorted. The resulting $CD4^+$ T lymphocytes were cytospun onto microscope slides and fixed and probed for the presence of intracellular CAT protein after permeabilizing the cells using 0.25% Triton x-100. The cells were incubated with an anti-CAT monoclonal antibody (gift from Dr. P. Antin, University of Arizona) for 1 hr at 20° C. and then stained with a Texas Red conjugated goat anti-mouse IgG for 1 hr at 20° C.

Figure 4A:
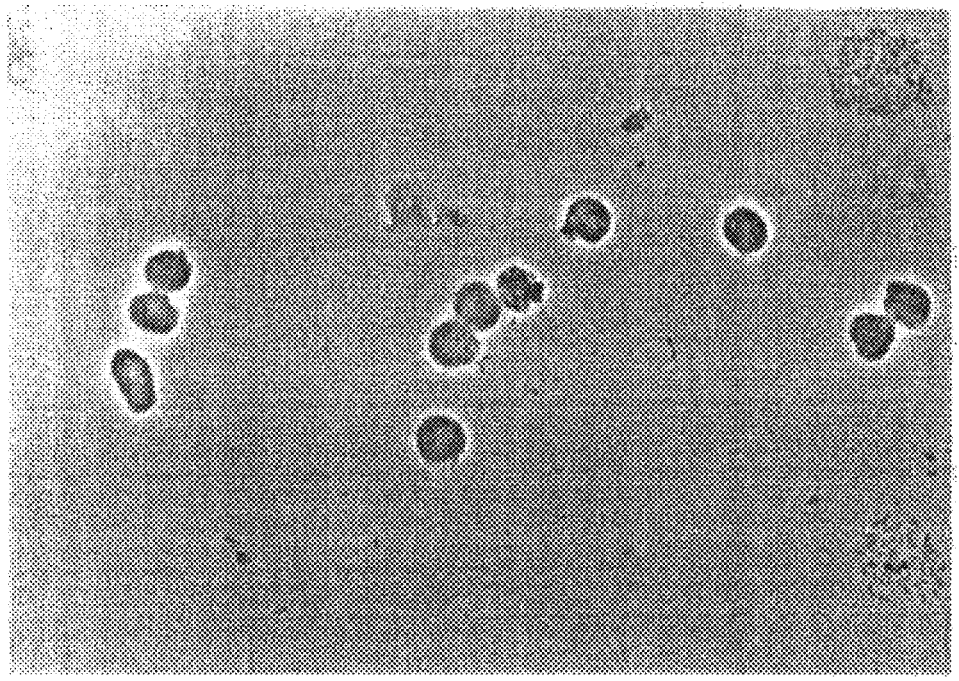
FIGS. 4A and 4B show transfection of human T lymphocytes (CD4$^+$) by CAT expression plasmid-DNA complexes in culture. The lipid carrier composition was 1:1 molar ratio DDAB:DOPE (SUV). 25 µg of pZN27 complexed with 50 nmoles cationic lipid was added to 10 million cells in culture.
Figure 4B:
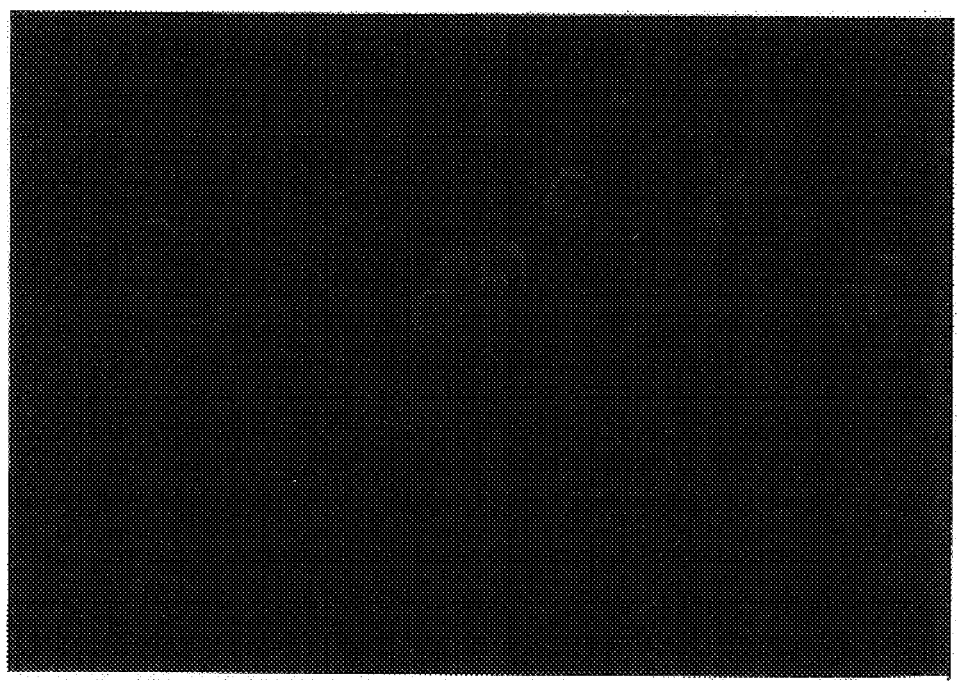
Figure 5A:
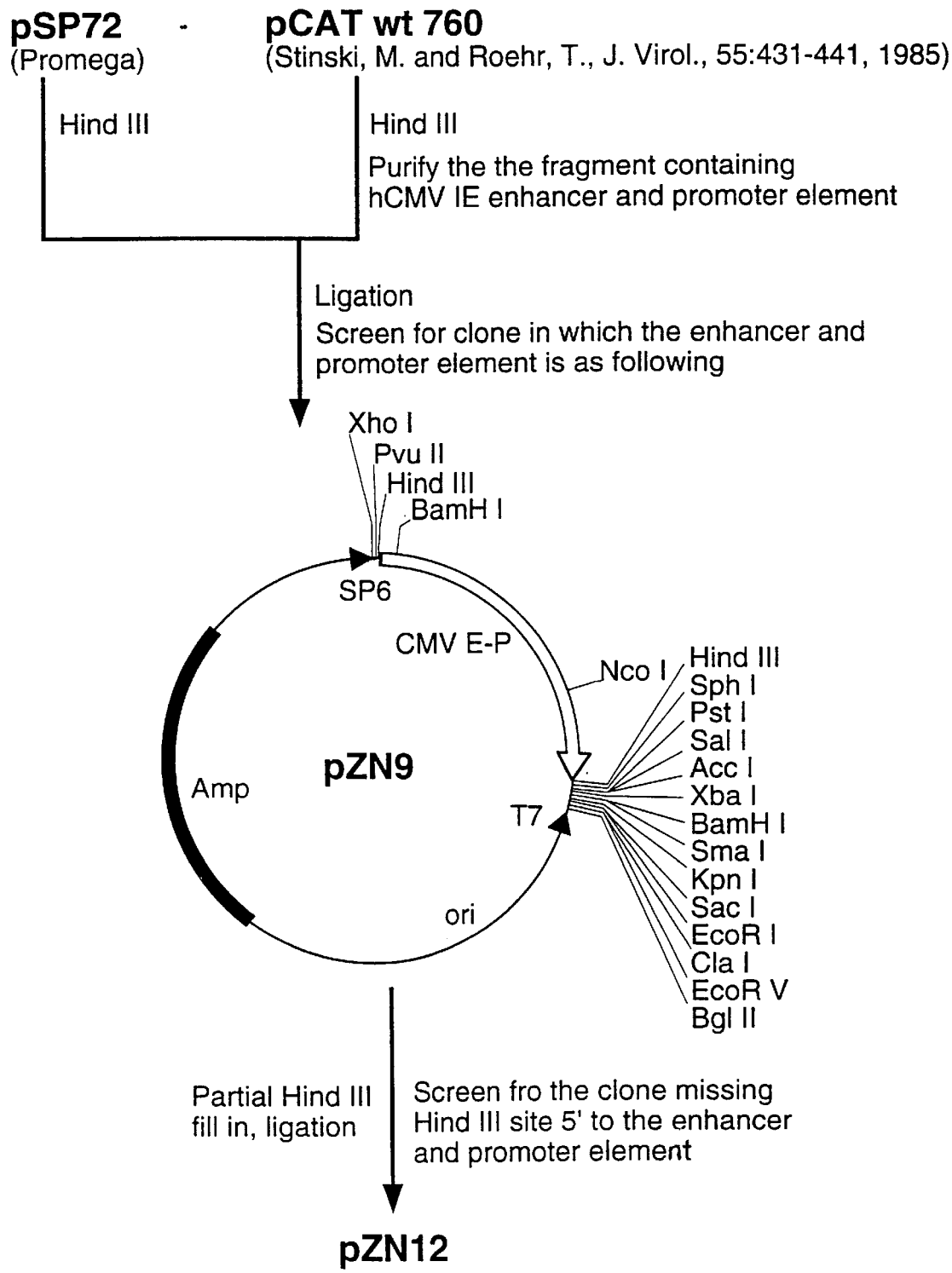
FIGS. 5A–5D show construction of plasmid pZN20.
Figure 5B:
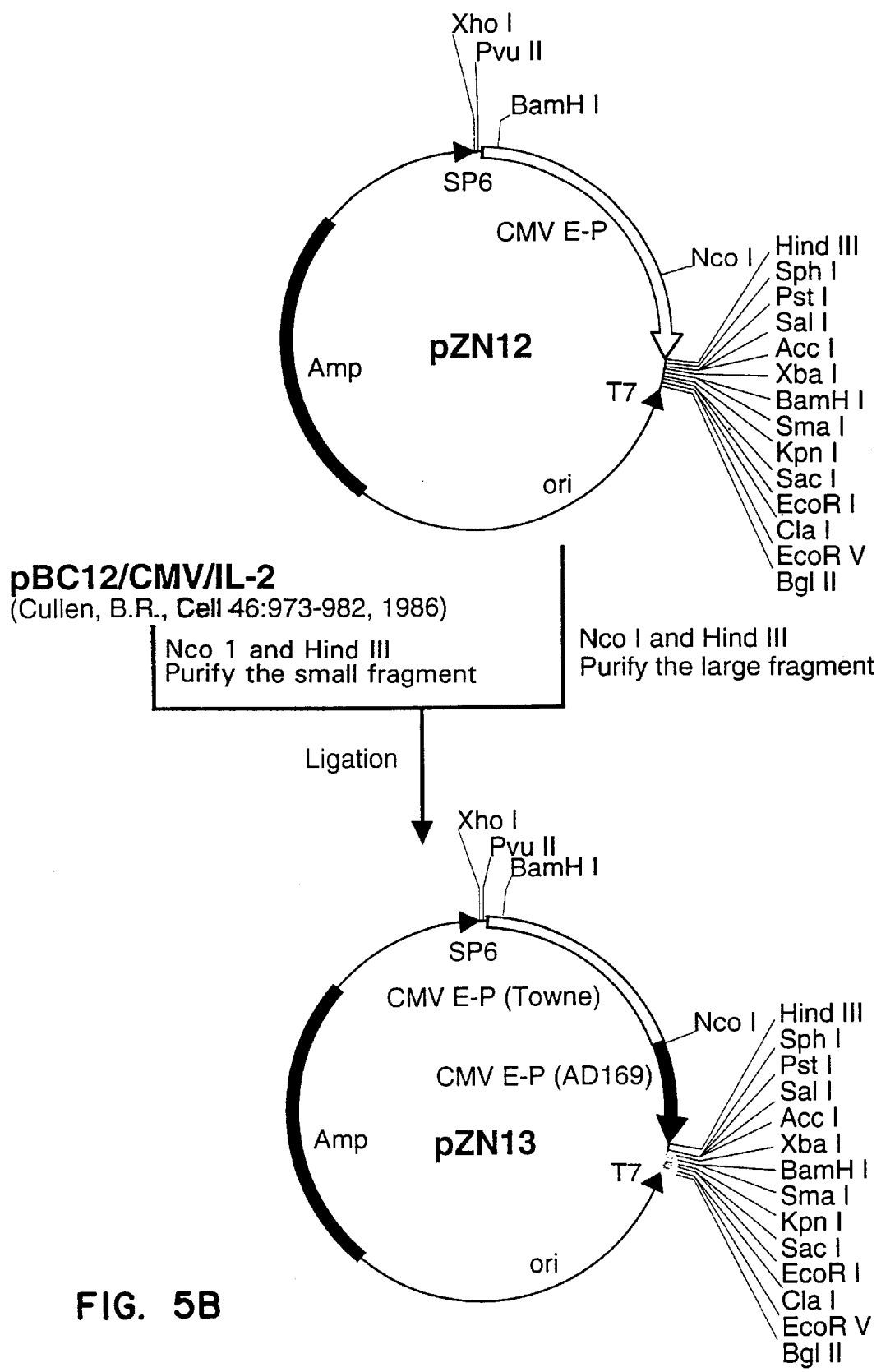
Figure 5C:
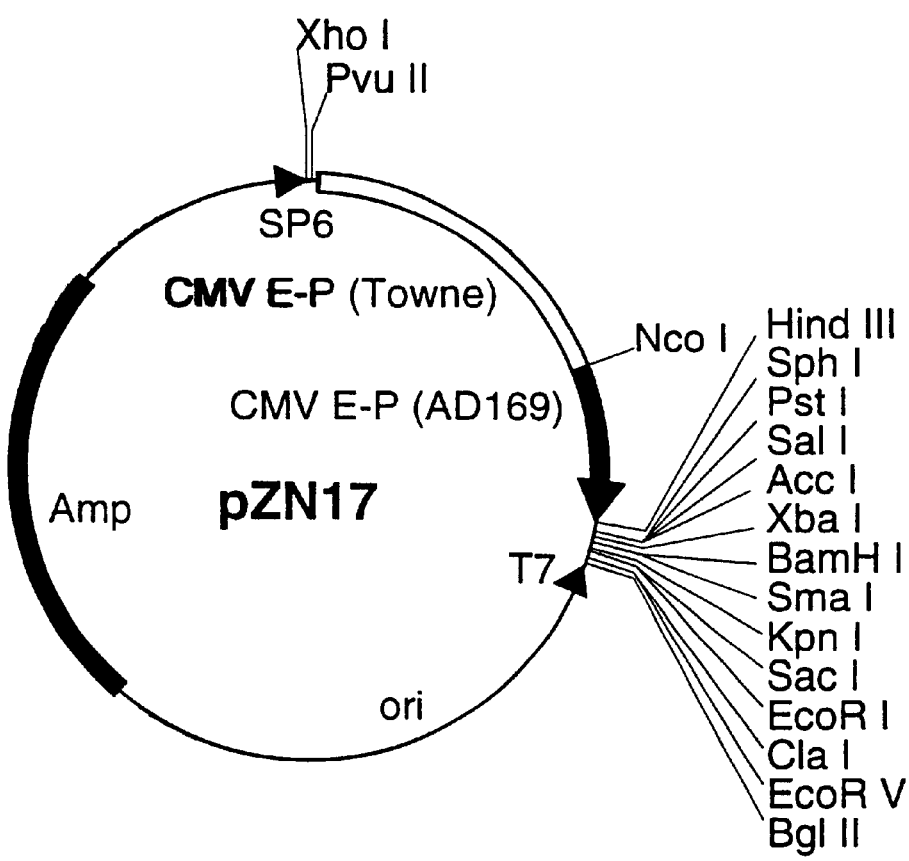
Figure 5D:
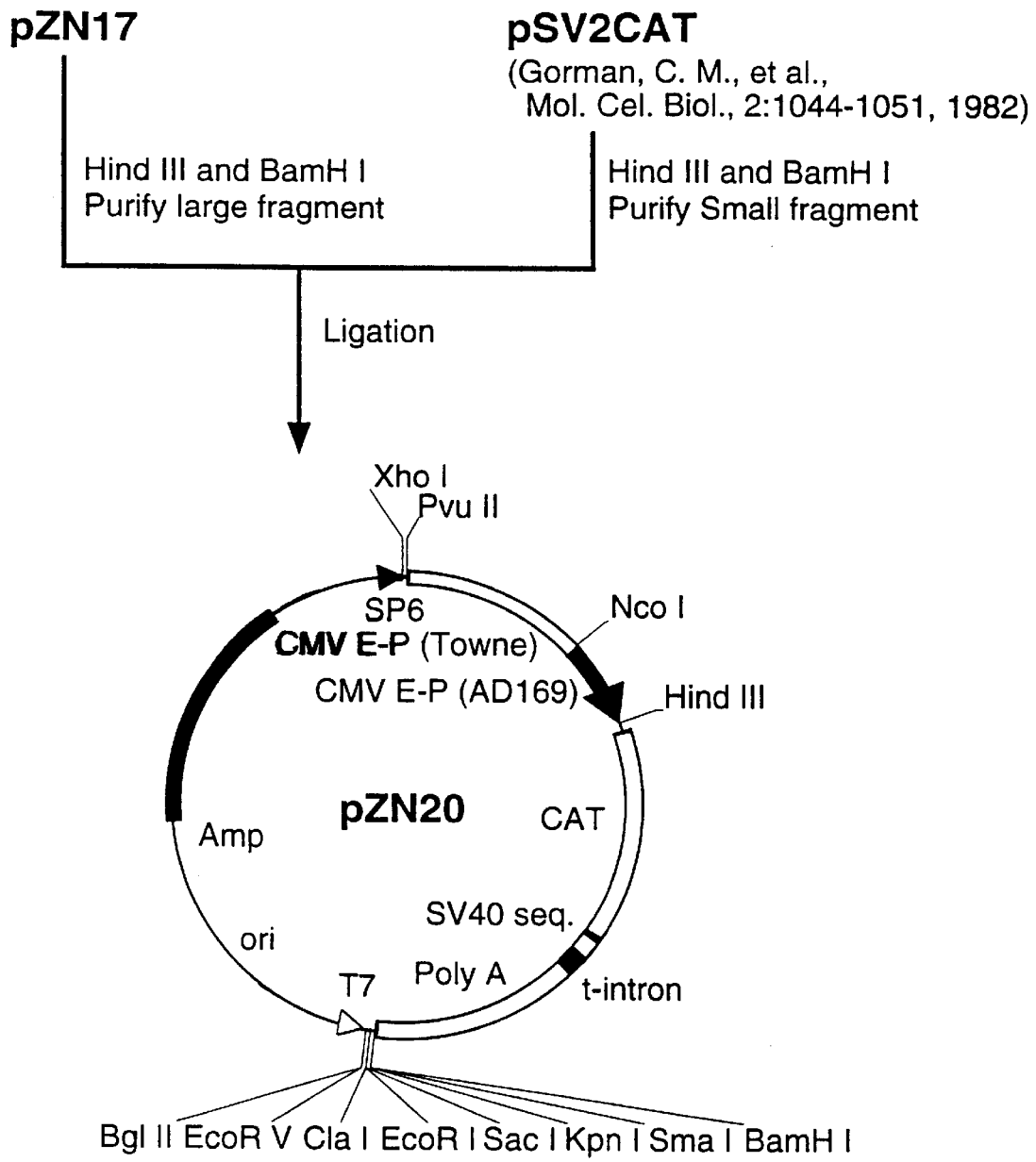

Results:

Results are shown in FIG. 4 and demonstrate that at least 70% of freshly isolated human $CD4^+$ T lymphocytes are transfected after exposure to pZN27:DDAB:DOPE complexes in culture. These results suggest that this approach may dramatically improve the therapy of diseases including AIDS and cancer.

As the above results show, high level transgene expression has been achieved in heart, kidney, lymph nodes, bone marrow cells, liver, lung and spleen after systemic (iv or ip) transgene administration. Transfection of the heart, kidney, lymph nodes or bone marrow cells individually after systemic (iv or ip) transgene administration into adults has not previously been accomplished. Transfection of T lymphocytes, lung airway or alveolar cell types, cardiac endothelial lining cells and cardiac muscle cells, and bone marrow hematopoietic precursor cells in vivo by systemic administration of DNA has not been shown previously. Specifically, greater than 50% of T lymphocytes, lung airway epithelial, alveolar and vascular endothelial cell types, cardiac endothelial lining cells and bone marrow hematopoietic precursor cells (including about 70% of blast cells) are transfected in vivo, following one iv or ip injection of CAT expression plasmid-cationic lipid carrier complexes. Transfection of a high percentage of all the cells present in any single tissue has not been reported previously.

Example 11

Efficient Transfection of a Variety of Human Lung Cancer Cell Lines Using Cationic Liposome-mediated Delivery of DNA Method:

Cell Culture: NCl-H69, NCI-H82, and NCI-H520. H69 and H520 cells were grown in RPMI-1640 with 10% fetal bovine serum (FBS) and H82 cells were grown in Dulbecco's minimum essential medium (DME)-H21 with 10% FBS.

Liposome preparation: Liposomes were prepared as follows: a total of 4 μmoles of lipid dissolved in chloroform, (or in ethanol (DOTMA)) were evaporated to dryness on a rotary evaporator. One ml of 50 mM Tris, 0.5 mM EDTA, 50 mM NaCl, 100 mM $ZnCl_2$ buffer per 20 mmoles of lipid was added, and the mixture was sonicated in a bath sonicator (Laboratory Supply Co., Hicksville, N.Y.) for 20 min. The resulting liposomes have an approximate mean diameter of 100±25 nm. The following liposome preparations were used: pure DOTMA, DOTMA:chol in a 2 to 1 molar ratio, pure L-PE or L-PE:chol-b-ala in a 6 to 4 molar ratio.

Cellular transfection: For transfection of cells, $2\times10^6$ cells in 4 ml of serum-free medium were plated in 100 mm plastic petri dishes (Falcon, Oxnard, Calif.). The plasmid DNA-liposome complex was prepared by first adding 1) DNA and then 2), liposomes and mixing gently. The complex was then suspended in 1 ml of serum-free medium and added to the cells. Four hours later, the cells were washed twice, resuspended in 10 ml of serum-containing medium, and subsequently harvested, 44 hours later. Just prior to harvesting, the cells were washed 2 times, and the plates were then scraped with a rubber policeman. The cells were centrifuged at 1,000×g for 5 min, and 0.135 ml of 0.25M Tris buffer was added to each pellet. The cells were freeze-thawed 3×, heated at 65° C. for 10 min, and spun at 12,500×g for 10 min. The supernatant was assayed for protein and 20 µg of supernatant protein per sample was used to measure CAT activity, as described in FIG. 7.

Figure 26:
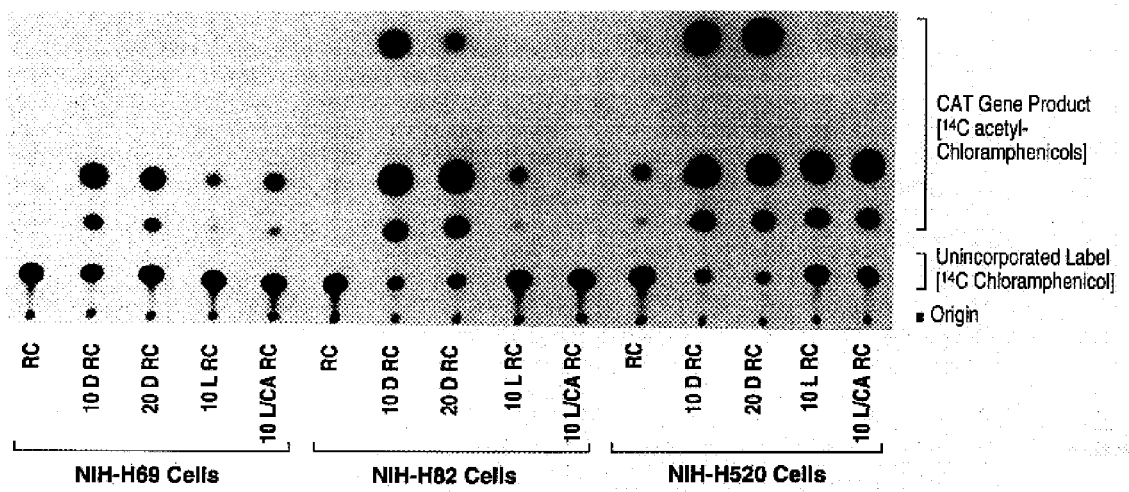
FIG. 26 shows human lung cancer cell line transfections. Autoradiograph of a TLC plate showing CAT activity in extracts from three different human lung cancer cell lines transfected using various cationic liposomes. The lung cancer cell lines NCI-H69,—H82, and -H520 were plated at $2 \times 10_{E6}$ cells/plate and transfected in suspension. Individual plates of cells were transfected with 5 $\mu$g of RSV-CAT (RC) alone or 5 $\mu$g of RSV-CAT complexed to a total of 10 or 20 nmol of pure DOTMA (D), pure L-PE(L), or L-PE/chol-β-ala (L/CA) liposomes. The cells were harvested 48 h after transfection and assayed for CAT activity.

Results: The results demonstrate the ability of cationic liposomes to mediate high level transfection of two different human small cell lung cancer lines (H-69 and H-82) and a squamous cell lung cancer line (H-520). All three lines were very efficiently transfected by RSV-CAT when complexed to 3 different cationic liposome formulations (FIG. 26). These human cell lines were either as or more efficiently transfected than rodent tumor cell lines transfected under comparable conditions.

Example 12

Transfection of Lung Cancers in Mice by Intravenous Injection of Cationic Lipid Carrier:DNA Complexes Mouse: C57/black 6, female, 25 grams.

Cancer: B16, mouse melanoma line which is highly metastatic to lung. The cell line was grown in RPMI 1640 medium supplemented with 5% fetal calf serum.

Lipid carrier: DOTAP:Chol=1.1, 10 mM in 5% dextrose in water.

Plasmid: pZN20.

Ratio: Cationic lipid:DNA=6 nmoles: 1 µg, 100 µg in 200 µl of 5% dextrose in water were injected by tail vein into each mouse.

Inoculation of Cancer Cell Line Into Mice and Administration of CAT Expression Plasmid-cationic Lipid Carrier Complexes:

B16 cells were trypsinized off the plates and 50,000 cells were inoculated into each mouse by intravenous injection into the tail vein. Two weeks after injection, cationic lipid carrier-DNA complexes were injected via tail vein. Lungs were collected 48 hours postinjection, infused with 33% O.C.T., frozen in a dry ice-ethanol bath, cryosectioned, and processed for immunohistochemical analysis to detect intracellular CAT protein.

Immunohistochemical analysis: Procedure:

Organs are removed, appropriately trimmed, embedded in OCT and snap frozen. Frozen tissues are sectioned at 6 microns, collected onto glass slides, fixed for 10 minutes in 4° C. acetone and then placed in 0.2% Triton X-100 to permeabilize membranes. Sections are then incubated for 12–48 hours with the monoclonal anti-CAT antibody (from Dr. P. Antin, University of Arizona) or isotype negative control antibody at the appropriate dilution. After washing, (1) a biotinylated antibody directed against the primary antibody (Zymed, S. San Francisco, Calif.) is added for a minimum of 60 minutes (2) followed by application of the streptavidin-peroxidase complex (Zymed) for 60 minutes and (3) application of the substrate-chromogen appropriate for the enzyme label used. Slides can then be counter-stained in dilute hematoxylin or left unstained and coverslipped in water soluble mounting media for examination.

Results:

Immunohistochemical analysis that B-16 melanoma lung tumors as well as intravascular tumor emboli are efficiently transfected after iv injection of DNA-lipid carrier complexes. Both lung tumors and intravascular tumor emboli show intense staining, indicating efficient, ageneralized transfection in vivo. Tumor bearing mice, which did not receive an injection of DNA-lipid carrier complexes, show no CAT activity in the lung or in any lung tumor cells (FIG. 10B). The ability to transfect tumors present within mammalian hosts by systemic administration of a cloned gene has not previously been demonstrated.

Example 13

Demonstration of High Level CAT Gene Expression in Multiple Tissues After Intravenous (iv) Injection of pZN27 Alone, or pZN27:DDAB:cholesterol SUV Complexes Lipid carrier: DDAB:Chol=1:1, stock 10 mM in 5% dextrose. After addition of 5% dextrose to the dried lipid film, the SUV were prepared by sonication in a bath sonicator for 20 minutes.

Plasmid: pZN27.

DNA:Lipid carrier Ratio: cationic lipid:plasmid DNA=5 nanomoles: 1 µg DNA.

DNA dose:

pZN27 alone: Individual mice received 500 µg, 1 mg, 2 mg, or 500 µg, followed 4 hours later by a second 500 µg dose, respectively of pZN27 in 200 µl 5% dextrose in water by tail vein injection.

pZN27 complexed to lipid carriers: 100 µg plasmid DNA complexed to 500 nanomoles to DDAB:Chol SUV lipid carriers in 200 µl 5% dextrose in water was injected by tail vein per mouse.

Mice: ICR, female, 25 grams.

Tissue extraction procedure: each organ was homogenized in 0.3 ml of 0.25M Tris-HCl pH 7.8, 5 mM EDTA, and the resulting extract was centrifuged and the supernatant was then subjected to 3 cycles of freeze-thaw and then heated to 65° C. for 20 min.

CAT assay procedure: the protein concentration of each tissue extract was quantitated using a Coomasie blue-based protein assay (Bio-Rad, Richmond, Calif.), and the same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham)), at 37° C. for 13 hrs.

Figure 12:
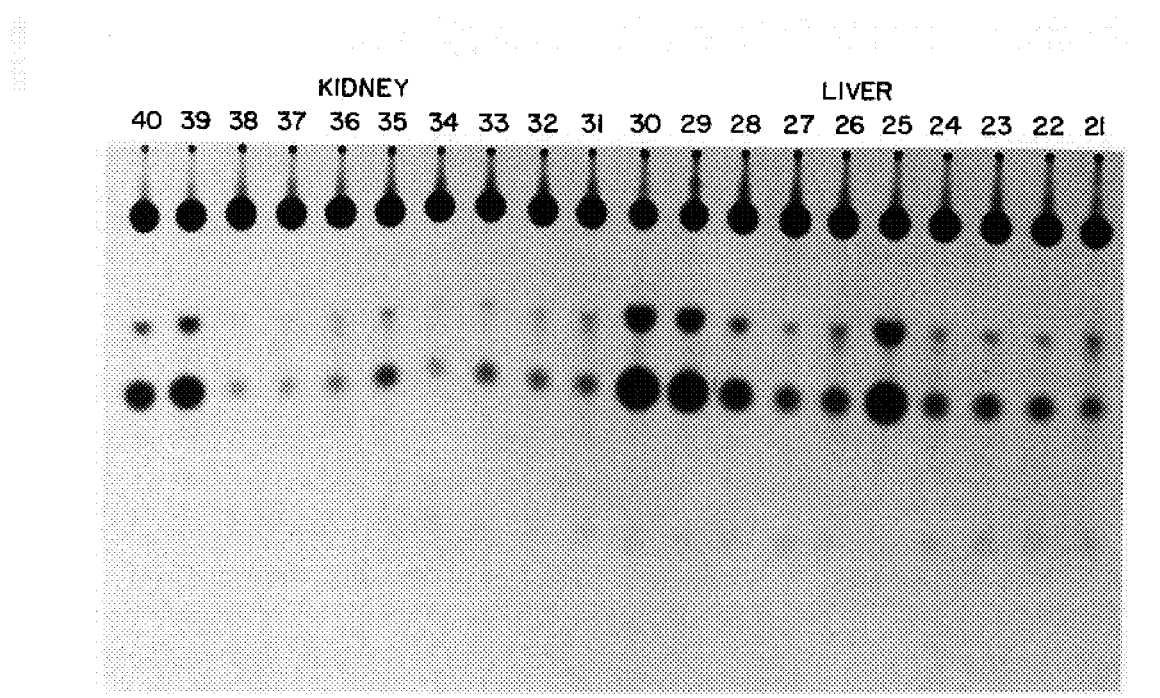
FIG. 12 is a photomicrograph showing CAT gene expression in the indicated tissues following intravenous injection with pZN27 (FIG. 11) alone or pZN27:DDAB:Chol SUV complexes. Lanes 1–10, lung; lanes 11–20, heart; lanes 21–30, liver, lanes 31–40, kidney complexes. Each tissue set of 10 contain samples treated with the following in order: 2 samples, 500 $\mu$g pZN27; 2 samples, 1 mg pZN27; 2 samples, 2 mg pZN27; 2 samples, 500 $\mu$g pZN27 twice; 2 samples, lipid carrier-pZN27 complex, 100 $\mu$g pZN27. Lipid carriers were 1 to 1 molar DDAB:Cholesterol Lipid carrier-pZN27 complex was 5 nanomoles cationic lipid to 1 $\mu$g DNA pZN27).
Figure 12:
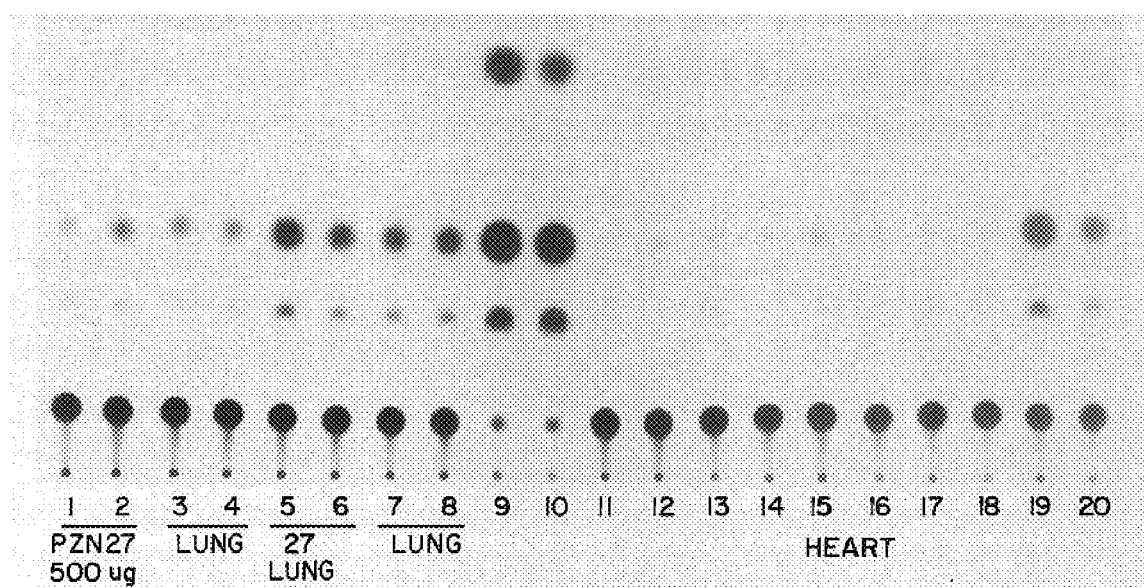

Results:

The results are shown in FIG. 12. Significant levels of CAT gene expression are seen in each of the 6 different tissues assayed after injection of either pZN27 alone, or pZN27 complexed to DDAB:cholesterol lipid carriers. Expression of a transgene in multiple tissues in vivo after systemic injection of a naked expression plasmid previously has not been demonstrated.

Example 14

Induction of High Levels of Human Interleukin-2 in the Spleen and Lymph Nodes of Mice by Intravenous Injection of Cationic Lipid Carriers Complexed to a CMV-Interleukin-2 Gene Mouse: C57/black 6, female, 25 grams.

Cancer: B16, mouse melanoma line which is highly metastatic to lung. The cell line was grown in RPMI-1640, 5% fetal calf serum.

Lipid carrier:DDAB:Cholesterol=1.1, 10 mM in 5% dextrose in water.

Plasmid: pZN46 (the HCMV promoter enhancer fused to the human interleukin-2 coding sequence).

Ratio: Cationic lipid:DNA=5 nmoles: 1 µg DNA in 200 µl of 5% dextrose in water administered per injection.

Inoculation of the Tumor Cell Line Into Mice and Administration of a Human Interleukin-2 Expression Plasmid-cationic Lipid Carrier Complexes:

B16 cells were trypsinized off the plates, and 50,000 cells were inoculated into each mouse by intravenous injection into the tail vein. Starting 2 days after the tumor cell injection, cationic lipid carrier-DNA complexes were injected via tail vein 2 times per week for a total of 2 weeks. The animals were sacrificed 2 weeks post tumor cell injection, the spleen and lymph nodes were removed, rendered into single cell suspensions using a tissue grinder, and then cultured for 24 hours in RPMI-1640, 10% fetal calf serum in 100 mm plastic dishes in a 37° C. incubator. After 24 hours the supernatant was collected and the concentration of human interleukin-2 in the supernatant was determined using a human IL-2 ELISA.

Results:

One hundred picograms of human interleukin-2 per ml was present in the spleen cell supernatant and 91 pg/ml IL-2 was present in the lymph node cell supernatant from the mouse which was injected with the pZN46-DDAB:chol lipid carrier complexes. No human interleukin-2 was detected in either spleen cell or lymph node cell supernatants derived from mice which received an identical injection of B-16 melanoma cells, but which did not receive the pZN46-DDAB:chol lipid carrier complexes. Thus, substituting the human interleukin-2 gene coding region for the CAT gene coding region in a HCMV expression plasmid resulted in high level expression of the IL-2 gene in vivo and the production of large amounts of a secreted human IL-2 protein in a mouse.

Example 15

Induction of High Level Expression of the Human CFTR Gene in Mice Treated by iv Administration of pZN32:Cationic Lipid Carrier Complexes Mice: ICR female, 25 grams.

Lipid carrier: DDAB:Chol=1.1 SUV, 10 mM in 5% dextrose in water.

Plasmid: pZN32 (the HCMV promoter enhancer fused to the human CFTR coding sequence).

Ratio: Cationic lipid:DNA=5 nmoles: 1 µg plasmid DNA.

Dose: A total of 100 µg of plasmid DNA in 200 µl of 5% dextrose in water administered per iv tail vein injection.

Procedure:

Forty-eight hours after injection mice were sacrificed, the lungs were removed and appropriately trimmed, embedded in OCT and snap frozen. Frozen tissues were sectioned at 6 microns, collected onto glass slides, and fixed for 10 minutes in 4% acetone. Immunolocalization of CFTR was then performed using the affinity purified rabbit polyclonal anti-CFTR antibody, α-1468. The procedure used was identical to the one described in Marino et al., *J. Clin. Invest.* 88:712 (1991) with the following variation. After washing, (1) a biotinylated antibody directed against the rabbit polyclonal antibody (Zymed) was added for 60 minutes, (2) followed by application of the streptavidin phosphatase complex (Zymed) for 60 minutes and (3) application of the substrate-chromogen. Slides were then coverslipped in water-soluble mounting media for examination.

Figure 10A:
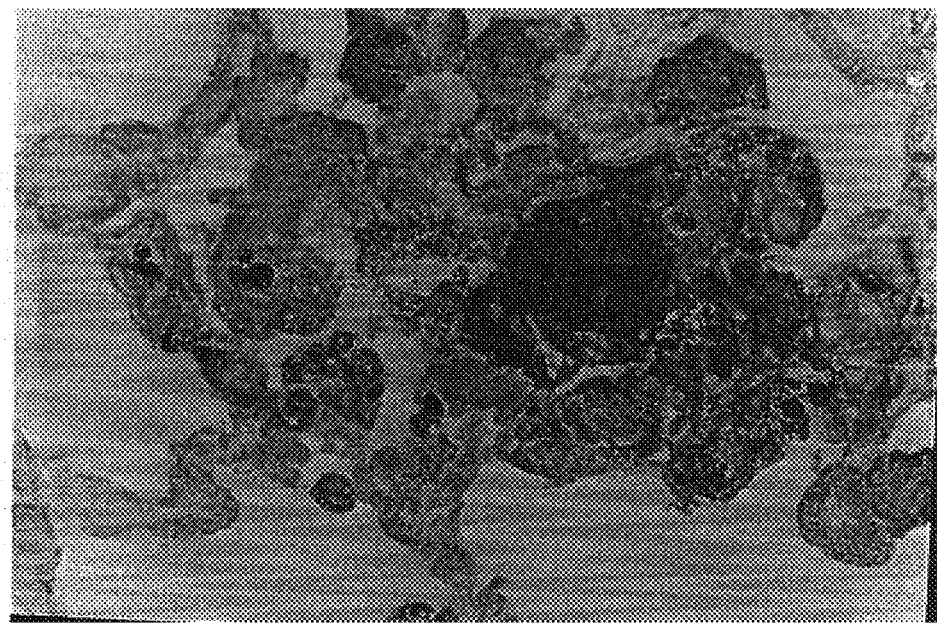
FIGS. 10A–10C show is a photomicrograph of a histochemical analysis of lungs from B-16 melanoma-bearing animals which received an intravenous injection of CMV-CAT cationic lipid carrier:DNA complexes. Lipid carriers were DOTAP:Cholesterol, 1 to 1 molar ratio. Cationic lipid:DNA ratio was 6 nanomoles: 1 $\mu$g DNA. The plasmid used was pZN20 (see FIG. 5). 100 $\mu$g DNA was injected per mouse. The immunohistochemical analysis revealed intense staining of many focal parenchymal tumors (FIG. 10A) and tumor emboli (FIG. 10B) within blood vessels (see FIG. 10B), indicating (see FIG. 10A) that large numbers of B16 melanoma tumor cells in the lung as well as blood-borne metastases are transfected after iv injection.
Figure 10B:
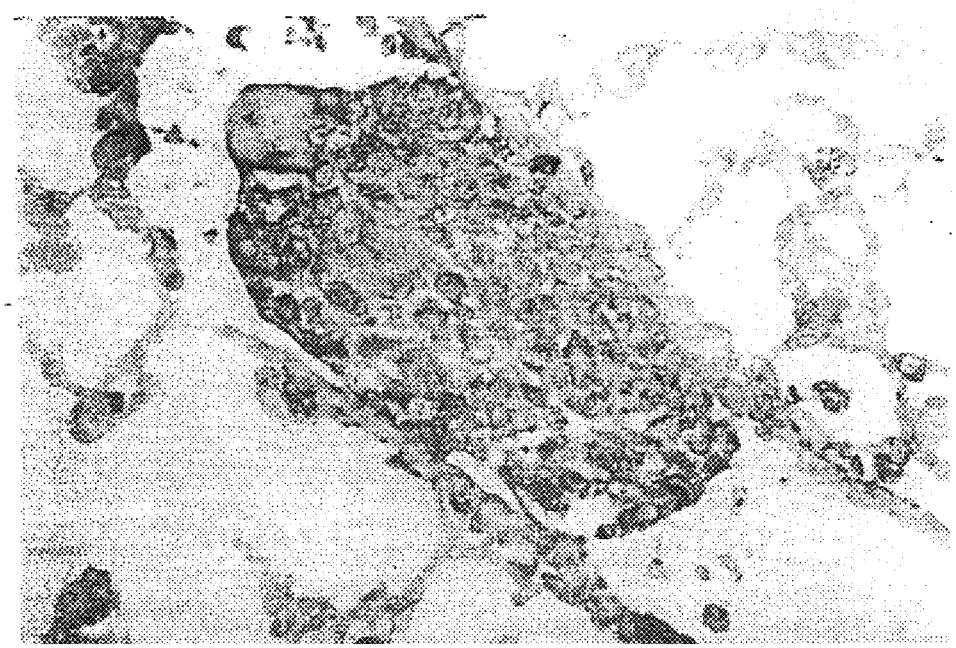
Figure 10C:
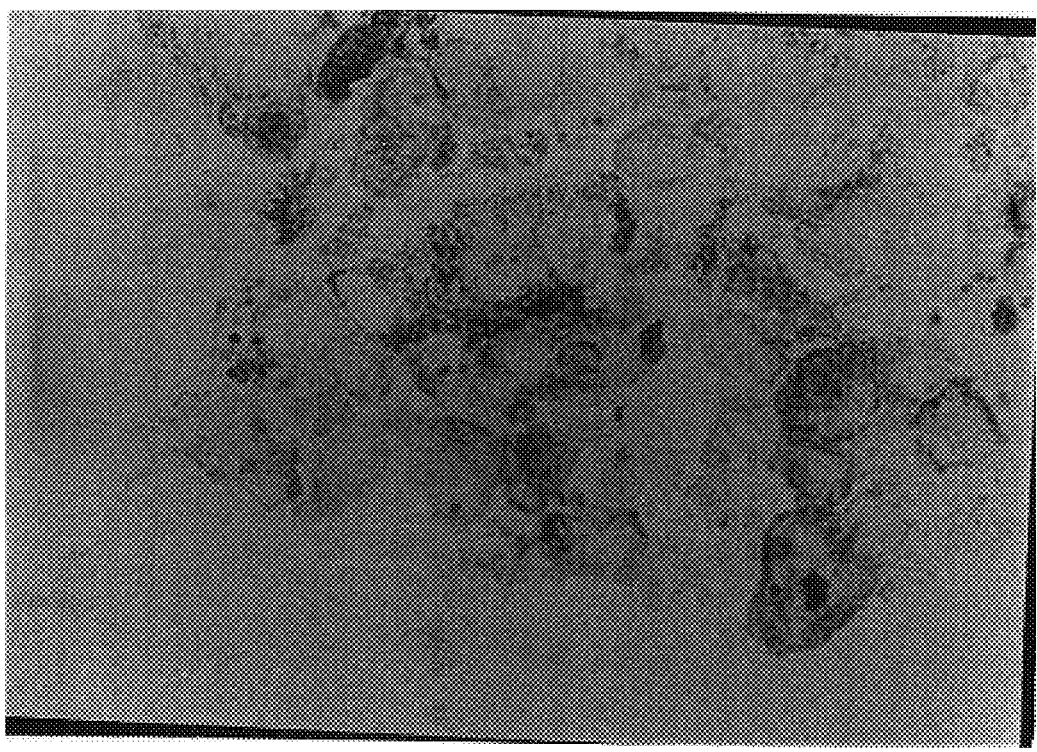

Results:

Photomicrographs of frozen sections (viewed at different magnifications) of mouse lung 48 hours following iv injection to pZN32-DDAB:cholesterol (1:1) liposome complexes and lung from untreated control are shown in FIGS. 10A–10E. As demonstrated by the intense staining with the polyclonal anti-CFTR antibody, α-1468, the overwhelming majority of the airways were transfected with the human CFTR gene. See FIGS. 10A, 10C and 10E, by visual inspection, essentially all the cells in transfected airways stain positively, demonstrating that the overwhelming majority of airway cells are transfected with the CFTR gene in vivo with a single aerosol dose of pZN32 complexed to DDAB-cholesterol (1:1) liposome-treated and control animals could not be distinguished histologically. Significant expression of the human CFTR gene is present in at least 50% of all the airways and at least 50% of all the airway lining cells (by visual inspection) in mouse lungs for at least 60 days following a single iv dose of pZN32 complexed to DDAB-cholesterol (1:1) liposomes. Frozen sections of mouse lungs from control animals (FIGS. 10B and 10D) do not show any detectable staining for CFTR, confirming that all the CFTR expression present in FIGS. 10A, 10C, and 10E is due to transfection of lung cells with the human CFTR gene.

As shown by the above results, a single iv dose of an expression liposome, containing a gene of interest, complexed to cationic liposomes transfects the majority of the cells lining the conducting airways of the lung, the gene product is present in the lung for at least 60 days, the expression appears to be airway cell-specific, and there is no histological evidence of damage following exposure. This is important because liposomes are well tolerated and non-immunogenic. Furthermore, the appearance, behavior, and life span of mice treated with intravenously injected pZN32:DDAB-chol. (1:1) complexed appear normal, and are indistinguishable from untreated, normal control animals. This lack of tonicity, as demonstrated by analysis of appearance, behavior, life span and detailed histologic analysis of a wide variety of tissues from these animals demonstrates the lack of toxicity produced by in vivo delivery of pZN32-DDAB:cholesterol complexes. Additionally, the effects of repeated iv administration of the DNA/liposome complexes is effective and is non-toxic. The cationic liposome-mediated DNA delivery by iv injection provides high level, lung-specific transgene expression in vivo.

Example 16

Demonstration of CAT Gene Expression in Lung and Liver After Intravenous Injection of Different CAT Gene-containing Plasmids Lipid carrier: DDAB:Chol=1:1, stock 5 mM in 5% dextrose in water.

Plasmids: Plasmids are indicated below.

DNA-Lipid carrier Ratio: Cationic lipid: plasmid DNA=1 nanomole: 1 µg

Dose: 100 µg DNA in 200 µl volume injected intravenously by tail vein injection.

Mice: ICR, female, 25 g

Procedure: The animals were sacrificed 24 hours after injection. The tissue extraction procedure and CAT assay were as described in Example 12 except that the CAT assay was incubated for 3 hr at 37° C. and 2.0 mM paraoxon (Lai, C.-C. et al. *Carcinogenesis* 9:1295–1302 (1988)) was added to the liver samples.

The results are shown in FIG. 19. Lanes 1–12 are lung samples, lanes 13–24 are liver samples. Lanes 1, 2, 13, 14 are pZN51; lanes 3, 4, 15, 16 are pZN60; lanes 5, 6, 17, 18 are pZN61; lanes 7, 8, 19, 20 are pZN62; lanes 9, 10, 21, 22 are pZN63; and lanes 11, 12, 23, 24 are pZN27.

Results:

pZN51, which does not contain an intron, is expressed as well as or better than plasmids containing an intron.

Example 17

Generalized Versus Tissue and Cell Type-specific CAT Gene Expression Produced by iv Injection of CMV-CAT-Liposome or CFTR-CAT-Liposome Complexes, Respectively Mouse: ICR female, 25 grams.

Liposome: DDAB:Cholesterol=1:1 SUV, 10 mM in 5% dextrose in water.

Plasmid: 1) pZN27 or 2) pBE3.8CAT (see Chou et al., *J. Biol Chem* 266:24471, 1991 for construction).

Experimental conditions: Mice in groups of 3 received 1) no treatment, or a single iv tail vein injection of DDAB-:CHOL liposomes complexed to 100 $\mu$g of 2) a 3.8 kb sequence of the 5' upstream region of the human CFTR gene fused to the CAT gene (pBE3.8CAT) or 3) pZN27. Mice were sacrificed 24 hours later and CAT activity assayed in lung, liver, spleen, lymph nodes, kidney and heart, as described in Example 12. Immunohistochemical analysis of lung section from each of the groups was performed as described in Example 11.

Figure 21A:
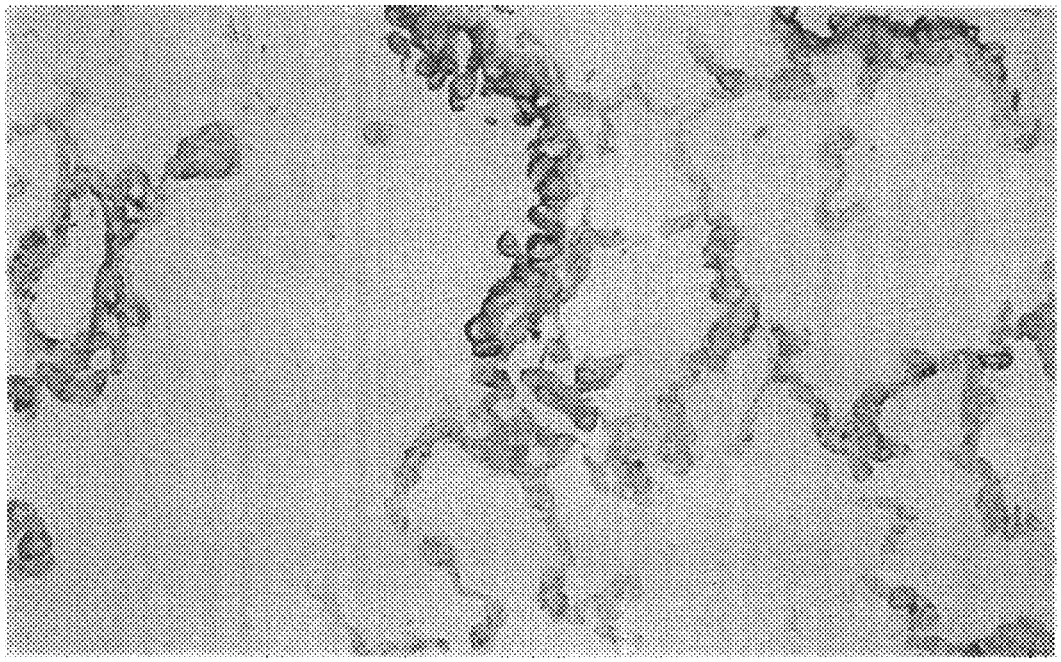
Figure 21B:
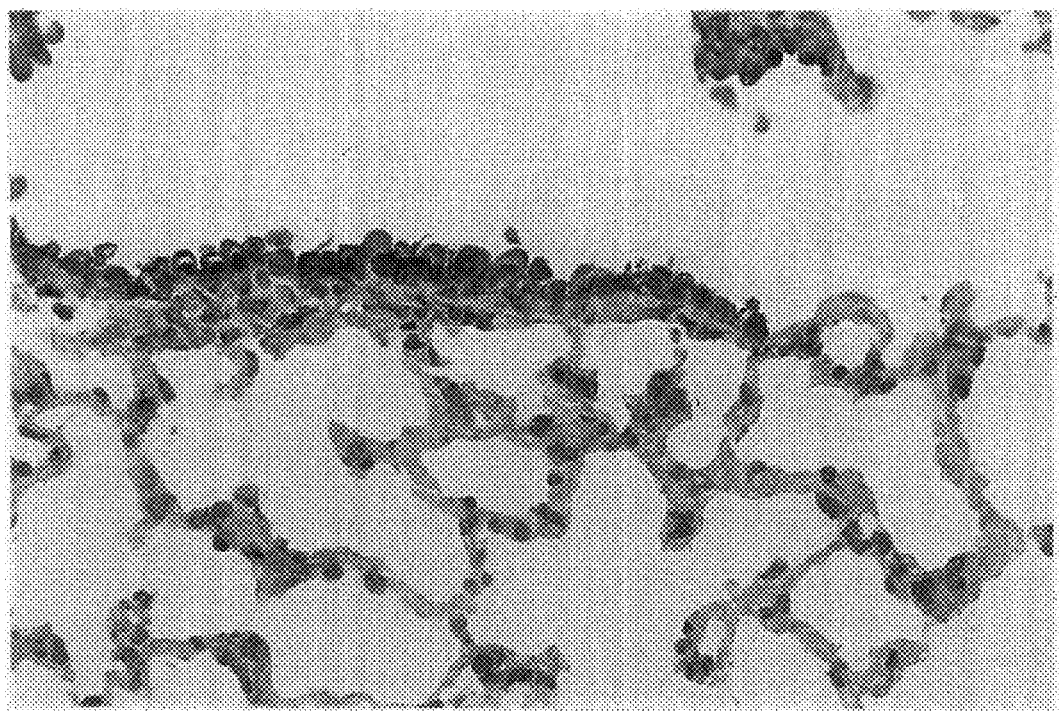
Figure 21C:
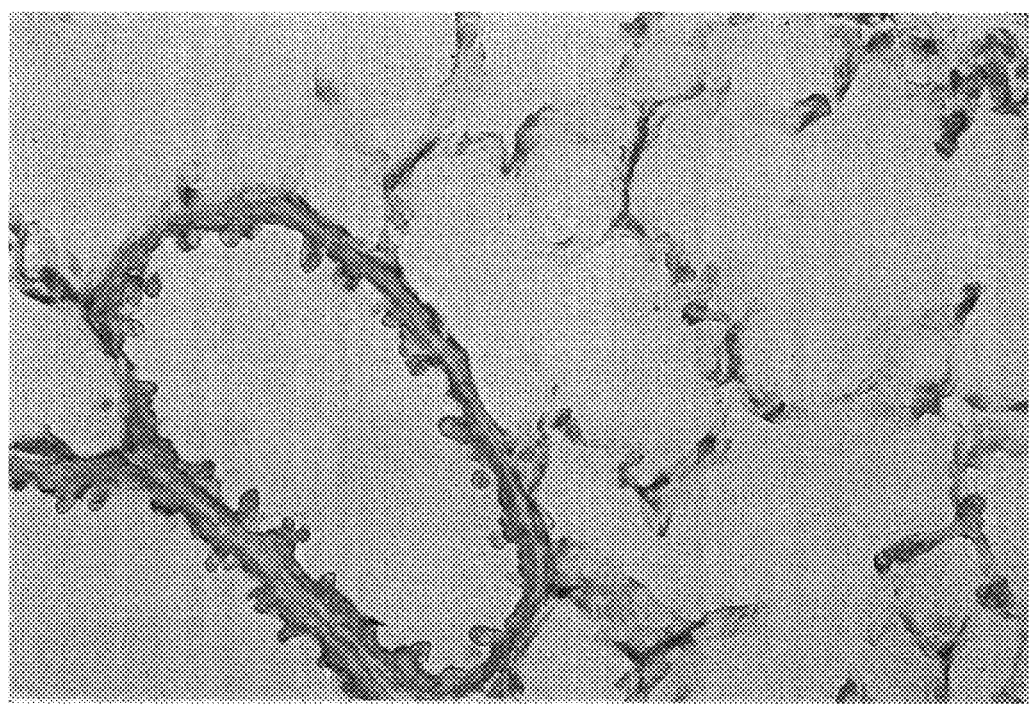
Figure 21D:
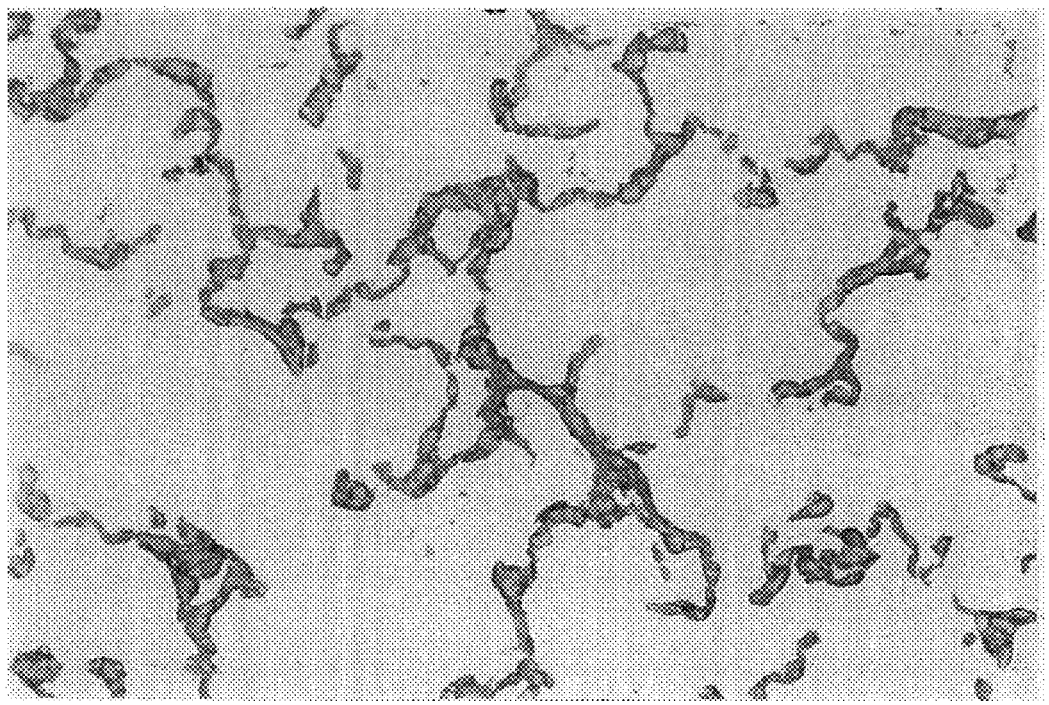
Figure 21E:
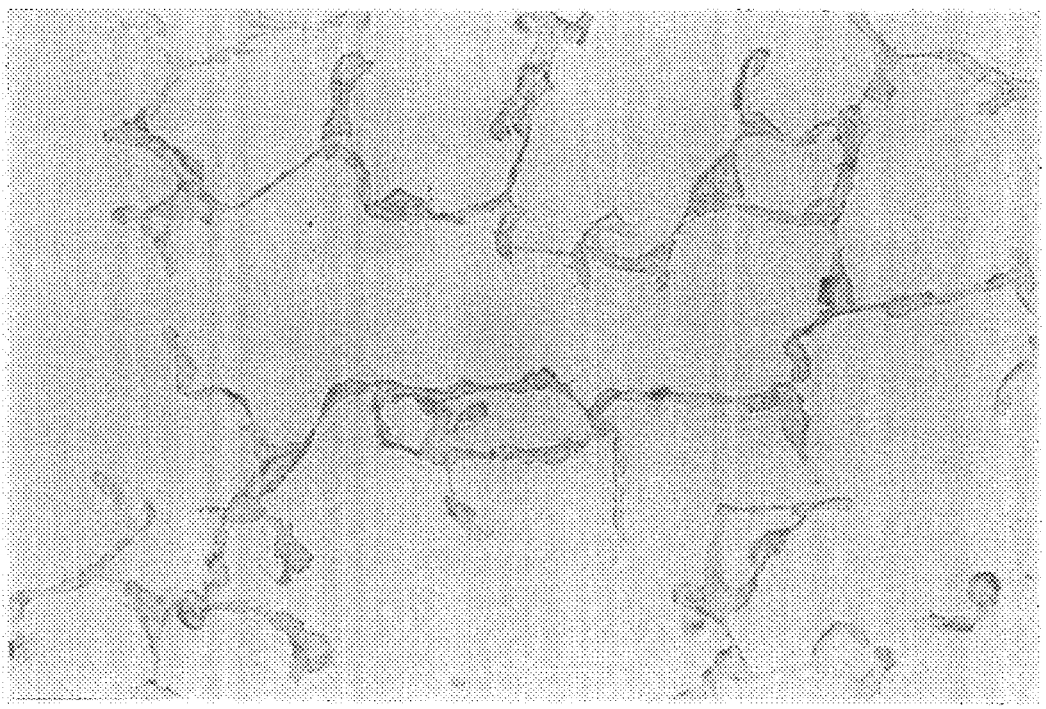
Figure 21G:
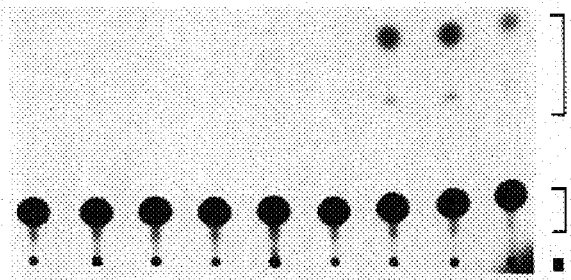
Figure 21I:
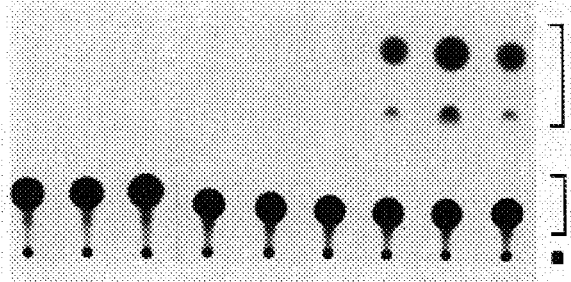
Figure 21K:
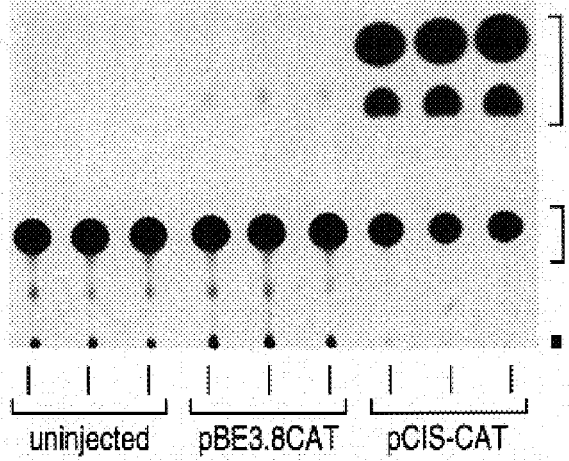
Figure 22:
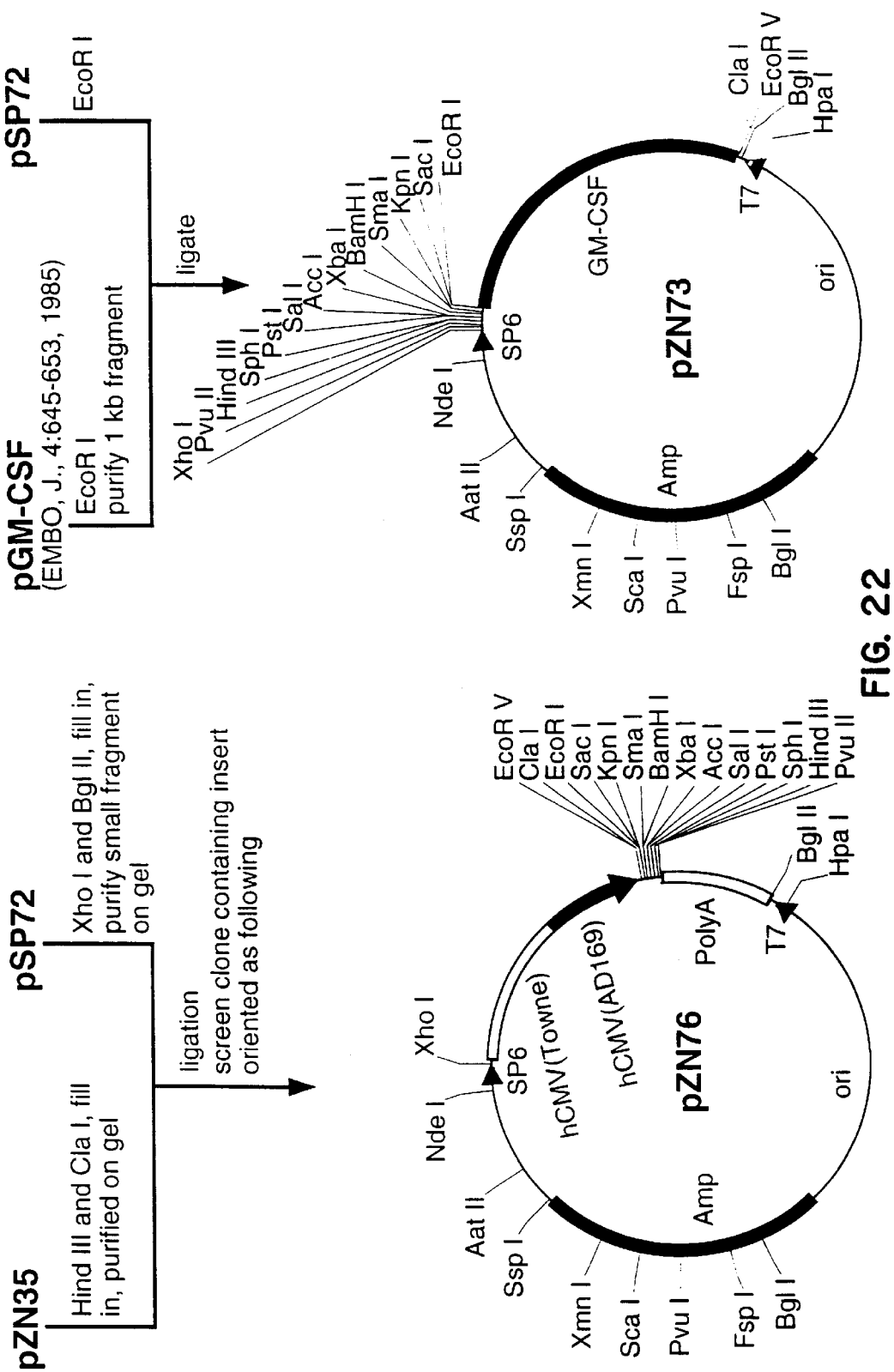
FIG. 22 shows the construction of plasmid pZN84.
Figure 22:
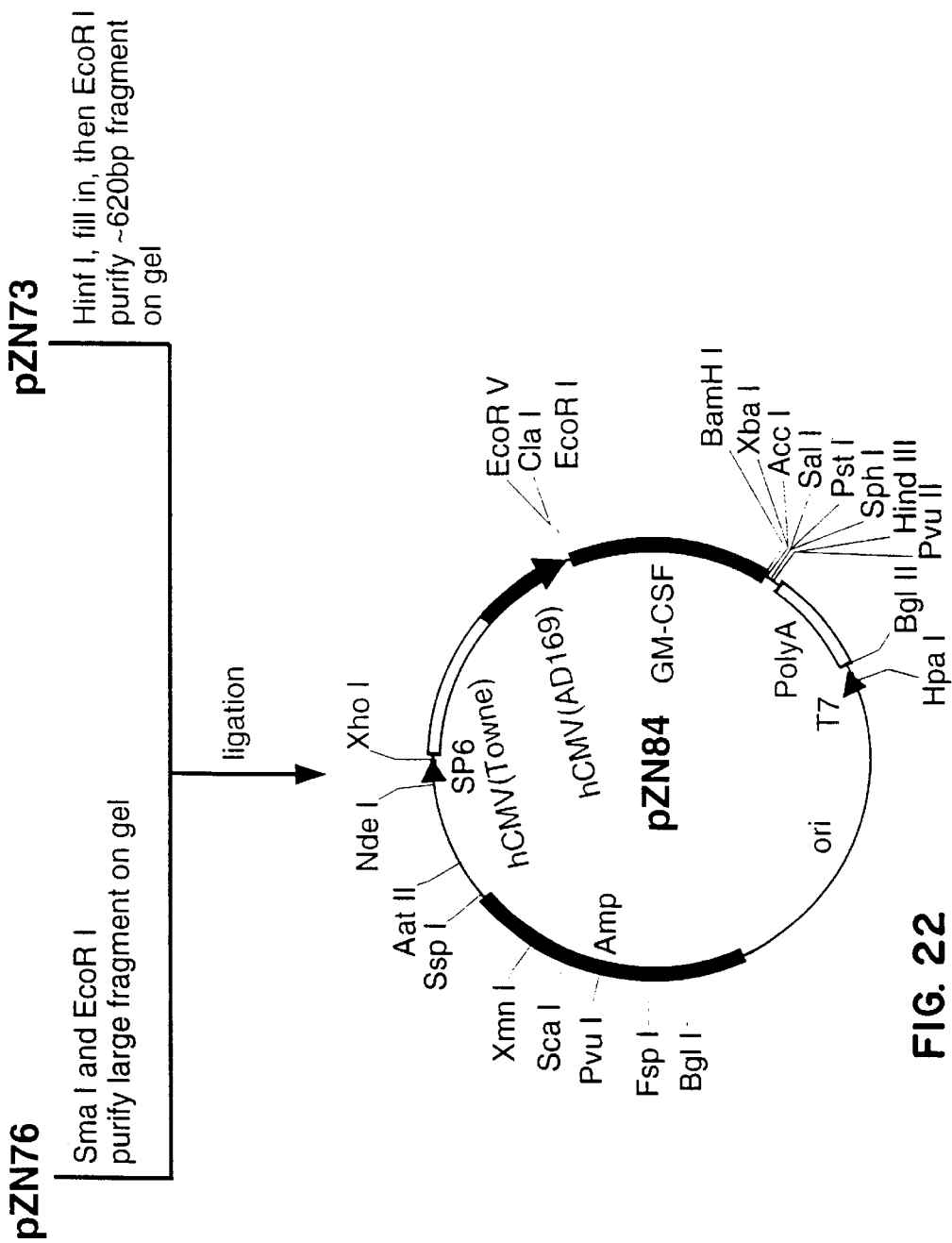
Figure 23:
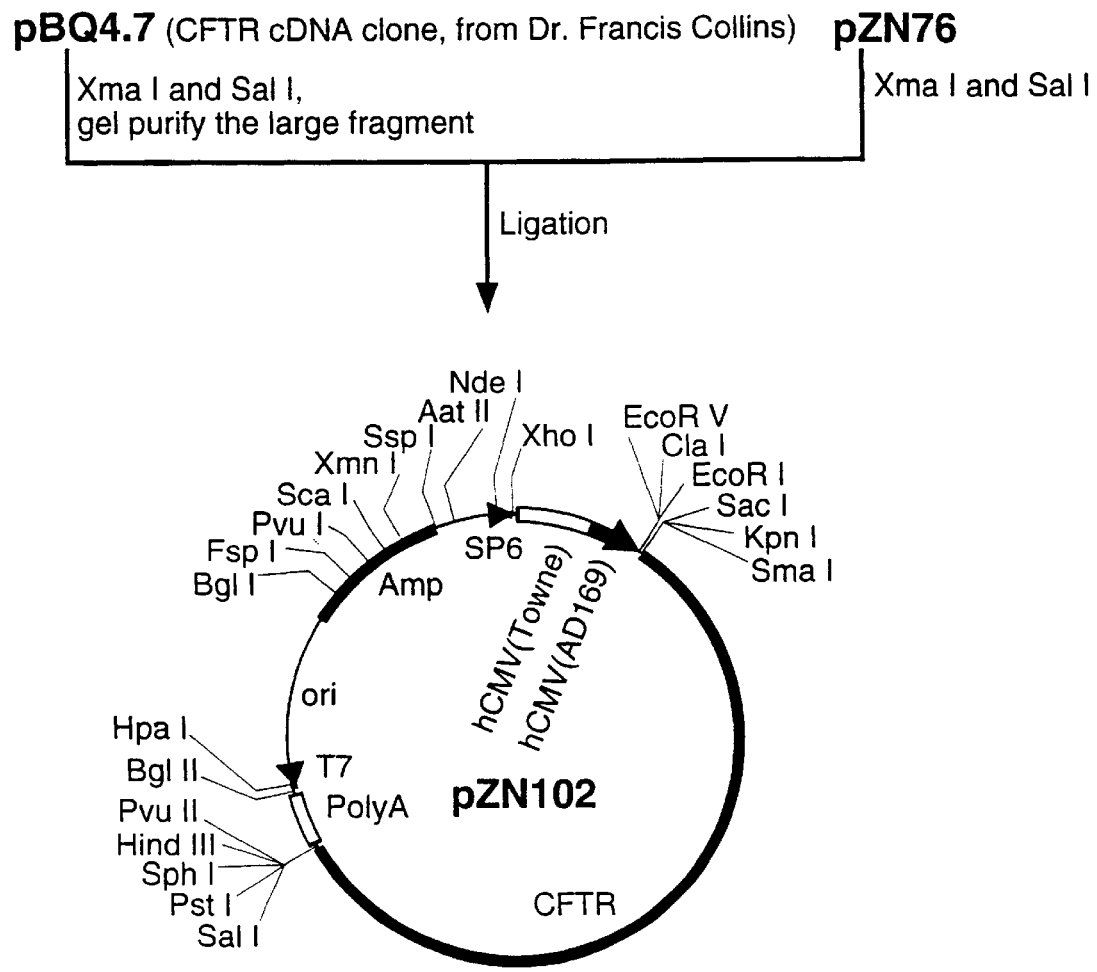
FIG. 23 shows the construction of pZN102.

Results:

Immunohistochemical staining of frozen lung sections from these mice showed that iv injection of CMV-CAT-liposome complexes produced high levels of red staining, indicating CAT gene expression in endothelial, alveolar and airway cells within the lung (21A). In contrast, CFTR-CAT-liposome complexes produced CAT gene expression primarily localized in airway epithelial cells (21B). This approximates the pattern of endogenous CFTR gene expression in rat lung, as determined by in situ hybridization studies (Trezise and Buchwald, *Nature*, 353:434, 1991). A lung section from an uninjected mouse does not show red staining, indicating that CAT gene expression is present only in transfected cells (FIG. 21C). FIG. 21D is a high magnification photomicrograph of alveoli from a CMV-CAT treated mouse and shows a high level of CAT gene expression in both alveolar cells and lung endothelial cells. A high magnification photomicrograph of alveoli from CFTR-CAT treated mice (FIG. 21E) shows no significant CAT gene expression in either alveolar or endothelial cells, demonstrating that the CFTR promoter targets transgene expression to airway epithelial cells. This is the first demonstration that transgenes can be expressed within mouse lung in either a generalized or cell type-specific fashion depending on the regulatory element used, after iv injection.

CAT assay demonstrated that CMV-CAT produced significant CAT gene expression in the lung, liver, heart, spleen, lymph nodes and kidney, whereas CFTR-CAT produced lung-specific gene expression. Photographs of autoradiographic analysis of each tissue are shown in FIGS. 21(G–L). Thus, the CMV promoter induces expression of a linked gene in a wide range of tissues, whereas the 5' flanking region of the human CFTR gene directs tissue-specific transgene expression after iv, liposome-based administration.

Example 18

Comparison of Transfection Focusing on iv Injection of Plasmid Alone With iv Injection of Plasmid Complexed to a Lipid Carrier Demonstration of Widespread, High Level CAT Gene Expression in In Vivo After Intravenous (iv) Injection of pZN51 Alone.

Plasmid: pZN51.

DNA:Liposome Ratio: Plasmid DNA alone, without liposomes, was injected.

DNA dose: 1 mg plasmid DNA in 200 $\mu$l 5% dextrose in water was injected times 2 over a 4 hour period by tail vein per mouse. Mice were sacrificed 24 hours later and 17 different tissues were assayed for CAT gene activity.

Mice: ICR, female, 25 grams.

Tissue extraction procedure: each organ was homogenized in 0.3 ml of 0.25 M Tris-HCl pH 7.8, 5 mM EDTA, and the resulting extract was centrifuged and then subjected to 3 cycles of freeze-thaw and then treated to 65° C. for 20 min.

CAT assay procedure: the protein concentration of each tissue extract was quantitated using a ninhydrin-based protein assay (Bio-Rad, Berkeley, Calif.), and the same amount of total protein from each tissue extract was added in the CAT assay, together with 10 $\mu$l of 20 mM acetyl CoA+12 $\mu$l of $^{14}$C-chloramphenicol (25 $\mu$Ci/ml, 55 mCi/mmole, Amersham)), at 37° C. for 13 hrs.

Figure 24A:
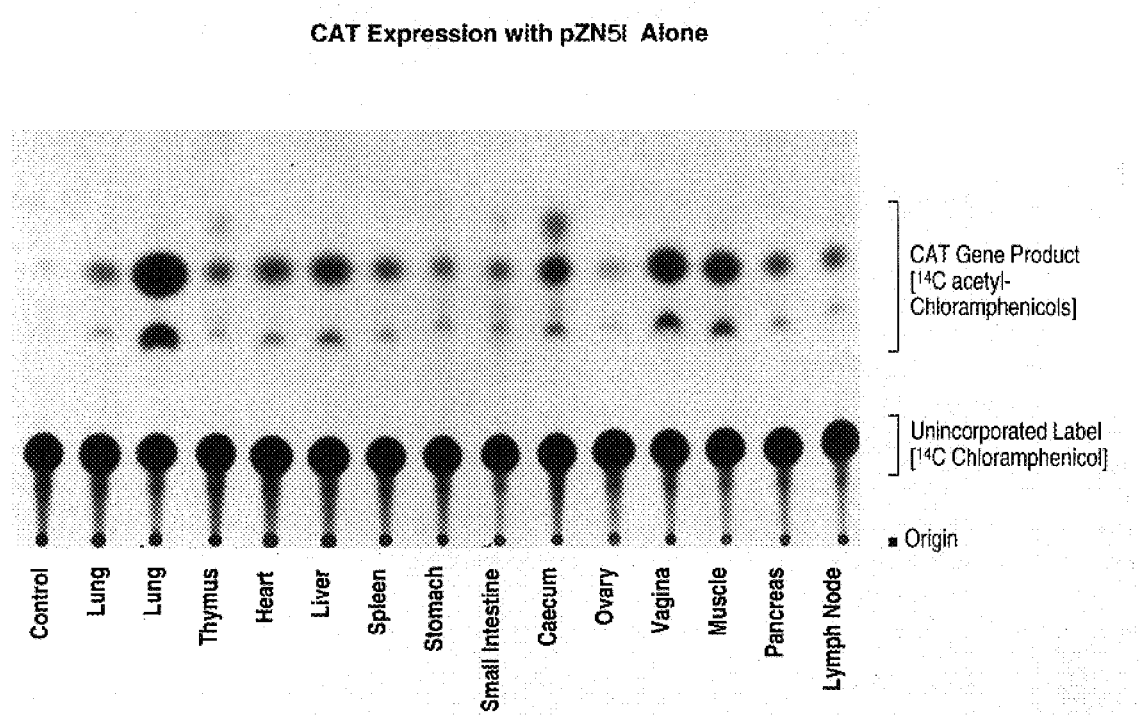
FIGS. 24A and 24B show an autoradiograph of a TLC plate showing CAT activity following PZN51 alone.
Figure 24B:
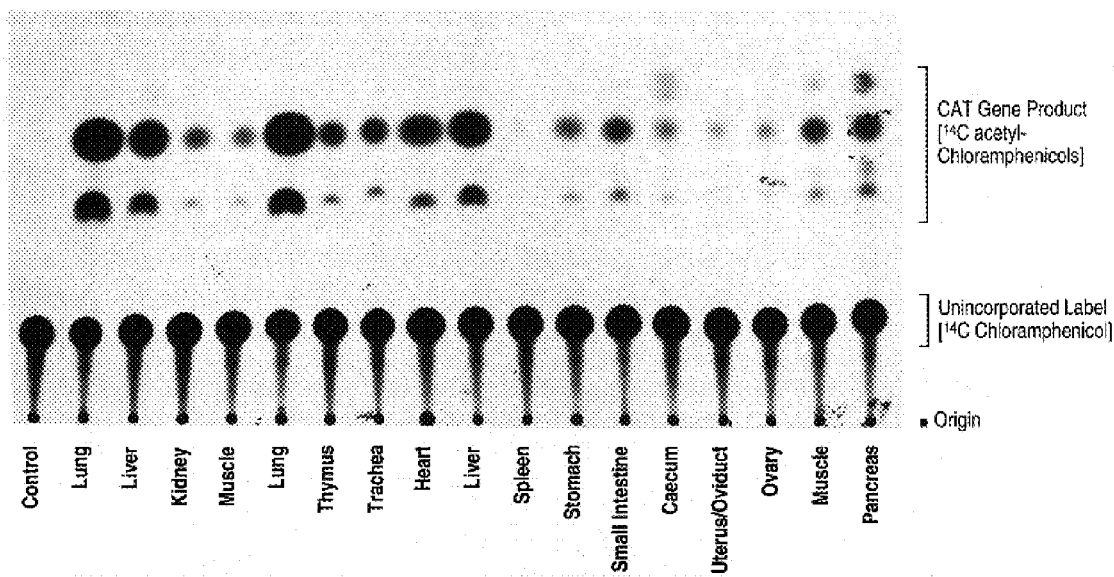

Results: Compared to control levels (lane 1), iv injection of pZN51 alone produced highly significant levels of CAT gene expression in the following tissues: lung, thymus, esophagus, heart, liver, spleen, stomach, small intestine, caecum, ovary, vagina, skeletal muscle, pancreas and lymph nodes (LN). Thus, iv injection of the pZN51 expression plasmid alone can efficiently transfect a very large and diverse number of tissues in the body. An autoradiograph of these results is presented in FIG. 24.

Demonstration of Widespread, High Level CAT Gene Expression In Vivo After Intravenous (iv) Injection of pZN51 Complexed to DDAB:cholesterol (1:1) Liposomes Plasmid: pZN51.

Liposome: DDAB:Chol=1:1, stock 10 mM in 5% dextrose.

DNA:Liposome Ratio: liposome:plasmid=1:5.

DNA dose: 100 $\mu$g plasmid DNA in 200 $\mu$l 5% dextrose in water was injected by tail vein per mouse. Mice were sacrificed 24 hours later and 17 different tissues were assayed for CAT gene activity.

Mice: ICR, female, 25 grams.

Tissue extraction procedure: each organ was homogenized in 0.3 ml of 0.25 M Tris-HCl pH 7.8, 5 mM EDTA, and the resulting extract was centrifuged and then subjected to 3 cycles of freeze-thaw and then treated to 65° C. for 20 min.

CAT assay procedure: the protein concentration of each tissue extract was quantitated using a ninhydrin-based protein assay (Bio-Rad, Berkeley, Calif.), and the same amount of total protein from each tissue extract was added in the CAT assay, together with 10 $\mu$l of 20 mM acetyl CoA+12 $\mu$l of $^{14}$C-chloramphenicol (25 µCi/ml, 55 mCi/mmole, amersham)), at 37° C. for 13 hrs.

Results: Compared to control levels (lane 1), iv injection of pZN51:DDAB:chol complexes produced high levels of CAT gene expression in the following tissues: lung, thymus, esophagus, heart, liver, spleen, stomach, small intestine, large intestine, caecum, uterus, ovary, vagina, skeletal muscle, pancreas and lymph nodes (LN). Thus, iv injection of pZN51:DDAB:Chol complexes can efficiently transfect a very large and diverse number of tissues in the body (see FIG. 24B).

Example 19

Injection of GM-CSF Expression Plasmid-cationic Liposome Complexes Produces Significant Antitumor Effects Mouse: C57/black 6, female, 25 grams.

Cancer: B 16, mouse melanoma line which is highly metastatic to lung. The cell line was grown in RPMI-1640, 5% fetal calf serum.

Liposome: DDAB:Cholesterol=1:1, 10 mM in 5% dextrose in water. Twenty five thousand B-16 cells were injected iv by tail vein.

Plasmid: pZN84 (the HCMV promoter enhancer fused to the murine GM-CSF coding sequence).

Ratio: Cationic lipid:DNA=5 nmoles:1 µg. A total of 100 µg of plasmid DNA in 200 µl of 5% dextrose in water administered per injection.

Experimental outline: C57B mice in groups of eight received a single iv tail vein injection of $2.5 \times 10^4$ B-16 melanoma cells. Group 1 received no treatment, group 2 received bi-weekly injections of 100 µg of a CMV-GM-CSF expression plasmid complexed to DDAB:CHOL liposomes, beginning 4 days prior to tumor cell injection and continuing for 2 weeks following tumor injection. All mice were sacrificed 3 weeks following tumor cell injection and surface lung tumor nodules which are black and macroscopic were counted using a dissecting microscope.

Results:

Control animals had 64.5±19.7 (S.E.M.) nodules per lung. In contrast, the GM-CSF-liposome-treated animals had 11.9±3.6 tumor nodules per lung (p<0.01 versus the control group, as assessed by Students test). Thus, iv injection of a cytokine gene produced a highly significant antitumor effect. This is the first demonstration that iv injection of a gene can produce anti-tumor activity in vivo.

Example 20

High Level Expression of the CAT Gene in Mouse Brain Produced by Injection of DNA Alone or DNA-cationic Liposome Complexes Directly Into the Central Nervous System Mice: ICR, female, 25 grams Plasmid: pCIS-CAT Liposome: DOTMA:DOPE (1:1)

For each mouse injected, 2.5 mg DNA was diluted in 5% dextrose, then mixed with liposomes diluted to the same volume in 5% dextrose. Five microliters were injected stereotactically into the right ventricle of each mouse.

Ratio:
p:L=1.0=1 mg DNA:0 µmoles DOTMA
P:L=1.1=1 mg DNA:1 µmoles DOTMA
P:L=1.3=1 mg DNA:3 µmoles DOTMA
p:L=1.4=1 mg DNA:4 µmoles DOTMA
p:L=1:6=1 mg DNA:6 µmoles DOTMA Mice were sacrificed 48 hr. post injection. Brains were removed and separated into left and right hemispheres. Each hemisphere was homogenized in 250 µl 0.25 M Tris pH 7.8. 5 mM EDTA followed by three cycles of freeze-thaw and 10 min. at 65° C.

Figure 6A:
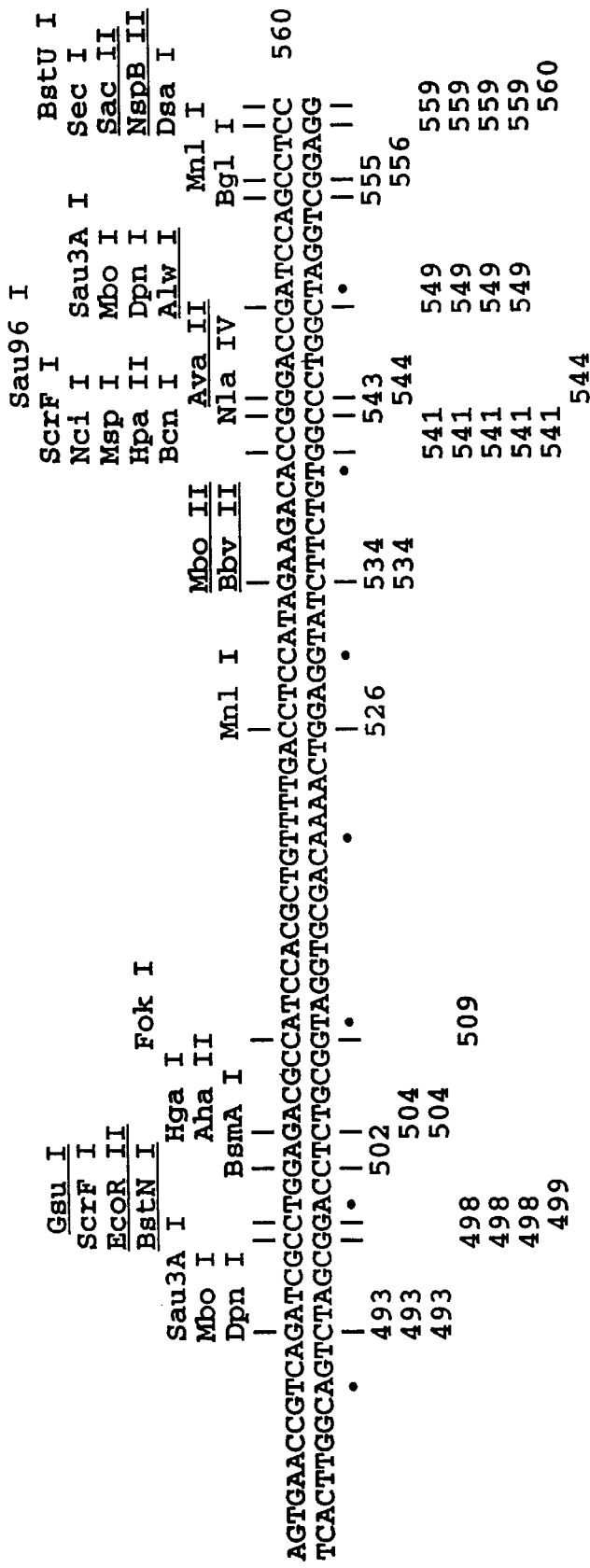

The amounts of extracts used for CAT assay were normalized to protein levels. 0.3 ml of $^{14}$C-Chloramphenicol was used for each assay. Assay was carried out at 37° C. overnight. The reaction products were separated on TLC plate and exposed to film, as described in FIG. 6.

Figure 25:
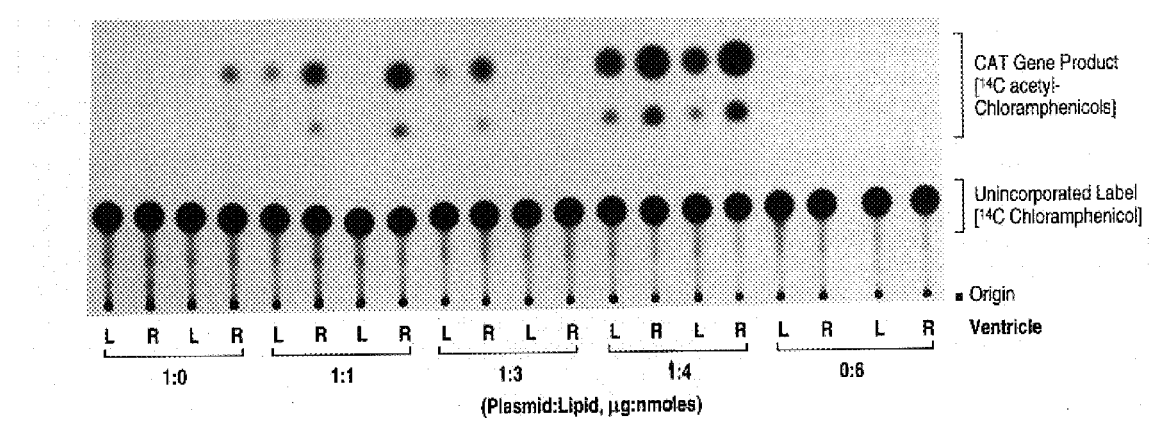
FIG. 25 shows an autoradiograph of a TLC plate of injection into the right (r) ventricle of pCIS-CAT complexed to DOTMA:DOPE (1:1) lipid carriers in the indicated ratios of plasmid:lipid. The left (L) ventricle was not injected and therefore transfection of the left ventricles demonstrates that the entire brain is being transfected.

Results: These results demonstrate that high level expression of a heterologous gene can be produced throughout the brain by injection of DNA-liposome complexes (at appropriate ratios) directly into the central nervous system. They also demonstrate that injection of an expression plasmid alone can produce significant transgene expression in the brain. The results are shown in FIG. 25.

As shown by the above results, a plurality of tissues can be transformed following systemic administration of transgenes, either complexed to a lipid carrier or as naked nucleic acid. Expression of exogenous DNA following intravenous injection of a cationic lipid carrier/exogenous DNA complex into a mammalian host has been shown in multiple tissues, including T lymphocytes metastatic tumors and intravascular tumor emboli. Expression of exogenous DNA in multiple different tissues, including those of the reticuloendothelial cell system has been obtained following intravenous injection of an expression plasmid as naked DNA. The ability to transfect T lymphocytes in vivo will have a dramatic impact on the treatment of AIDS, cancer, multiple sclerosis, and arthritis. In vivo transfection of cardiac endothelial cells will have a dramatic impact on the treatment of heart disease and heart attacks. In vivo transfection of lung cells will have a dramatic impact on the treatment of cystic fibrosis, asthma, emphysema and lung cancer. In vivo transfection of bone marrow cells will have a dramatic impact on the treatment of cancer, blood diseases and infections.

The in vivo gene therapy delivery technology as described above is non-toxic in animals and transgene expression has been shown to last for at least 60 days after a single administration. The transgene does not appear to integrate into host cell DNA at detectable levels in vivo as measured by Southern analysis, suggesting that this technique for gene therapy will not cause problems for the host mammal by altering the expression of normal cellular genes activating cancer-causing oncogenes, or turning off cancer-preventing tumor suppressor genes. Additionally, transgene expression after systemic administration of a DNA expression vector alone has been shown; transgene expression was produced in the lung for at least three weeks after a single administration of a DNA expression vector without a carrier system.

Systemic injection of heterologous genes into adult animals can produce very high level transgene expression in a wide range of tissues, and transfect the majority (>70%) of all cells present in many of these tissues as demonstrated above. In contrast, previous studies attempting direct transfer of heterologous genes into adult animals have reported transfection limited to one or a few tissues, low levels of transgene expression in these tissues and (whenever histochemical analysis was included) transfection limited to less than 1% of the cells present in transfected tissues.

In addition to transfecting the majority of all cells present in the lung, using the methods and constructs described above, high level transgene expression has been obtained in a wide variety of other tissues and cell types which have never before been transfected in vivo by any gene transfer approach. These include:

Transfection of the majority of all cells present in the spleen and lymph nodes, including transfection of greater than 70% of all the T lymphocytes.

The ability to efficiently transfect T lymphocytes in vivo permitting for the first time specific molecular approaches to both anti-HIV therapy and to selective modulation of the immune response.

Efficient transfection of visceral tumors and of intravascular tumor emboli after iv injection of DNA into tumor-bearing hosts. Previously, gene transfer studies involving cancer have been restricted solely to ex vivo approaches. Our work now permits direct transfection with transgenes which provide tumor suppressor, anti-oncogene and/or anti-metastases activity within tumors in tumor-bearing hosts.

Transfection of the majority of cardiac vascular endothelial cells, as well as bone marrow-derived hematopoietic cells, including the great majority of blast cells present in the bone marrow, by systemic delivery of heterologous genes. These results create dramatic and new means for controlling ischemic heart disease and hematopoiesis at the molecular level.

Demonstration of the ability to produce high level in vivo expression of a variety of biologically important transgenes, as exemplified by human CFTR, IL-2 and GM-CSF.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

SEQUENCE LISTING (1) GENERAL INFORMATION:

(iii) NUMBER OF SEQUENCES:        4

(2) INFORMATION FOR SEQ ID NO:    1:

(i) SEQUENCE CHARACTERISTICS:
            (A) LENGTH:               616
            (B) TYPE:                 nucleic acid
            (C) STRANDEDNESS:         single
            (D) TOPOLOGY:             linear (xi) SEQUENCE DESCRIPTION: SEQ ID NO: 1:

GGCGACCGCC CAGCGACCCC CGCCCGTTGA CGTCAATAGT GACGTATGTT CCCATAGTAA        60

CGCCAATAGG GACTTTCCAT TGACGTCAAT GGGTGGAGTA TTTACGGTAA ACTGCCTACT       120

TGGCAGTACA TCAAGTGTAT CATATGCCAA GTCCGCCCCC TATTGACGTC AATGACGGTA       180

AATGGCCCGC CTAGCATTAT GCCCAGTACA TGACCTTACG GGAGTTTCCT ACTTGGCAGT       240

ACATCTACGT ATTAGTCATC GCTATTACCA TGGTGATGCG GTTTTGGCAG TACACCAATG       300

GGCGTGGATA GCGGTTTGAC TCACGGGGAT TTCCAAGTCT CCACCCCATT GACGTCAATG       360

GGAGTTTGTT TTGGCACCAA AATCAACGGG ACTTTCCAAA ATGTCGTAAT AACCCCGCCC       420

CGTTGACGCA AATGGGCGGT AGGCGTGTAC GGTGGGAGGT CTATATAGCA GAGCTCGTTT       480

AGTGAACCGT CAGATCGCCT GGAGACGCCA TCCACGCTGT TTTGACCTCC ATAGAAGACA       540

CCGGGACCGA TCCAGCCTCC GCGGCCGGGA ACGGTGCATT GGAACGCGGA TTCCCCGTGC       600

CAAGAGTGAC GTAAGT                                                      616

(2) INFORMATION FOR SEQ ID NO:    2:

(i) SEQUENCE CHARACTERISTICS:
            (A) LENGTH:               930
            (B) TYPE:                 nucleic acid
            (C) STRANDEDNESS:         single
            (D) TOPOLOGY:             linear (xi) SEQUENCE DESCRIPTION: SEQ ID NO: 2:

AATCAATATT GGCCATTAGC CATATTATTC ATTGGTTATA TAGCATAAAT CAATATTGGC        60

TATTGGCCAT TGCATACGTT GTATCCATAT CATAATATGT ACATTTATAT TGGCTCATGT       120

| CCAACATTAC CGCCATGTTG ACATTGATTA TTGACTAGTT ATTAATAGTA ATCAATTACG | 180 |
| GGGTCATTAG TTCATAGCCC ATATATGGAG TTCCGCGTTA CATAACTTAC GGTAAATGGC | 240 |
| CCGCCTGGCT GACCGCCCAA CGACCCCCGC CCATTGACGT CAATAATGAC GTATGTTCCC | 300 |
| ATAGTAACGC CAATAGGGAC TTTCCATTGA CGTCAATGGG TGGAGTATTT ACGGTAAACT | 360 |
| GCCCACTTGG CAGTACATCA AGTGTATCAT ATGCCAAGTA CGCCCCCTAT TGACGTCAAT | 420 |
| GACGGTAAAT GGCCCGCCTG GCATTATGCC CAGTACATGA CCTTATGGGA CTTTCCTACT | 480 |
| TGGCAGTACA TCTACGTATT AGTCATCGCT ATTACCATGG TGATGCGGTT TTGGCAGTAC | 540 |
| ATCAATGGGC GTGGATAGCG GTTTGACTCA CGGGGATTTC CAAGTCTCCA CCCCATTGAC | 600 |
| GTCAATGGGA GTTTGTTTTG GCACCAAAAT CAACGGGACT TTCCAAAATG TCGTAACAAC | 660 |
| TCCGCCCCAT TGACGCAAAT GGGCGGTAGG CGTGTACGGT GGGAGGTCTA TATAAGCAGA | 720 |
| GCTCGTTTAG TGAACCGTCA GATCGCCTGG AGACGCCATC CACGCTGTTT TGACCTCCAT | 780 |
| AGAAGACACC GGGACCGATC CAGCCTCCGC GGCCGGGAAC GGTGCATTGG AACGCGGATT | 840 |
| CCCCGTGCCA AGAGTGACGT AAGTACCGCC TATAGAGTCT ATAGGCCCAC CCCCTTGGCT | 900 |
| TCTTATGCAT GCTATACTGT TTTTGGCTTG | 930 |

(2) INFORMATION FOR SEQ ID NO: 3:

(i) SEQUENCE CHARACTERISTICS:
        (A) LENGTH:       616
        (B) TYPE:         nucleic acid
        (C) STRANDEDNESS:  single
        (D) TOPOLOGY:     linear (xi) SEQUENCE DESCRIPTION: SEQ ID NO: 3:

| GGCGACCGCC CAGCGACCCC CGCCCGTTGA CGTCAATAGT GACGTATGTT CCCATAGTAA | 60 |
| CGCCAATAGG GACTTTCCAT TGACGTCAAT GGGTGGAGTA TTTACGGTAA ACTGCCCACT | 120 |
| TGGCAGTACA TCAAGTGTAT CATATGCCAA GTCCGCCCCC TATTGACGTC AATGACGGTA | 180 |
| AATGGCCCGC CTAGCATTAT GCCCAGTACA TGACCTTACG GGAGTTTCCT ACTTGGCAGT | 240 |
| ACATCTACGT ATTAGTCATC GCTATTACCA TGGTGATGCG GTTTTGGCAG TACACCAATG | 300 |
| GGCGTGGATA GCGGTTTGAC TCACGGGGAT TTCCAAGTCT CCACCCCATT GACGTCAATG | 360 |
| GGAGTTTGTT TTGGCACCAA AATCAACGGG ACTTTCCAAA ATGTCGTAAT AACCCCGCCC | 420 |
| CGTTGACGCA AATGGGCGGT AGGCGTGTAC GGTGGGAGGT CTATATAGCA GAGCTCGTTT | 480 |
| AGTGAACCGT CAGATCGCCT GGAGACGCCA TCCACGCTGT TTTGACCTCC ATAGAAGACA | 540 |
| CCGGGACCGA TCCAGCCTCC GCGGCCGGGA ACGGTGCATT GGAACGCGGA TTCCCCGTGC | 600 |
| CAAGAGTGAC GTAAGT | 616 |

(2) INFORMATION FOR SEQ ID NO: 4:

(i) SEQUENCE CHARACTERISTICS:
        (A) LENGTH:       930
        (B) TYPE:         nucleic acid
        (C) STRANDEDNESS:  single
        (D) TOPOLOGY:     linear (xi) SEQUENCE DESCRIPTION: SEQ ID NO: 4:

| AATCAATATT GGCCATTAGC CATATTATTC ATTGGTTATA TAGCATAAAT CAATATTGGC | 60 |
| TATTGGCCAT TGCATACGTT GTATCCATAT CATAATATGT ACATTTATAT TGGCTCATGT | 120 |
| CCAACATTAC CGCCATGTTG ACATTGATTA TTGACTAGTT ATTAATAGTA ATCAATTACG | 180 |
| GGGTCATTAG TTCATAGCCC ATATATGGAG TTCCGCGTTA CATAACTTAC GGTAAATGGC | 240 |

-continued

```
CCGCCTGGCT GACCGCCCAA CGACCCCCGC CCATTGACGT CAATAATGAC GTATGTTCCC    300

ATAGTAACGC CAATAGGGAC TTTCCATTGA CGTCAATGGG TGGAGTATTT ACGGTAAACT    360

GCCCACTTGG CAGTACATCA AGTGTATCAT ATGCCAAGTA CGCCCCCTAT TGACGTCAAT    420

GACGGTAAAT GGCCCGCCTG GCATTATGCC CAGTACATGA CCTTATGGGA CTTTCCTACT    480

TGGCAGTACA TCTACGTATT AGTCATCGCT ATTACCATGG TGATGCGGTT TTGGCAGTAC    540

ATCAATGGGC GTGGATAGCG GTTTGACTCA CGGGGATTTC CAAGTCTCCA CCCCATTGAC    600

GTCAATGGGA GTTTGTTTTG GCACCAAAAT CAACGGGACT TTCCAAAATG TCGTAACAAC    660

TCCGCCCCAT TGACGCAAAT GGGCGGTAGG CGTGTACGGT GGGAGGTCTA TATAAGCAGA    720

GCTCGTTTAG TGAACCGTCA GATCGCCTGG AGACGCCATC CACGCTGTTT TGACCTCCAT    780

AGAAGACACC GGGACCGATC CAGCCTCCGC GGCCGGGAAC GGTGCATTGG AACGCGGATT    840

CCCCGTGCCA AGAGTGACGT AAGTACCGCC TATAGAGTCT ATAGGCCCAC CCCCTTGGCT    900

TCTTATGCAT GCTATACTGT TTTTGGCTTG                                     930
```

What is claimed is:

1. A method of introducing a selected nucleic acid into cells of a mammal, comprising: administering a composition comprising a cationic lipid-nucleic acid complex comprising the selected nucleic acid to the peritoneal cavity of the mammal, wherein the comnposition is substantially free of macroaggregates of the complex, wherein the selected nucleic acid encodes an RNA or polypeptide, and wherein administration of the cationic lipid-nucleic acid complex to the peritoneal cavity of the mammal results in detectable expression of the RNA or protein in the cells of the mammal.

2. The method of claim 1, wherein the cationic lipid-nucleic acid complex further comprises a neutral lipid.

3. The method of claim 2, wherein the molar ratio of cationic lipid to neutral lipid in the complex is at least about 1:20.

4. The method of claim 2, wherein the molar ratio of cationic lipid to neutral lipid in the complex is about 1:1.

5. The method of claim 1, wherein the cationic lipid-nucleic acid complex comprises a steroid.

6. The method of claim 1, wherein the cationic lipid-nucleic acid complex comprises a lipid selected from the group consisting of DOTAP, E-PC, L-PE, cholesterol, DOPE, and DDAB.

7. The method of claim 1, wherein the cationic lipid-nucleic acid complex comprises a site-directing molecule.

8. The method of claim 7, wherein the site-directing molecule is selected from the group consisting of an antibody and a ligand.

9. The method of claim 1, wherein the cationic lipid-nucleic acid complex is introduced into the peritoneal cavity of the mammal by intraperitoneal injection.

10. The method of claim 1, wherein the cationic lipid-nucleic acid complex is suspended in a physiologically acceptable medium for administration.

11. The method of claim 10, wherein the medium is selected from the group consisting of deionized water, saline, phosphate buffered saline, and 5% dextrose in water.

12. The method of claim 10, wherein the medium comprises a buffer, a stabilizer, or a biocide.

13. The method of claim 1 whereby the selected nucleic acid is introduced into cells of at least two tissues in the mammal.

14. The method of claim 1 whereby the selected nucleic acid is introduced into cells of at least two tissues in the mammal and expressed in said at least two tissues.

15. The method of claim 1, wherein the selected nucleic acid comprises DNA.

16. The method of claim 1 wherein the selected nucleic acid encodes a molecule selected from the group consisting of a ribozyme, an anti-sense molecule, and a protein.

17. The method of claim 1 wherein the selected nucleic acid comprises a DNA plasmid.

18. The method of claim 1 wherein the selected nucleic acid comprises a DNA expression cassette.

19. The method of claim 1 wherein at least about 50 μg of the selected nucleic acid is introduced into the mammal.

20. The method of claim 1, wherein the cationic lipid does not comprise DOTMA.

21. A mammalian transfection complex comprising:

a cationic lipid and a non-cationic lipid forming a lipid carrier ranging in size from 100 nm to 10 microns in diameter; combined with a selected nucleic acid in a ratio of less than 6:1 micrograms selected nucleic acid to nanomoles cationic lipid;

a physiologically acceptable medium for in vivo systemic administration; and, wherein said non-cationic lipid comprises a steroid and said complex does not aggregate in vitro and wherein the complex transfects a cell in vivo following systemic administration.

22. The mammalian transfection complex of claim 21, wherein the steroid is cholesterol.

23. The mammalian transfection complex of claim 21, wherein the nucleic acid is DNA.

24. A method of making a nucleic acid: lipid complex for systemic administration to a mammal comprising:

mixing a nucleic acid and a lipid carrier to provide a non-aggregating nucleic acid:lipid carrier complex having a mean diameter of less than about 10 microns, wherein the lipid carrier comprises cationic lipids and a steroid and wherein the nucleic acid to lipid carrier ratio is less than 6:1 micrograms DNA to nanomoles cationic lipid, wherein the complex is suspended in a physiologically acceptable medium.

25. The method of claim 24, wherein the medium is selected from the group consisting of deionized water, saline, phosphate buffered saline, and 5% dextrose in water.

26. The method of claim 24, wherein the steroid is cholesterol.

27. The method of claim 21 or 24, wherein the selected nucleic acid is a DNA expression cassette comprising: a promoter, and a DNA subsequence encoding a gene product.

28. A method of making a nucleic acid: lipid complex for systemic administration to a mammal comprising:

mixing a selected nucleic acid and a lipid carrier comprising cationic and, optionally, non cationic lipids, said carrier having a mean diameter of less than about 10 microns, wherein the molar ratio of cationic lipids to non cationic lipids ranges from 1:20 to 1:0, resulting in a non-aggregating nucleic acid lipid carrier complex, wherein the nucleic acid to lipid carrier ratio is less than 6:1 micrograms selected nucleic acid to nanomoles cationic lipid wherein the non-aggregating nucleic acid lipid carrier complex is suspended in a physiologically acceptable medium.

29. The method of claim 28, wherein the non-cationic lipid is cholesterol.

30. The method of claim 28, wherein the molar ratio of cationic to non-cationic lipids is about 1:1.

31. The method of claim 24 or 28, further comprising loading the nucleic acid carrier complex into a systemic delivery container.

32. The method of claim 24 or 28, further comprising loading the nucleic acid carrier complex into a syringe.

* * * * *